(12) United States Patent
Nitz et al.

(10) Patent No.: US 8,202,896 B2
(45) Date of Patent: Jun. 19, 2012

(54) COMPOUNDS, COMPOSITIONS AND METHODS FOR TREATING OR PREVENTING PNEUMOVIRUS INFECTION AND ASSOCIATED DISEASES

(75) Inventors: Theodore J. Nitz, Pottstown, PA (US); Janet A. Gaboury, Blue Bell, PA (US); Christopher J. Burns, Malvern, PA (US); Sylvie Laguerre, Exton, PA (US); Daniel C. Pevear, Harleysville, PA (US); Thomas A. Lessen, Langhorne, PA (US); David J. Rys, Philadelphia, PA (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 833 days.

(21) Appl. No.: 10/524,162

(22) PCT Filed: Aug. 11, 2003

(86) PCT No.: PCT/US03/25165
§ 371 (c)(1),
(2), (4) Date: Jun. 17, 2005

(87) PCT Pub. No.: WO2004/014316
PCT Pub. Date: Feb. 19, 2004

(65) Prior Publication Data
US 2005/0288344 A1    Dec. 29, 2005

Related U.S. Application Data

(60) Provisional application No. 60/402,450, filed on Aug. 9, 2002.

(51) Int. Cl.
*A61K 31/41* (2006.01)
*C07D 257/06* (2006.01)

(52) U.S. Cl. ........................ 514/381; 548/251
(58) Field of Classification Search .................. 514/381; 548/251
See application file for complete search history.

(56) References Cited

U.S. PATENT DOCUMENTS

| | | | |
|---|---|---|---|
| 3,954,398 A | 5/1976 | Ramanathan | ........................ 8/41 |
| 4,308,382 A | 12/1981 | Zenitz | |
| 4,324,794 A | 4/1982 | Tidwell et al. | |
| 4,943,574 A | 7/1990 | Raeymaekers et al. | |
| 5,098,920 A | 3/1992 | Reitz | |
| 5,227,429 A | 7/1993 | Kawamura et al. | ............. 525/92 |
| 5,773,646 A | 6/1998 | Chandrakumar et al. | |
| 6,495,580 B1 | 12/2002 | Nitz et al. | ..................... 514/365 |
| 2005/0288345 A1 | 12/2005 | Rys et al. | |

FOREIGN PATENT DOCUMENTS

| | | |
|---|---|---|
| EP | 0 795 549 | 9/1997 |
| GB | 1 508 391 | 4/1978 |
| JP | 60-237047 | 11/1985 |
| WO | WO95/00131 | 1/1995 |
| WO | WO97/05125 | 2/1997 |
| WO | WO99/38508 | 8/1999 |
| WO | WO 9938508 A1 * | 8/1999 |
| WO | WO01/00611 | 1/2001 |
| WO | WO01/00612 | 1/2001 |
| WO | WO01/00615 | 1/2001 |
| WO | 02/059132 | 8/2002 |
| WO | WO02/059132 | 8/2002 |

OTHER PUBLICATIONS

DeLuca et al. "Formulation of Small Volume Parenerals" Pharmaceutical Dosage Forms vol. 1: Parenteral Medications, Marrcell Dekker, 1992, pp. 173-175.*
Abstract/Poster presented by T.J. Nitz at 40th Inter-science Conference on Antimicrobial Agents and Chemotherapy (Toronto, Ont.) on Sep. 16, 2000.
Schlegel, D.C. et al. "Bulky Amine Analogues of Ketoprofen: Potent Antiinflammatory Agents"; J. Med. Chem. 27: 1682-1690 (1984).
Baker, B.R. et al. "Irreversible Enzyme Inhibitors. 181. Inhibition of Brain Choline Acetyltransferace by Derivatives of 4-Stilbazole"; J. Med. Chem. 14(4): 315-322-(1971).
DeClercq, E. "Perspectives for the chemotherapy of respiratory Synctial virus (RSV) infections"; International Journal of Antimocrobial Agents 7: 193-202 (1996).
Cammarata, Journal of Medicinal Chemistry, 1972, 15(6), 573-577.
Avis, Kenneth, 1999, Pharmaceutical Dosage Forms vol. 1:Parenteral Medications, Marrcel Dekker, 173-175.
Canadian Examiner's Requisition, dated Jun. 17, 2010 (3 pages).
EPO Search dated Apr. 12, 2002 (6 pages).

* cited by examiner

*Primary Examiner* — Joseph Kosack
(74) *Attorney, Agent, or Firm* — Hayes Soloway P.C.

(57) ABSTRACT

Compounds, compositions and methods are provided for the prophylaxis and treatment of infections caused by viruses of the Pneumovirinae subfamily of Paramyxoviridae and diseases associated with such infection.

32 Claims, No Drawings

COMPOUNDS, COMPOSITIONS AND METHODS FOR TREATING OR PREVENTING PNEUMOVIRUS INFECTION AND ASSOCIATED DISEASES

This application is a 35 U.S.C. §371 application based on PCT/US03/25165, filed 11 Aug. 2003, which in turn claims the benefit of U.S. Provisional Application 60/402,450 filed 9 Aug. 2002. The entire disclosure of each of the above identified applications is incorporated by reference herein.

FIELD OF THE INVENTION

The present invention relates to compounds, compositions and methods for preventing and treating viral infections, and the diseases associated therewith, particularly those viral infections and associated diseases caused by pneumoviruses.

BACKGROUND OF THE INVENTION

The Pneumovirinae subfamily of the Paramyxoviridae family consists of pneumoviruses that cause significant disease in humans and a number of animal species including cattle, goats, sheep, mice and in avian species.

Human respiratory syncytial virus (RSV), the prototypic member of the pneumovirus group, is the major pediatric viral respiratory tract pathogen, causing pneumonia and bronchiolitis in infants and young children. RSV disease is seasonal, with outbreaks in the U.S. typically beginning in November and continuing through April. During these yearly epidemics, approximately 250,000 infants contract RSV pneumonia, and up to 35% are hospitalized. Of those hospitalized, mortality rates of up to 5% have been reported. Children with underlying conditions such as prematurity, congenital heart disease, bronchopulmonary dysplasia and various congenital or acquired immunodeficiency syndromes are at greatest risk of serious RSV morbidity and mortality. In adults, RSV usually causes upper respiratory tract manifestations but can also cause lower respiratory tract disease, especially in the elderly and in immunocompromised persons. Infection in elderly and immunocompromised persons can be associated with high death rates. Natural infection with RSV fails to provide full protective immunity. Consequently, RSV causes repeated symptomatic infections throughout life.

The pneumoviruses of animals and avian species are similar to the human virus antigenically, in polypeptide composition and in disease causation.

Attempts to develop vaccines for RSV are ongoing, but none have yet been demonstrated to be safe and efficacious. Vaccine development has been shadowed by adverse reactions exhibited by the initial formalin-inactivated RSV vaccine introduced in the late 1960s. Immunized children showed an increased incidence of RSV lower respiratory tract disease and developed abnormally severe illnesses, including death.

Chemotherapy with ribavirin [1-beta-D-ribofuranosyl-1H-1,2,4-triazole-3-carboxamide], an antiviral nucleoside which is the only pharmaceutical approved by the U.S. Food and Drug Administration (FDA) for treatment of RSV disease, is considered only for certain RSV patients (e.g., those at high risk for severe complications or who are seriously ill with this infection). However, its efficacy and value are controversial. Recent studies have reported a failure to demonstrate either clinical or economic benefit to patients of ribavirin treatment. Moreover, ribavirin has certain toxic side-effects and, in order to minimize these, must be administered by inhalation as an aerosol in an enclosed environment. However, drug delivery as an aerosol in general can be hampered by low solubility of the drug in the carrier solvent.

A human intravenous immune globulin (IVIG) preparation is licensed for prophylactic use in certain patients at high-risk for RSV disease. Administration of this drug requires intravenous infusion of a large volume over a 2 to 4 hour period in children who have limited venous access due to prior intensive therapy, as well as compromised cardiopulmonary function. Moreover, intravenous infusion necessitates monthly hospital visits during the RSV season, which in turn places children at risk of nosocomial infections.

Thus, a need exists for new anti-viral agents and treatments for RSV infection that overcome the shortcomings of existing pharmaceutical preparations.

International Patent Application No. PCT/US99/01985 (filed on Jan. 29, 1999, now published as WO 99/38508) discloses compounds, compositions, and methods for treating or preventing pneumovirus infections and associated diseases, and is hereby expressly incorporated-by-reference in its entirety. International Patent Application No. PCT/US02/02338 (filed on Jan. 28, 2002, now published as WO 02/059132) discloses intermediate compounds useful for making antiviral compounds.

SUMMARY OF THE INVENTION

The invention provides a compound of the formula: I

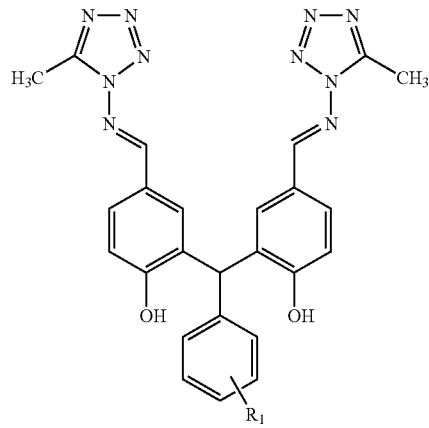

wherein:

$R_1$ represents a radical selected from the group consisting of

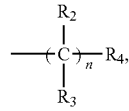

—$NR_5R_6$, —$SO_2NR_7R_8$, hydroxyalkyl, hydroxyalkoxy, polyhydroxyalkyl, alkoxyalkoxy, polyfluoroalkyl, dialkylaminoalkyl, $R_9$, —$OR_9$,

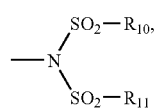

and HET; n being an integer from 1 to 4;

$R_2$ and $R_3$ are each independently selected from the group consisting of straight or branched chain alkyl and hydrogen;

$R_4$ is a radical selected from the group consisting of a substituted or unsubstituted phenyl radical, an unsubstituted or substituted heterocyclic radical, and —$NR_{12}R_{13}$;

R$_5$ and R$_7$ are independently selected from the group consisting of alkoxyalkyl, hydroxyalkyl, polyhydroxyalkyl, aralkyl, R$_9$, —(C═O)R$_{14}$ and —(C═O)R$_9$;

R$_6$, R$_8$, R$_{12}$, and R$_{13}$ are independently selected from the group consisting of hydrogen, alkyl, alkoxyalkyl, polyfluoroalkyl, hydroxyalkyl, polyhydroxyalkyl, aralkyl, R$_9$, —(C═O)R$_{15}$ and —(C═O)R$_9$;

or R$_5$ and R$_6$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

or R$_7$ and R$_8$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

said phenyl and heterocyclic radical substituents being at least one selected from the group consisting of alkyl, amino, hydroxy, carbonyl, monoalkylamino, dialkylamino, halogen, and alkoxy;

R$_9$ is a radical of the formula —W—O(C═O)—CH$_3$, W being a straight- or branched-chain alkylene group of 1 to 6 carbon atoms;

R$_{11}$ and R$_{11}$ are radicals independently selected from the group consisting of alkyl, halo, haloalkyl, and polyfluoroalkyl;

HET represents an unsubstituted or substituted five to seven membered heterocyclic ring containing one to four heteroatoms independently selected from nitrogen, oxygen or sulfur, whereby the point of attachment to the heterocyclic ring is not at a nitrogen atom, said heterocyclic ring substituents being one or more radicals selected from the group consisting of alkyl, amino, hydroxy, carbonyl, oxo, monoalkylamino, and dialkylamino;

R$_{14}$ is a hydroxyalkyl, alkoxyalkyl or cycloalkyl group;

R$_{15}$ is an alkyl, hydroxyalkyl, alkoxyalkyl or cycloalkyl group, and pharmaceutically acceptable salts of said compound.

The invention also relates to pharmaceutical compositions containing the antiviral compounds of Formula I and the corresponding methods of use for treating and preventing infections caused by viruses from the Pneumovirinae family, as well as the intermediate compounds and related methods of preparing the antiviral compounds described herein.

DETAILED DESCRIPTION OF THE INVENTION

In one aspect, the instant invention provides compounds of Formula I:

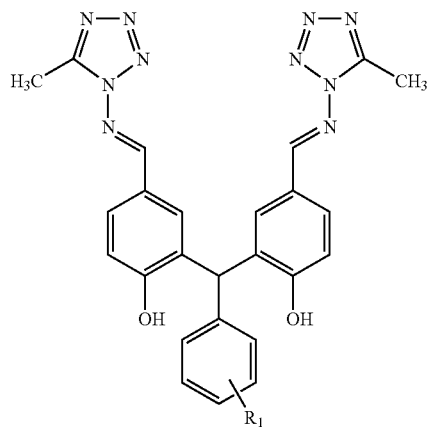

wherein R$_1$ is as defined above.

A preferred aspect of the invention includes the compound of Formula I(a):

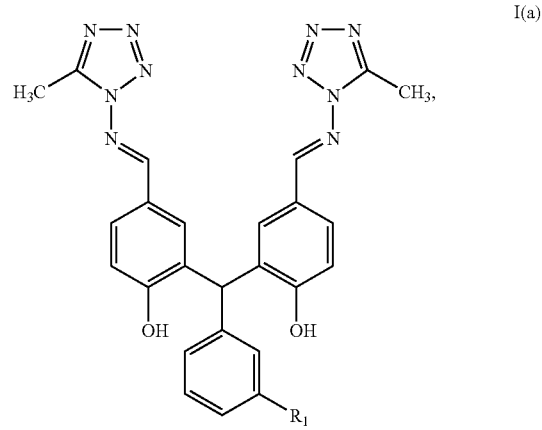

wherein R$_1$ is as defined above.

Preferred compounds of Formula 1(a) include the compounds wherein R$_1$ is —NR$_5$R$_6$, wherein R$_5$ is a hydroxyalkyl group and R$_6$ is an alkyl group.

A preferred aspect of the invention includes the compound of Formula I(b):

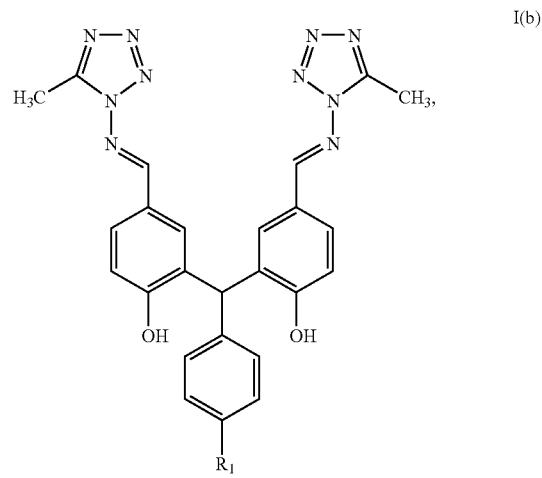

wherein R$_1$ is as defined above.

An ultimately preferred aspect of the invention also includes the compound having the formula:

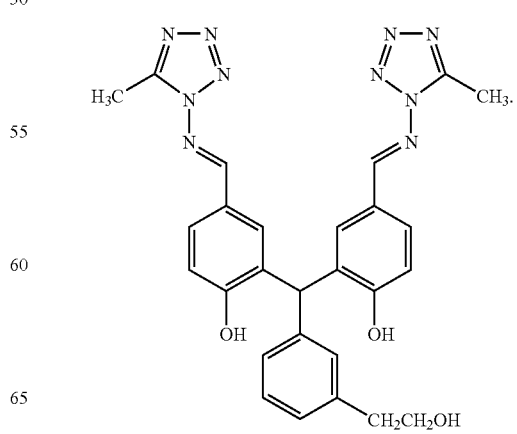

Another preferred aspect of the invention is the compound having the formula:

The compound of Formula I is useful for treating and preventing RSV disease. The preferred compound of Formula I(a) has improved solubility in pharmaceutical formulations. In particular, the compounds of Formula I(a) have improved solubility in ethanolic solvents. The indicated improved solubility characteristics facilitate the preparation of pharmaceutical formulations and the delivery of the pharmaceutical formulations to a patient's pulmonary system using electrohydrodynamic (EHD) technology. Electrohydrodynamic spraying is a known process whereby solutions are aerosolized using electrical forces. In an EHD spray nozzle, the fluid to be aerosolized flows over a region of high electric field strength and receives a net electrical charge that remains on the surface of the fluid. As the solution exits the nozzle, the repelling force of the surface charge generates a thin jet of fluid. The jet breaks up into droplets of uniform size that collectively form a cloud. The result is an aerosolized solution having a monodispersed particle size distribution and near zero velocity. The improved solubility of the compound of Formula I(a) in the formulations used in an EHD device facilitates the delivery of higher concentrations of the desired compound to the patient pulmonary tissue with fewer numbers of actuations of the EHD device. One of ordinary skill in the art may practice the instant invention with EHID devises that are commercially available or otherwise with known EHD technology.

In accordance with another aspect, the present invention provides a class of novel intermediates that are useful in preparing the anti-viral agents described herein. These intermediates have the general formula:

II wherein:

$R_1'$ represents a radical selected from the group consisting of $-NR_5R_6$, $-SO_2NR_7R_9$, hydroxyalkyl, hydroxyalkoxy, polyhydroxyalkyl, alkoxyalkoxy, polyfluoroalkyl, dialkylaminoalkyl, $R_9$, $-OR_9$.

and HET; n being an integer from 1 to 4;

$R_2$ and $R_3$ are each independently selected from the group consisting of straight or branched chain alkyl and hydrogen;

$R_4$ is a radical selected from the group consisting of a substituted or unsubstituted phenyl radical, an unsubstituted or substituted heterocyclic radical, and $-NR_{12}R_{13}$;

$R_5$ and $R_7$ are independently selected from the group consisting of alkoxyalkyl, hydroxyalkyl, polyhydroxyalkyl, aralkyl, $R_9$, $-(C=O)R_{14}$ and $-(C=O)R_9$;

$R_6$, $R_8$, $R_{12}$, and $R_{13}$ are independently selected from the group consisting of hydrogen, alkyl, alkoxyalkyl, polyfluoroalkyl, hydroxyalkyl, polyhydroxyalkyl, aralkyl, $R_9$, $-(C=O)R_{15}$ and $-(C=O)R_9$;

or $R_5$ and $R_6$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

or $R_7$ and $R_8$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

said phenyl and heterocyclic radical substituents being at least one selected from the group consisting of alkyl, amino, hydroxy, carbonyl, monoalkylamino, dialkylamino, halogen, and alkoxy;

$R_9$ is a radical of the formula $-W-O(C=O)-CH_3$, W being a straight- or branched-chain alkylene group of 1 to 6 carbon atoms;

$R_{10}$ and $R_{11}$ are radicals independently selected from the group consisting of alkyl, halo, haloalkyl, and polyfluoroalkyl;

HET represents an unsubstituted or substituted five to seven membered heterocyclic ring containing one to four heteroatoms independently selected from nitrogen, oxygen or sulfur, whereby the point of attachment to the heterocyclic ring is not at a nitrogen atom, said heterocyclic ring substituents being one or more radicals selected from the group consisting of alkyl, amino, hydroxy, carbonyl, oxo, monoalkylamino, and dialkylamino;

$R_{14}$ is a hydroxyalkyl, alkoxyalkyl or cycloalkyl group;

$R_{15}$ is an alkyl, hydroxyalkyl, alkoxyalkyl or cycloalkyl group, and pharmaceutically acceptable salts of said compound.

In accordance with another aspect, the present invention provides a class of novel intermediates that are useful in preparing the anti-viral agents described herein. These intermediates have the general formula:

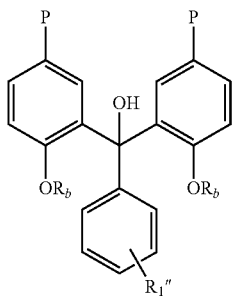

III wherein $R_b$ is selected from the group consisting of —CH$_2$OCH$_3$, —CH$_2$OCH$_2$CH$_3$, —CH(CH$_3$)OCH$_2$CH$_3$, —CH$_2$—OCH$_2$CH$_2$—OCH$_3$,

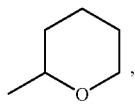

—CH$_2$—OCH$_2$CH$_2$—Si(CH$_3$)$_3$, —CH$_3$, —CH$_2$C$_6$H$_5$, —(CH$_2$)$_2$Si(CH$_3$)$_3$, —CON(R$_c$R$_d$)$_2$, —CSN(R$_c$R$_d$)$_2$, and —PO(NR$_c$R$_d$)$_2$;

$R_c$ and $R_d$ are independently selected from an alkyl group;

$R_1''$ represents a radical selected from the group consisting of

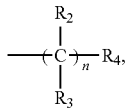

—NR$_5$R$_6$, —SO$_2$NR$_7$R$_8$, hydroxyalkyl, hydroxyalkoxy, polyhydroxyalkyl, alkoxyalkoxy, polyfluoroalkyl, dialkylaminoalkyl, R$_9$, —OR$_9$,

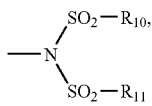

and HET; n being an integer from 1 to 4;

$R_2$ and $R_3$ are each independently selected from the group consisting of straight or branched chain alkyl and hydrogen;

$R_4$ is a radical selected from the group consisting of a substituted or unsubstituted phenyl radical, an unsubstituted or substituted heterocyclic radical, and —NR$_{12}$R$_{13}$;

$R_5$ and $R_7$ are independently selected from the group consisting of alkoxyalkyl, hydroxyalkyl, polyhydroxyalkyl, aralkyl, R$_9$, —(C=O)R$_{14}$ and —(C=O)R$_9$;

$R_6$, $R_9$, $R_{12}$, and $R_{13}$ are independently selected from the group consisting of hydrogen, alkyl, alkoxyalkyl, polyfluoroalkyl, hydroxyalkyl, polyhydroxyalkyl, aralkyl, R$_9$, —(C=O)R$_{15}$ and —(C=O)R$_9$;

or $R_5$ and $R_6$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

or $R_7$ and $R_9$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

said phenyl and heterocyclic radical substituents being at least one selected from the group consisting of alkyl, amino, hydroxy, carbonyl, monoalkylamino, dialkylamino, halogen, and alkoxy;

$R_9$ is a radical of the formula —W—O(C=O)—CH$_3$, W being a straight- or branched-chain alkylene group of 1 to 6 carbon atoms;

$R_{10}$ and $R_{11}$ are radicals independently selected from the group consisting of alkyl, halo, haloalkyl, and polyfluoroalkyl;

HET represents an unsubstituted or substituted five to seven membered heterocyclic ring containing one to four heteroatoms independently selected from nitrogen, oxygen or sulfur, whereby the point of attachment to the heterocyclic ring is not at a nitrogen atom, said heterocyclic ring substituents being one or more radicals selected from the group consisting of alkyl, amino, hydroxy, carbonyl, oxo, monoalkylamino, and dialkylamino;

$R_{14}$ is a hydroxyalkyl, alkoxyalkyl or cycloalkyl group;

$R_{15}$ is an alkyl, hydroxyalkyl, alkoxyalkyl or cycloalkyl group;

P is a protected formaldehyde group such as:

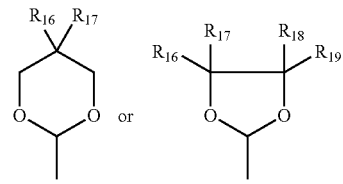

wherein $R_{16}$, $R_{17}$, $R_{18}$ and $R_{19}$ are independently selected from the group consisting of hydrogen and alkyl; and pharmaceutically acceptable salts of said compound.

The present invention also provides new synthetic methods useful for preparation of the compounds described herein.

One method comprises making the antiviral compounds of Formula I, from the compounds of Formula II, by reacting the aldehyde moieties in Formula II with 1-amino-5-methyltetrazole to produce the desired product as shown below:

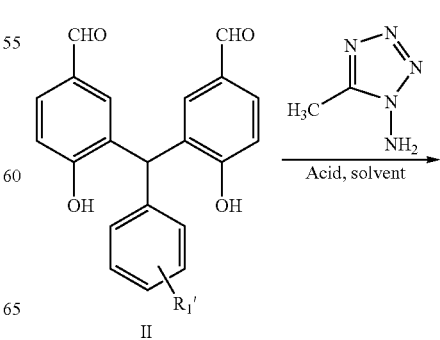

II

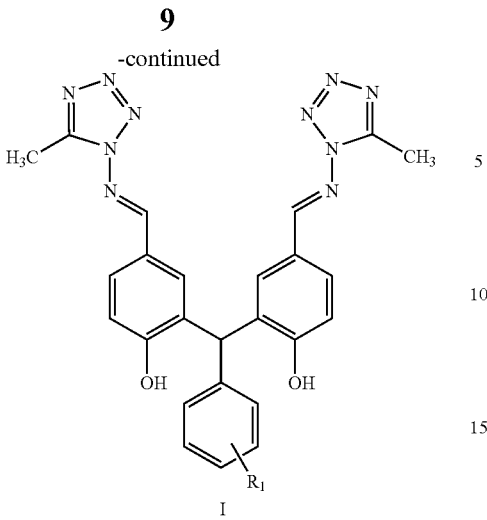

I

A method useful in the ultimate preparation of antiviral compounds involves deprotection and reduction of the $R_1''$-substituted triphenylcarbinol derivative of Formula III with hydriodic acid and acetic acid, preferably at room temperature, to generate the aldehyde of Formula II as shown below:

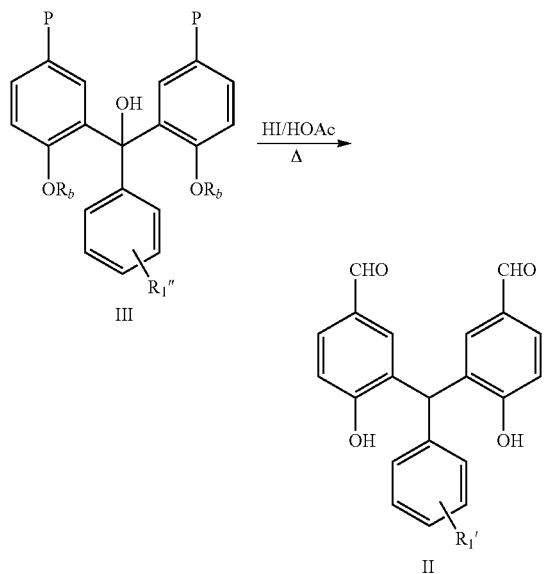

Another method useful in the ultimate preparation of antiviral compounds involves the preparation of the compound of the Formula III via the reaction shown below:

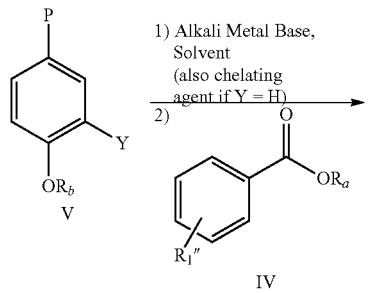

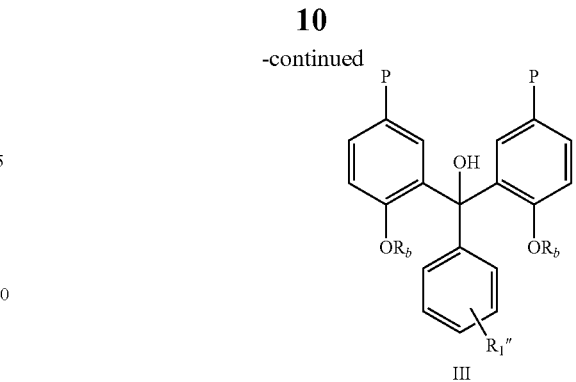

III wherein Y is hydrogen, bromo or iodo, and $R_b$ and P are as described above, and $R_a$ is a lower alkyl group According to still another aspect, the present invention provides pharmaceutical compositions comprising one or more of the above-described compounds in combination with a pharmaceutically acceptable carrier medium.

In accordance with a further aspect, the present invention provides a method for preventing and treating pneumovirus infection and for preventing and treating diseases associated with pneumovirus infection in living hosts, by administering to a living host susceptible to pneumovirus infection a therapeutically effective amount of a compound of the above structures and/or the isomers and pharmaceutically acceptable salts of said compounds, or pharmaceutical compositions containing same.

The starting materials for preparing the compounds of the invention are either commercially available or can be conveniently prepared according to one of the synthetic schemes illustrated below or otherwise using known chemistry procedures.

1) Preparation of the Benzoate Ester Intermediate:

The ester intermediates of Formula IV may be purchased from commercial sources or alternatively can be readily synthesized by standard procedures which are well known to those of ordinary skill in the art, or otherwise by following one of the general synthetic schemes shown below:

a) The compound of Formula IV(a) can be prepared via the reaction shown below, by reacting the appropriate bromobenzene wherein $R_1''$ is selected as appropriate to obtain the desired product, with magnesium, isopropylmagnesium bromide, or isopropylmagnesium chloride; in an inert solvent, such as tetrahydrofuran, followed by the addition of the appropriate dialkyl carbonate wherein $R_a$ is as defined above:

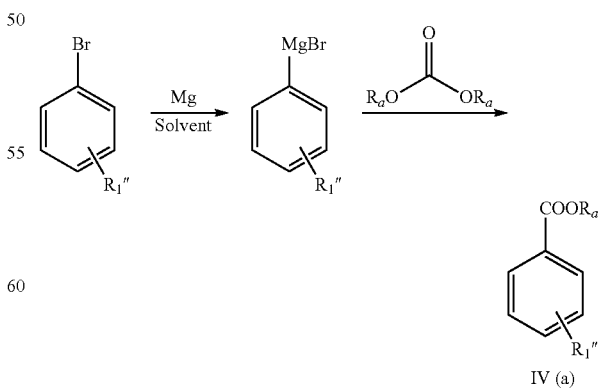

IV (a)

b) The compound of Formula IV(b) can be prepared according to the reaction shown below, wherein $R_z$ is the desired substituent, such as alkyl, benzyl, alkoxyalkyl, trialkylsilyloxyalkyl, triarylsilyloxyalkyl, ethoxydimethylsilane or a sulfonate, such as a tosylate or mesylate; $R_a$ is as defined above; and X' is a bromo or iodo group. The reaction is conducted in an inert solvent, such as acetonitrile, toluene, or 1-methyl-3-pyrrolidinone, in the presence of a base, such as N,N-diisopropylethylamine, potassium carbonate, or sodium carbonate:

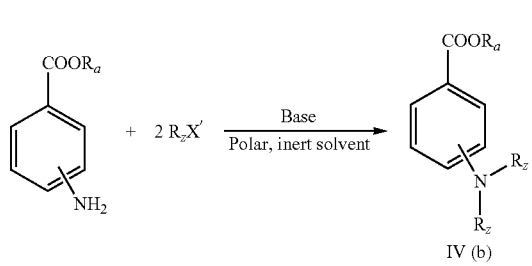

c) The compound of Formula IV(c) can be prepared according to the reaction shown below wherein $R_a$ is as defined above, and $R_y$ and $R_z$ are selected as appropriate to obtain the desired product. The reaction is conducted in the presence of sodium borohydride or sodium cyanoborohydride in an inert solvent, such as tetrahydrofuran (THF). A preferred method involves the addition of a small amount of water to solubilize the sodium borohydride and initiate the reaction:

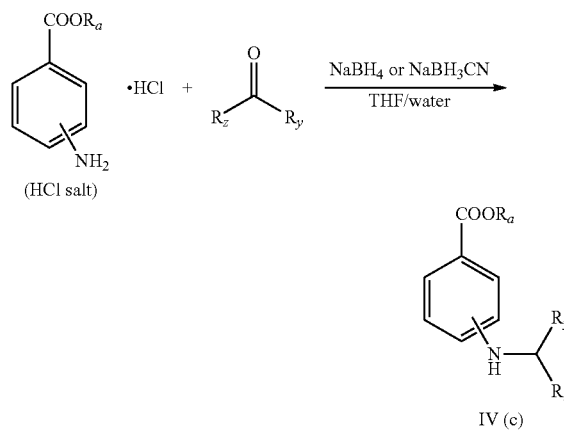

d) The compound of Formula IV(d) can be prepared according to the reaction shown below, wherein Alk is an alkyl group and $R_a$ is as defined above. The reaction is conducted with an alcohol (Alk-OH), such as ethanol or propanol, in the presence of Raney Nickel, and at elevated temperatures:

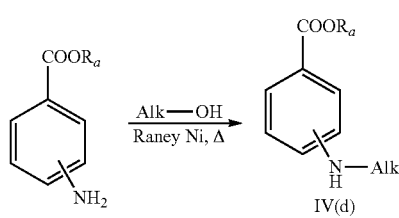

e) The compound of Formula IV(e) can be prepared according to the reaction shown below wherein $R_a$ is as defined above, $R_y$ and $R_z$ are selected as appropriate to obtain the desired product, and X' is a bromo, iodo, or sulfonate group; in an inert polar solvent, such as acetonitrile, ethanol, 1-methyl-3-pyrrolidinone, in the presence of a base, such as N,N-diisopropylethylamine:

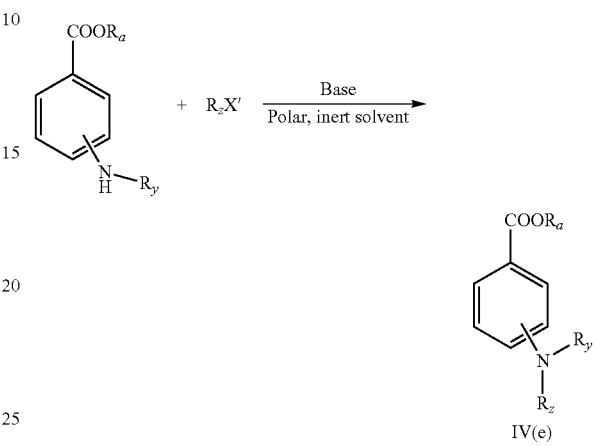

f) The compound of Formula IV(f) can be prepared according to the hydrogenation (deprotection) reaction shown below, wherein $R_a$ is as defined above, and $R_z$ is selected as appropriate to obtain the desired product. The reaction is conducted with 10% palladium on carbon in an alcoholic solvent, such as methanol or ethanol.

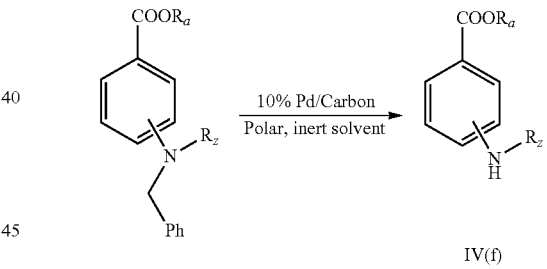

The hydrogenation (deprotection) reaction can be performed after the compound of Formula IV(f) is used to prepare a triaryl methanol intermediate of Formula III.

g) The compound of Formula IV(g) can be prepared according to the reaction shown below, wherein m is an integer from 4 to 6, and $R_a$ is as defined above. The reaction is conducted in the presence of a base, such as N,N-diisopropylethylamine, and in an inert solvent, such as toluene, preferably at refluxing temperature:

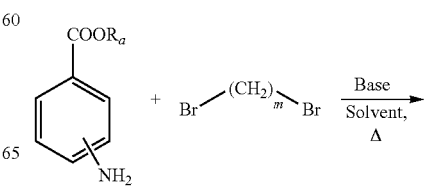

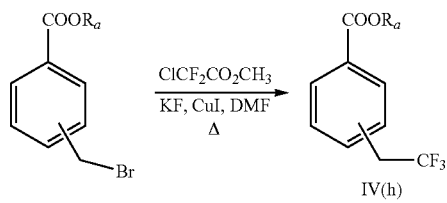

IV(g)

h) The compound of Formula IV(h) can be prepared according to the reaction shown below. The reaction is conducted with methyl 2-chloro-2,2-difluoroacetate, in the presence of potassium fluoride and copper iodide, in a solvent, such as N,N-dimethylformamide, and at elevated temperatures:

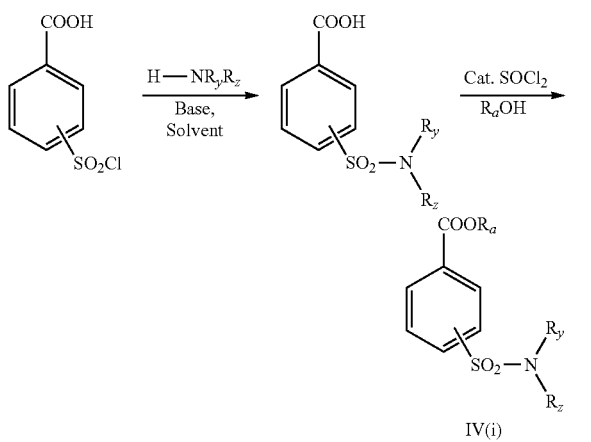

i) The compound of Formula IV(i) can be prepared according to the reaction shown below, by adding 3-chlorosulfonyl benzoic acid to a mixture of the indicated amine and an amine base, such as triethylamine, and in an inert solvent, for example, tetrahydrofuran; followed by dissolving the resulting sulfonamide benzoic acid in alcohol of the formula $R_aOH$, wherein $R_a$ is as defined above, and $R_y$ and $R_z$ are selected as appropriate to obtain the desired product; preferably in the presence of a catalytic amount of thionyl chloride:

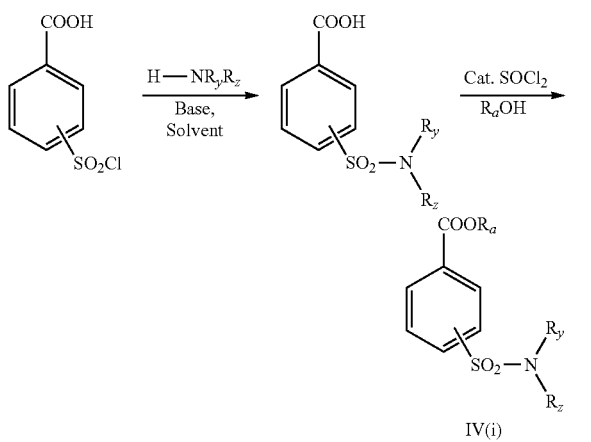

j) The compound of Formula IV(j) can be prepared according to the reaction shown below, and is performed in the presence of an excess amount of the substituted amine: $-NR_yR_z$, wherein $R_y$ and $R_z$ are selected as appropriate to obtain the desired product, and $R_a$ is as defined above; in an inert solvent such as tetrahydrofuran:

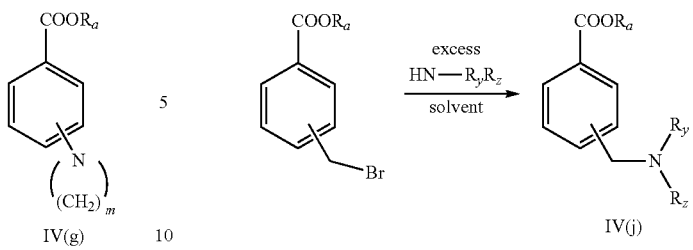

IV(j)

2) Preparation of Di-Protected Compound of Formula V:

The compound of Formula V can be prepared according to the reaction schemes (a), (b) and (c) shown below. The order of the protection conditions for the preparation of the di-protected compound of Formula V may be reversed as shown in the reactions in (a) and (b) below, and the single-protected intermediates of Formula VII(a-d) prepared therein may be isolated and/or purified if desired prior to preparation of the compound of Formula V. The 3-substituted 4-hydroxybenzaldehyde of Formula VIII may be purchased from commercial sources or alternatively is readily synthesized by standard procedures which are well known to those of ordinary skill in the art.

(a) The compounds of Formula V can be conveniently prepared according to the reactions shown below.

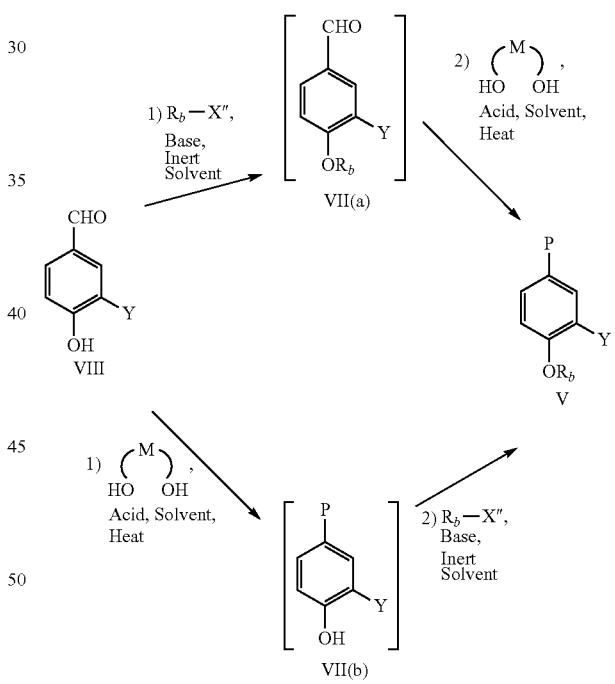

The intermediate compound of Formula VII(a), wherein Y is hydrogen, bromo, or iodo, $R_b$ is $-CH_2OCH_3$, $-CH_2OCH_2CH_3$, $-CH_2-OCH_2CH_2-OCH_3$, $-CH_2-OCH_2CH_2-Si(CH_3)_3$, $-CH_3$, $-CH_2C_6H_5$, $-(CH_2)_2Si(CH_3)_3$, $-CON(R_cR_d)_2$, $-CSN(R_cR_d)_2$, and $-PO(NR_cR_d)_2$, wherein $R_c$ and $R_4$ are independently selected from an alkyl group, X" is a halogen such as chloro, bromo, or iodo; may be prepared according to the reaction shown above. The reaction is conducted in the presence of a base such as diisopropylethylamine, triethylamine, potassium carbonate, sodium hydride, or pyridine; in an inert solvent; and preferably at temperatures ranging from −20° C. to 100° C.

Depending on the base, a preferable inert solvent may be one or more of the following: dichloromethane, tetrahydrofuran, 1-methyl-2-pyrrolidinone, dimethyl sulfoxide, acetone, or N,N-dimethylformamide.

The intermediate of Formula VII(a) may be used to prepare the compound of Formula V according the reaction shown above, wherein P is a protected formaldehyde group such as:

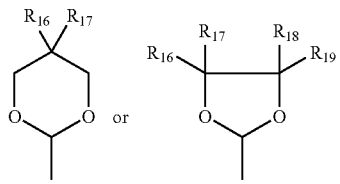

wherein $R_{16}$, $R_{17}$, $R_{18}$ and $R_{19}$ are independently selected from the group consisting of hydrogen or alkyl. The reaction is conducted by refluxing VII(a) with

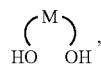

where M is $(CH_2-CR_{16}R_{17}-CH_2)$ or $(CR_{16}R_{17}-CR_{18}R_{19})$ and $R_{16}$, $R_{17}$, $R_{18}$ and $R_{19}$ are independently selected from the group consisting of hydrogen or alkyl; in the presence of an acid, such as, pyridinium para-toluenesulfonate, pyridinium hydrochloride, p-toluenesulfonic acid monohydrate, 2,4,6-trimethylpyridinium p-toluenesulfonate, camphorsulfonic acid, or Amberlyst®-15; and in an inert solvent, such as benzene, toluene, cyclohexane or tetrahydrofuran, preferably with the azeotropic removal of water. The acid is preferably a mild acid and/or preferably used in a catalytic amount.

Alternatively, the intermediate compound of Formula VII(b), wherein Y, M and P are as previously defined may be prepared according to the reaction shown above. The intermediate of Formula VII(b) then may be used to prepare the compound of Formula V, wherein $R_b$ is defined above. The reaction conditions of the protection steps are analogous to those used for preparing compound VII(a) and preparing compound V therefrom.

(b) The compounds of Formula V also may be conveniently prepared according to the reactions below.

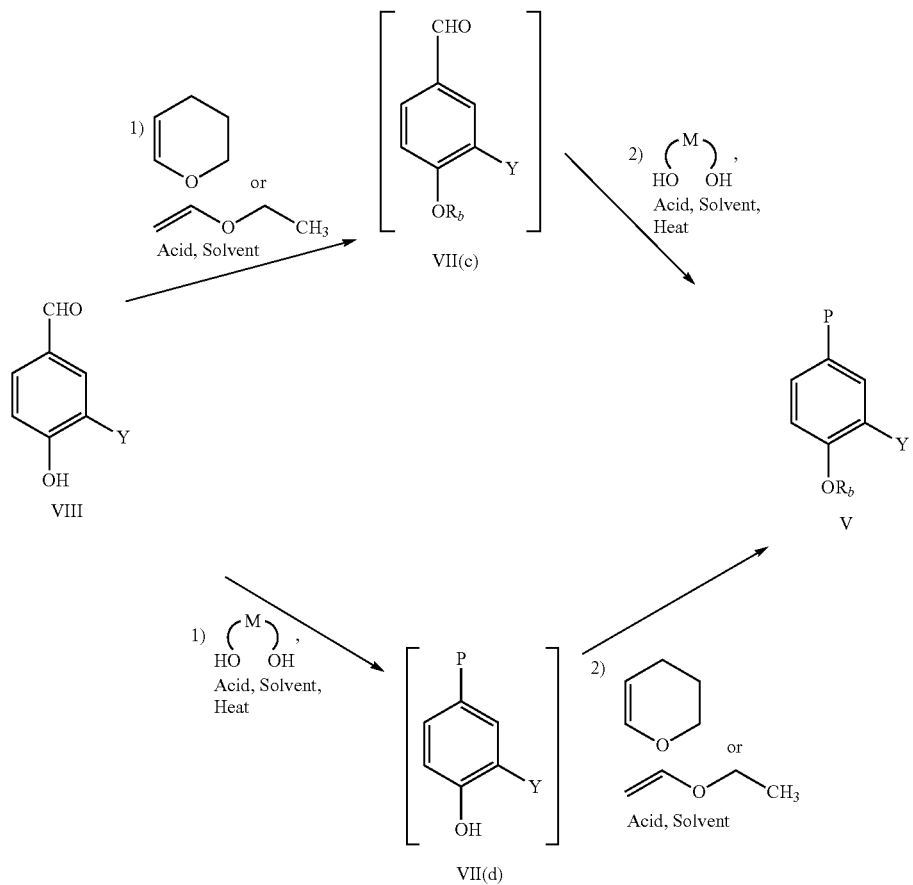

The intermediate compound of Formula VII(c), wherein $R_b$ is

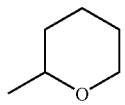

or —CH(CH$_3$)OCH$_2$CH$_3$, Y is hydrogen, bromo, or iodo, and M and P are as defined above may be prepared according to the reaction shown above. The reaction is conducted in the presence of an acid catalyst, such as pyridinium para-toluenesulfonate, dry hydrochloric acid, pyridinium hydrochloride, camphorsulfonic acid, 2,4,6-trimethylpyridinium-toluenesulfonate, Amberlyst®-15, or p-toluenesulfonic acid monohydrate; and in a non-polar inert solvent, such as dichloromethane, ethyl acetate, dimethoxyethane, p-dioxane, chloroform, dichloroethane, or tetrahydrofuran; at temperatures between −20° C. and 140° C., or otherwise above the freezing point and up to the reflux temperature of the solvent. The compound of Formula V then may be prepared by protecting the aldehyde group of Formula VII(c) as analogously described above in paragraph 2(a). Similarly the protection steps may be conducted in reverse order so as to make the compound of Formula V via the intermediate of Formula VII(d).

(c) The compound of Formula V, wherein $R_b$ is —CH$_2$OCH$_3$, also may be prepared according to the reaction shown below, by reacting the 3-substituted 4-hydroxybenzaldehyde of Formula VIII, wherein Y is hydrogen, bromide, or iodide; with dimethoxymethane and P$_2$O$_5$, in an inert solvent such as, dichloromethane, chloroform, toluene, and cyclohexane, preferably at room temperature, and preferably in the presence of diatomaceous earth (or Celite™). The aldehyde group of Formula VII(e) is protected as described in paragraph 2(a) above.

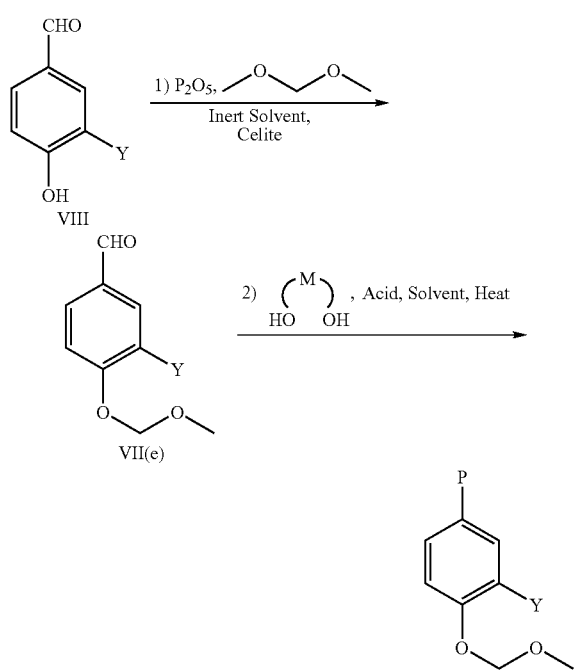

3) Preparation of the Tri-Aryl Methanol Compounds of Formula III:

(a) Direct Metalation:

The tri-aryl methanol of Formula III can be prepared by direct metalation of two equivalents of a di-protected benzaldehyde of Formula V(a) according to the reaction shown below:

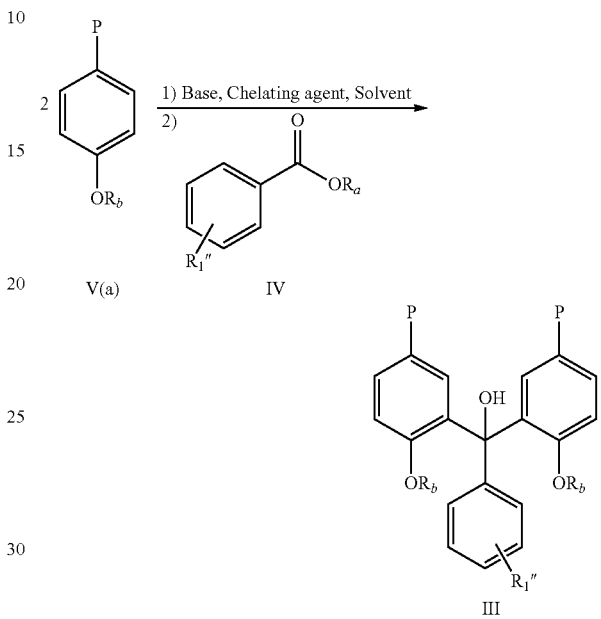

wherein $R_b$ is —CH$_2$OCH$_3$, —CH$_2$OCH$_2$CH$_2$, —CH$_2$—OCH$_2$CH$_2$—OCH$_3$, —CH$_2$—OCH$_2$CH$_2$—Si(CH$_3$)$_3$, —CH$_3$, —(CH$_2$)$_2$Si(CH$_3$)$_3$, —CON(R$_c$R$_d$)$_2$, —CSN(R$_c$R$_d$)$_2$, —PO(NR$_c$R$_d$)$_2$, and —CH(CH$_3$)OCH$_2$CH$_3$, and P, R$_c$ and R$_d$ are as defined above. The compound of formula V(a) is treated first with an alkyl metal base, for example n-butyllithium, sec-butyllithium, t-butyllithium, or a metal amide base, for example, lithium diisopropylamide; and preferably in the presence of a chelating agent, such as, tetramethylethylenediamine (TMEDA) or hexamethylenephosphoramide (FMPA); then the appropriate benzoate ester of formula IV, where R$_a$ is an alkyl group and R$_1$" is selected as appropriate to obtain the desired product; is added to the reaction mixture to yield the tri-aryl methanol of Formula m. The reaction may be conducted preferably in the presence of an aprotic organic solvent, e.g. tetrahydrofuran, 2-methyltetrahydrofuran, diethylether, or t-butyl methyl ether, and preferably at reduced temperatures, e.g. between −78° C. and room temperature. It is also preferable to conduct the reaction under anhydrous or substantially anhydrous conditions.

(b) Metal Exchange (With a Halogen):

The tri-aryl methanol intermediate of Formula III can be prepared by halogen-metal exchange according to the reaction shown below:

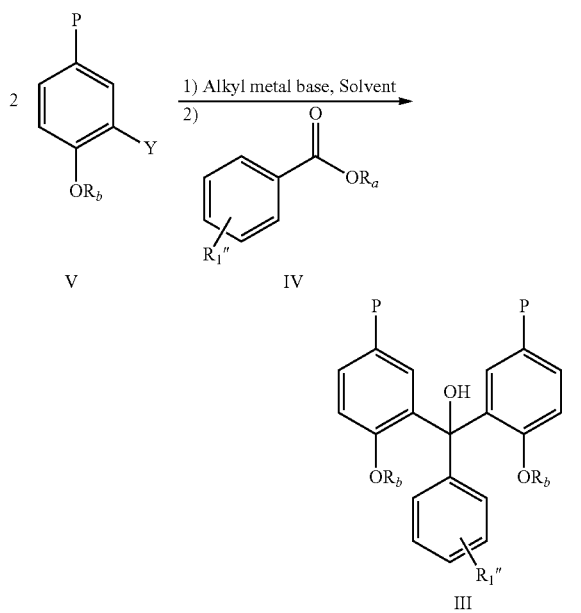

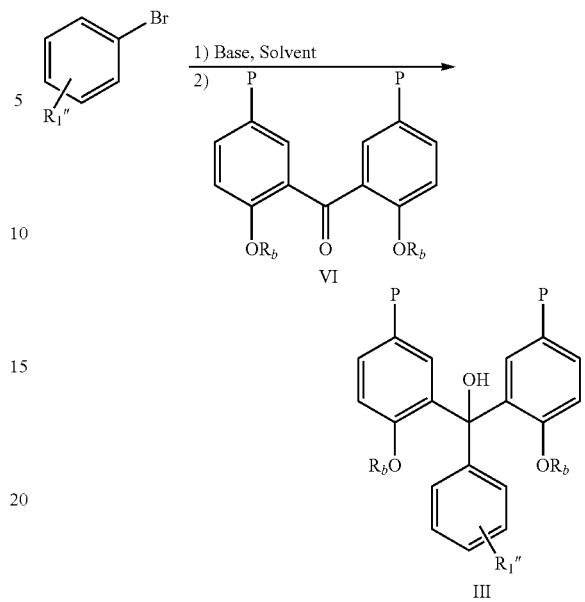

where $R_b$ is —CH$_2$OCH$_3$, —CH$_2$OCH$_2$CH$_3$, —CH(CH$_3$)OCH$_2$CH$_3$, —CH$_2$—OCH$_2$CH$_2$—OCH$_3$, —CH$_2$—OCH$_2$CH$_2$—Si(CH$_3$)$_3$, —CH$_3$, —CH$_2$C$_6$H$_5$, —(CH$_2$)$_2$Si(CH$_3$)$_3$, —CON(R$_c$R$_d$)$_2$, —CSN(R$_c$R$_d$)$_2$, and —PO(NR$_c$R$_d$)$_2$,

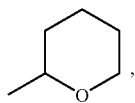

Y is bromo or iodo, and P is as defined above. Two equivalents of the compound of Formula V, wherein Y is as defined above, are treated with an alkyl metal base, for example n-butyllithium; followed by the reaction with approximately one equivalent of the desired compound of Formula IV, wherein R$_a$ is as defined above and R$_1$" is selected as appropriate to obtain the desired product, to provide the corresponding tri-aryl methanol compound of Formula III. The reaction may be conducted preferably in the presence of an aprotic organic solvent; for example, tetrahydrofuran, 2-methyltetrahydrofuran, diethylether, or t-butyl methyl ether, and preferably at reduced temperatures; for example, between −78° C. and room temperature. It is also preferable to conduct the reaction under anhydrous or substantially anhydrous conditions.

(c) Reaction with Di-Aryl Ketone:

The tri-aryl methanol intermediate of Formula II, wherein R$_b$ is —CH$_3$, —CH$_2$C$_6$H$_5$, —CH$_2$OCH$_3$, —CH$_2$OCH$_2$CH$_3$, —CH(CH$_3$)OCH$_2$CH$_3$, —CH$_2$—OCH$_2$CH$_2$—OCH$_3$, —CH$_2$—OCH$_2$CH$_2$—Si(CH$_3$)$_3$, and R$_1$" is selected as appropriate to obtain the desired product, and P is as defined above, can also be prepared according to the reaction shown below by reacting a di-aryl ketone of Formula VI:

First, the bromobenzene is treated with an alkyl metal base, for example n-butyllithium, in an inert organic solvent under anhydrous conditions; followed by a reaction with the compound of Formula VI.

The diarylketone of Formula VI may be conveniently prepared according the reaction shown below:

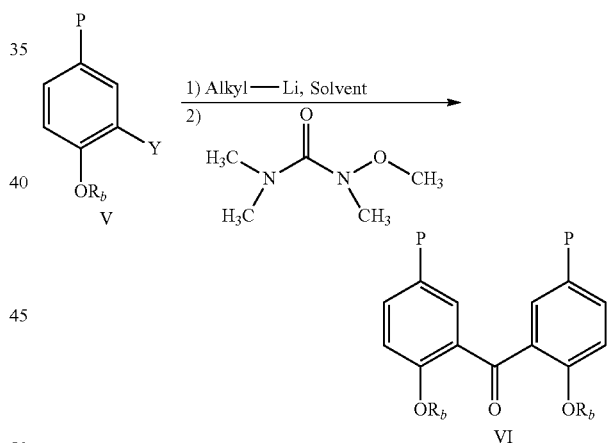

where P and R$_b$ are as defined above. First, the di-protected compound of Formula V, where Y is bromo or iodo, is treated with alkyl lithium base, for example n-butyllithium in an inert organic solvent under anhydrous conditions, followed by reaction with N-methoxy-N,N',N'-trimethylurea so as to yield the compound of Formula VI.

The compounds of Formula III can be used as intermediates in accordance with the examples below, to form compounds of Formula II.

4) Preparation of Compounds of Formula I:

The compound of Formula I wherein R$_1$ is defined above, may be readily obtained by condensation of the aldehyde of Formula II, wherein R$_1$' is as defined above, with two equivalents of 1-amino-5-methyltetrazole, in the presence of an acid, such as p-toluenesulfonic acid monohydrate, methanesulfonic acid, benzenesulfonic acid, 2,4,6-trimethylpyridinium p-toluenesulfonate or pyridinium para-toluenesulfonate, at elevated temperatures, such as from room temperature to 90° C.; in a solvent such as an alcoholic solvent like ethanol, or in 1-methyl-2-pyrrolidinone, dimethyl sulfoxide, or N,N-dimethylformamide:

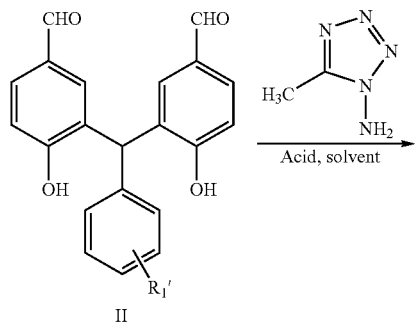

II

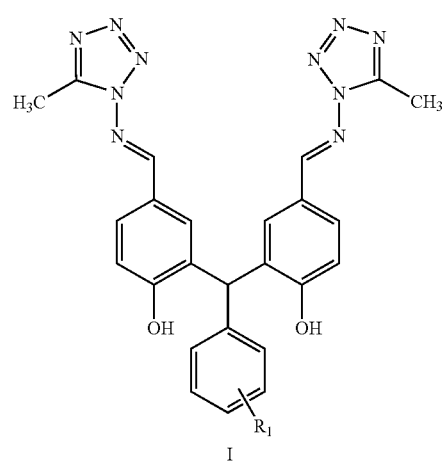

I

The compound of Formula I where $R_1$ is a dialkylamino may be isolated as a salt, for example, a tosic acid salt. The free-base compound is obtained under basic conditions, such as in the presence of sodium bicarbonate, by the reaction shown below:

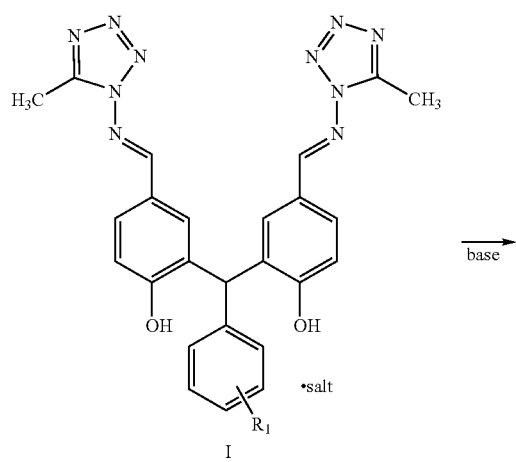

I

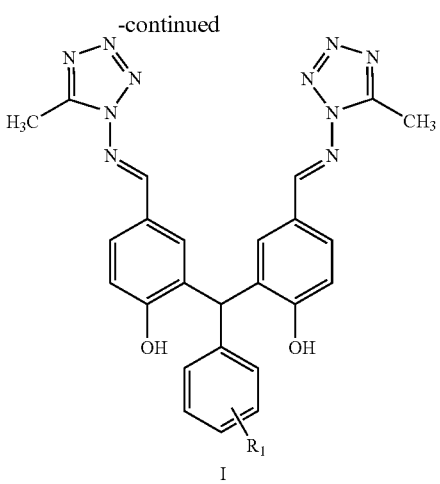

I

The term "alkyl", as used herein, refers to aliphatic hydrocarbon radicals consisting of one to eight carbon atoms, and may be straight or branched. Similarly, the term "alkyl", or any variation thereof, used in combination form to name substituents, such as alkoxy (—O-alkyl), alkylthio (—S-alkyl), alkylamino (—NH-alkyl), hydroxyalkyl (-alkyl-OH), alkoxyalkyl (-alkyl-O-alkyl), or the like, also refers to aliphatic hydrocarbon radicals of one to six carbon atoms, and preferably of one to four carbon atoms. Also "alk" in structural formula denotes an alkyl group, unless divalency is indicated in which case the "alk" denotes the corresponding alkylene group(s).

The term "lower alkyl," as used herein, denotes a $C_1$-$C_4$ alkyl group.

The term "aryl," as used herein, denotes an aromatic hydrocarbon moiety and may be substituted or unsubstituted. An aryl may be selected from but not limited to, the group: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups.

The term "aralkyl," as used herein, is defined as aryl-$C_1$-$C_6$-alkyl-; aralkyl moieties include benzyl, 1-phenylethyl, 2-phenylethyl, 3-phenylpropyl, 2-phenylpropyl and the like.

The term "polyhydroxyalkyl," as used herein, refers to an alkyl radical having two or more hydroxy substituents.

The term "polyfluoroalkyl," as used herein, refers to an alkyl radical having two or more fluoro substituents, but does not include perfluoroalkyl radicals.

The term "dialkylaminoalkyl," as used herein, refers to a radical or substituent of the formula -alkyl-amino-($C_1$-$C_6$-alkyl)($C_1$-$C_6$-alkyl).

The term "amido," as used herein, refers to a radical or substituent of the formula —NRC(=O)R, wherein R independently represents hydrogen or alkyl.

The term "carboxamide," as used herein, refers to a radical or substituent of the formula —C(=O)—N(R)R, wherein R independently represents hydrogen or alkyl.

The term "TBDMS" as used herein refers to a t-butyldimethylsilyl group.

The symbol "Δ" as used herein the schemes denotes heating to an elevated temperature.

The term "hexanes" as used herein refers to a solvent mixture of straight and branched chain hexane hydrocarbons, wherein the solvent mixture contains mostly n-hexane and some minor amounts of branched hexanes.

The abbreviation "Ph," as used herein the schemes and examples, denotes a phenyl group.

The term "oxo," as used herein, in the context of defining a substituent group denotes the oxygen atom of a carbonyl moiety.

The term "chloroform," as used herein, denotes trichloromethane.

Percentage (%) of a solvent shown in the examples is by volume.

Preparation of specific embodiments of anti-pneumovirus compounds within the scope of the invention are exemplified below.

In vitro studies have been performed demonstrating the usefulness of compounds described herein as antiviral agents against pneumoviruses. Antiviral activity was measured on the basis of activity against RSV in a cell culture assay.

All possible isomers of the compounds described herein are within the scope of the present invention. Representative examples of such isomers include, without limitation, cis and trans isomers.

The compounds described herein, their isomers and pharmaceutically acceptable salts exhibit antiviral activity against pneumoviruses and are within the scope of the present invention.

The compounds of the invention can form useful salts with inorganic and organic acids, including, for example, hydrochloric acid, hydrobromic acid, methanesulfonic acid salts, or the like, as well as with inorganic bases, such as sodium or potassium salts.

The pharmaceutically acceptable salts of the compounds of the invention are prepared following procedures which are familiar to those skilled in the art.

The antiviral pharmaceutical compositions of the present invention comprise one or more of the above-described compounds or precursors thereof, as the primary active ingredient in combination with a pharmaceutically acceptable carrier medium and, optionally one or more supplemental active agents.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Twentieth Edition, A. R. Gennaro (William and Wilkins, Baltimore, Md., 2000) discloses various carriers used in formulating pharmaceutical compositions and known techniques for the preparation thereof. Except insofar as any conventional carrier medium is incompatible with the antiviral compounds of the invention, such as by producing any undesirable biological effect or otherwise interacting in a deleterious manner with any other component(s) of the pharmaceutical composition, its use is contemplated to be within the scope of this invention.

The compounds of the invention, any precursors thereof and their isomers and pharmaceutically acceptable salts are also useful in treating and preventing pneumovirus infections and diseases when used in combination with supplemental active agents, which may be optionally incorporated into the pharmaceutical composition of the invention, or otherwise administered during a course of therapy. These include, without limitation, interferons, ribavirin, and immunomodulators, immunoglobulins, anti-inflammatory agents, antibiotics, anti-virals, anti-infectives, and the like, the combination of which with one or more compounds of the invention offers additive or synergistic therapeutic benefit.

In the pharmaceutical compositions of the invention, the active agent may be present in any therapeutically effective amount, which is typically at least 0.1% and generally not more than 90% by weight, based on the total weight of the composition, including carrier medium and/or supplemental active agent(s), if any. Preferably, the proportion of active agent varies between 1-50% by weight of the composition.

Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers or excipients for medicaments may all be suitable as carrier media.

Compounds of the invention are useful in treating and preventing pneumovirus infections (and diseases) in humans, as well as in livestock, and may be used to treat cattle, swine and sheep, or to treat avian species such as turkeys, or for other animals susceptible to pneumovirus infection. Thus, the term "patient" as used herein includes, without limitation, all of the foregoing.

Compounds described herein are also useful in preventing or resolving pneumoviral infections in cell cultures, tissue cultures and organ cultures, as well as other in vitro applications. For example, inclusion of compounds of the invention as a supplement in cell or tissue culture growth media and cell or tissue culture components will prevent pneumoviral infections of cultures not previously infected with pneumoviruses. Compounds described above may also be used to eliminate pneumoviruses from cultures or other materials infected or contaminated with pneumoviruses, after a suitable treatment period, under any number of treatment conditions as determined by the skilled artisan.

The compounds of the invention may be administered using any amount and any route of administration effective for attenuating infectivity of the pneumovirus. Thus, the expression "amount effective to attenuate infectivity of pneumovirus," as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like.

The compounds of the invention may be administered as an inhaled aerosol. The aerosol may be prepared and administered using an electrohydrodynamic device (EHD). Preferred pharmaceutical formulations of the compound of Formula I for use in an EHD device are ethanol solutions. A preferred feature of the invention is a pharmaceutical composition that contains at least 50% ethanol (by volume). Other preferred features of the invention include pharmaceutical compositions containing at least 60% ethanol, at least 70% ethanol, at least 80% ethanol or at least 90% ethanol (by volume). Other features of the invention include a pharmaceutical formulation comprising water and ethanol and a pharmaceutical formulation comprising propylene glycol and water. A preferred feature of the invention is a pharmaceutical composition comprising ethanol, propylene glycol, and water. Another preferred feature of the invention is a pharmaceutical formulation comprising at least 90% ethanol and less than 5% water (by volume). An ultimately preferred feature of the invention is the pharmaceutical composition comprising about 85% ethanol, about 10% propylene glycol, and about 5% water (by volume). NaCl (in the form of a standard saline solution) may be used to adjust the solution resistivity in an EHD device.

Other acceptable excipients that may be used in pharmaceutical formulations of Formula I for use in an EHD device are glycerol, dextrose, and lecithin. An example for preparing a pharmaceutical composition for use in an EHD device is as follows:

1. Dispense the quantities of Ethyl Alcohol, USP and Propylene Glycol, USP into a clean 1 L glass bottle.
2. Stir solution from Step 1 for 5 minutes.
3. Add quantity of compound of Formula I to solution from Step 2.
4. Stir solution from Step 3 for a minimum of 2 hours at a temperature ranging from room temperature to 60° C., preferably from 50-60° C., until complete dissolution of the compound.
5. Adjust resistivity of solution with 0.9% Sodium Chloride for Injection, USP.
6. Filter bulk solution using a 0.2μ filter.
7. Fill and seal the cartridges for use in the EHID device (target fill volume 3 mL±0.1 mL)
8. Visually inspect each cartridge.
9. Label each cartridge.

The anti-pneumovirus compounds are preferably formulated in dosage unit form for ease of administration and uniformity of dosage. Dosage unit form as used herein refers to a physically discrete unit of antiviral agent appropriate for the patient to be treated. Each dosage should contain the quantity of active material calculated to produce the desired therapeutic effect either as such, or in association with the selected pharmaceutical carrier medium. Typically, the antiviral compounds of the invention will be administered in dosage units containing from about 0.1 μg to about 50 mg of the antiviral agent, with a range of about 0.001 mg to about 25 mg being preferred.

The compounds of the invention, including their isomers and pharmaceutically acceptable salts, may be administered as such, or in the form of a precursor from which the active agent can be derived, such as a prodrug. A prodrug is a derivative of a compound described herein, the pharmacologic action of which results from the conversion by chemical or metabolic processes in vivo. Prodrugs of the compounds of the invention may include, but are not limited to mono-, di- or tri-esters of simple or functionalized aliphatic carboxylic acids; esters of carbamic acids ($R_e$—(O—CO—$NR_fR_g)_s$); esters of amino acids ($R_e$—(O—CO—CH($NH_2$)$R_f)_s$); esters of unsubstituted or substituted aromatic acids ($R_e$—(O—CO-aryl$)_s$), wherein the aryl ring may be substituted with hydroxy, carboxy, alkyl, alkylthio, alkylsulphinyl, alkylsulphonyl, phosphoric acid, amino, alkylamido and halogen groups; esters of derivatized phosphoric acids; (acyloxy)methyl or acyloxy(ethyl)ethers ($R_e$—(O—$CH_2$—O—CO—$R_f)_s$ or $R_e$—(O—CH($CH_3$)—O—CO—$R_f)_s$); (alkoxycarbonyloxy)methyl or (alkoxycarbonyloxy)ethyl ethers ($R_e$—(O—$CH_2$—O—CO—O—$R_f)_s$); and O-glycosides, wherein $R_e$ is a residue of a compound of the invention, $R_f$ and $R_g$ are aliphatic radicals ($C_1$-$C_{10}$) and s is an integer from 1 to 3. Such prodrugs may be prepared according to procedures well known in the field of medicinal chemistry and pharmaceutical formulation science and are within the scope of the present invention.

The compounds of the invention may be administered orally, parenterally, such as by intramuscular injection, intraperitoneal injection, intravenous infusion or the like, or by inhalation, such as by aerosol, in the form of a solution or a dry powder, or the like, or by intubation, depending on the nature and severity of the infection being treated. The compounds of the invention may be administered orally, parenterally, or by inhalation or intubation at dosage levels of about $10^{-6}$ mg to about 1000 mg/kg, one or more times a day, to obtain the desired therapeutic effect.

The compounds of the invention will typically be administered from 1 to 4 times a day so as to deliver the above-mentioned daily dosage. However, the exact regimen for administration of the compounds and compositions described herein will necessarily be dependent on the needs of the individual host being treated, the type of treatment administered and the judgment of the attending physician, veterinarian or medical specialist.

In view of the inhibitory effect on pneumovirus replication in cell culture produced by the compounds used in the method of the invention, it is anticipated that these compounds will be useful not only for therapeutic treatment of pneumovirus infection, but for pneumovirus prophylaxis, as well. The dosages will be essentially the same, whether for treatment or prophylaxis of pneumovirus infection.

The following examples are provided to describe the invention in further detail. These examples, which set forth the preferred mode presently contemplated for carrying out the invention, are intended to illustrate and not to limit the invention.

Examples 1-44 illustrate the chemical synthesis of representative compounds of the invention.

Example 1

Preparation of 2,2'-[[3-(2,2,2-Trifluoroethyl)phenyl]methylene]bis[4-[[(5-methyl-1H-tetrazol-1-yl)imino]methyl]]phenol a. Preparation of 4-Methoxymethoxybenzaldehyde. A solution of 4-hydroxybenzaldehyde (118.20 g, 0.968 mol) in dichloromethane (1.1 L) was stirred mechanically and cooled to 0° C., under argon. N,N-diisopropylethylarnine (337.2 ml) was added to the reaction, and the mixture was stirred until homogenous. Chloromethyl methyl ether (101.30 g, 1.94 mol) was added dropwise, maintaining reaction temperature below 10° C. After the addition, the solution was warmed to room temperature, then stirred for 1 hour. The reaction was quenched with water (500 ml), and the aqueous phase was separated from the organic phase. The organic layer was washed with water, 5% glacial acetic acid, and saturated aqueous NaCl. The solution was dried with sodium sulfate, filtered, and rotary evaporated, yielding 170 g of pure product.

b. Preparation of 2-(4-Methoxymethoxyphenyl)-5,5-dimethyl-1,3-dioxane. A solution of 4-methoxymethoxybenzaldehyde, neopentyl glycol (10.3 g, 98.9 mmol), pyridinium para-toluenesulfonate (1.0 g, 3.98 mmol), and benzene (500 ml) was refluxed with azeotropic removal of water for several hours, under argon. The cooled reaction mixture was quenched with 2 ml of triethylamine, and concentrated on rotary evaporator. The product was chromatographed (silica gel, 5% ethyl acetate in hexanes), yielding about 14.83 g of the product.

c. Preparation of:

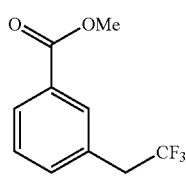

1(c)

A mixture of methyl 3-(bromomethyl)benzoate (3.0 g, 13.1 mmol), methyl 2-chloro-2,2-difluoroacetate (3.79 g, 26.2 mmol), potassium fluoride (0.75 g, 13.1 mmol), copper iodide (2.49 g, 13.1 mmol), and N,N-dimethylformamide (27 ml) was heated to 120° C. for 7 hours. The reaction mixture was slowly cooled to room temperature and filtered. The filtrate was diluted with ethyl ether and water, again filtered, and the layers were separated. The aqueous layer was extracted with ether, and the combined organics were washed with saturated aqueous NaCl, dried ($MgSO_4$), and concentrated in vacuo. The crude product was purified via column chromatography (silica gel, 10% ethyl acetate in hexanes), providing 1.82 g of the desired product (1c).

d. Preparation of:

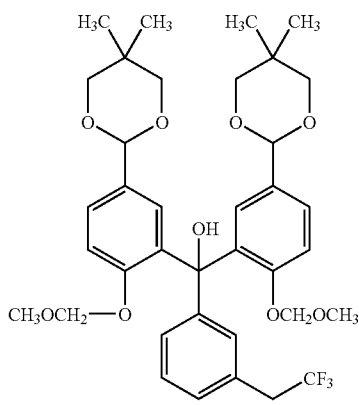

1(d)

2-(4-Methoxymethoxyphenyl)-5,5-dimethyl-1,3-dioxane (3.47 g, 13.8 mmol), prepared according to step b, above, was mixed with dry tetrahydrofuran (45 ml), under argon. N,N, N',N'-Tetramethylethylenediamine (2.1 ml, 13.8 mmol) was added to the solution, and the resulting mixture was cooled to around 0° C. in an ice/NaCl bath. Sec-butyllithium (11.6 ml, 1.3M in cyclohexane, 15.1 mmol) was added over 10 minutes. The reaction was stirred for 15 minutes at 0° C., and then a solution of compound 1(c) (1.0 g, 4.6 mmol) in dry tetrahydrofuran (15 ml) was added dropwise to the reaction. After this addition, the solution was stirred for 2.5 hours at 0° C., then slowly warmed to room temperature for two hours. The reaction was quenched with 20% aqueous $NH_4Cl$, and the organic solvents were removed in vacuo. The mixture was extracted two times with ethyl acetate (45 ml). The organic layers were combined, dried with magnesium sulfate, filtered, and concentrated on rotary evaporator. The crude product was chromatographed (silica gel (100 g), 20% ethyl acetate in hexanes), yielding 1.20 g of the desired product.

e. Preparation of:

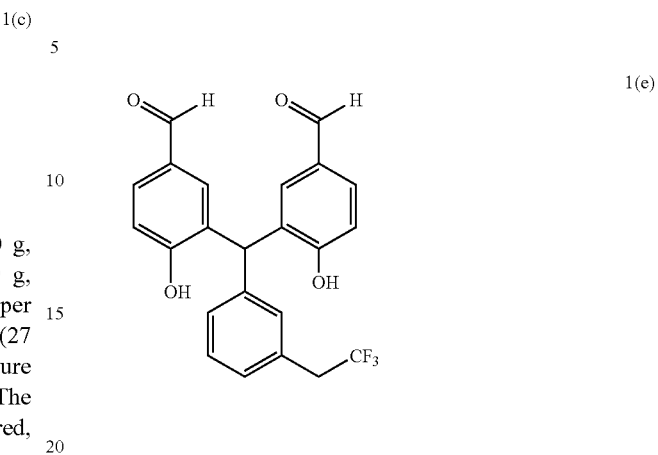

1(e)

Hydriodic acid (0.72 ml, 58 wt % in water) was added to a solution of compound 1(d) (0.50 g, 0.72 mmol) in glacial acetic acid (7.2 ml). The reaction was stirred at room temperature for 45 minutes. The reaction mixture was poured 10% sodium bisulfite and ethyl acetate. The mixture was washed with additional 10% sodium bisulfite (2×50 ml), dried over magnesium sulfate, filtered, and rotary evaporated. The resulting solid was recrystallized in ethyl acetate/hexanes, yielding 0.181 g of the desired product.

f. 2,2'-[[3-(2,2,2-Trifluoroethyl)phenyl]methylene]bis[4-[[(5-methyl-1H-tetrazol-1-yl)imino]methyl]]phenol. Compound 1(e) (0.10 g, 0.24 mmol) was dissolved in 2.5 ml absolute ethanol, and added dropwise to a refluxing solution of 1-amino-5-methyltetrazole (71 mg, 0.72 mmol) and pyridinium para-toluenesulfonate (6 mg, 0.024 mmol) in 2.5 ml ethanol. The reaction was heated to reflux for 1 hour, and then cooled to room temperature. A solid was collected by filtration and dried under vacuum, yielding about 0.1 g of crude product. The solid was recrystallized in hot ethanol to provide 30 mg of the title compound.

Example 2

Preparation of 3-[[Bis[[5-(5-methyl-1H-tetrazol-1-yl)imino]methyl]-2-hydroxyphenyl]methylene]benzeneethanol, acetate ester a. Preparation of N-methoxy-N,N',N'-trimethylurea. A mixture of dimethylhydroxylamine hydrochloride (150.0 g, 1.54 mol), 4-dimethylaminopyridine (9.4 g, 0.076 mol), and dichloromethane (1.35 L) was chilled to −20° C., under argon. Dimethylcarbamyl chloride (135 ml, 1.46 mol) and pyridine (315 ml) were added consecutively over 25 minutes. The reaction was slowly warmed to room temperature over 2 hours, and agitated for about 16 hours. The reaction mixture was filtered to remove pyridine hydrochloride, and concentrated by rotary evaporator. The mixture was diluted with t-butyl methyl ether (500 ml), and the solids were removed by filtration. The filtrate was concentrated by rotary evaporation. Vacuum distillation provided the desired product (135.10 g, 69%) as a colorless oil.

b. Preparation of:

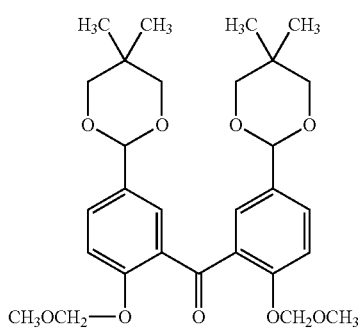

2(b)

A mixture of compound 1(b) (62.7 g, 189.3 mmol) and t-butyl methyl ether (400 ml) was cooled to −20° C. n-Butyllithium (130 ml, 208.0 mmol, 1.6M in hexanes) was added slowly. After 10 minutes, a solution of N-methoxy-N,N',N'-trimethylurea (11.0 g, 83.2 mmol) in t-butyl methyl ether (115 ml) was added dropwise. The mixture was stirred at −20° C. for 1.5 hours and at 0° C. overnight. The reaction mixture was quenched with saturated aqueous NH$_4$Cl (125 ml), and the layers were separated. The combined organic phases were washed with water (200 ml) and brine (200 ml), and concentrated in vacuo. The orange oil was purified via several chromatography columns (silica gel, ethyl acetate/hexanes), followed by a crystallization in ethanol/water, providing the desired product (30.22 g).

c. Preparation of:

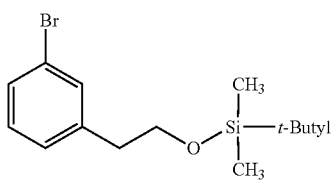

2(c)

3-Bromophenethyl alcohol (5.18 g, 25.8 mmol) was mixed with tert-butyldimethylsilyl chloride (4.24 g, 28.16 mmol), imidazole (1.91 g, 28.16 mmol), and N,N-methylformamide (15 mil), and stirred at room temperature for about 16 hours. The product was partitioned between ethyl acetate and water. The aqueous layer was washed with ethyl acetate, and the organics were combined, washed with brine, dried over MgSO$_4$, and filtered. The filtrate was concentrated in vacuo to provide 8.07 g of the desired product.

d. Preparation of:

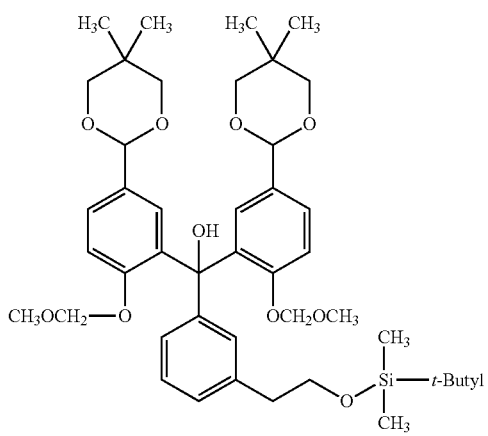

2(d)

A solution of compound 2(c) (3.27 g, 10.36 mmol) in anhydrous tetrahydrofuran was cooled to −78° C., under argon. n-Butyllithium (3.76 ml of 2.5M) was added slowly. After 5 minutes, a solution of compound 2(b) (5.00 g, 9.42 mmol) in tetrahydrofuran (40 ml) was added dropwise. The mixture was slowly warmed to room temperature, stirred overnight, and quenched with 10% NH$_4$Cl (1 L). The solution was extracted with ethyl acetate (2×60 ml). The combined organic phases were washed with brine, dried (MgSO$_4$), filtered and concentrated in vacuo. The crude product was purified via flash chromatography (silica gel, 30% ethyl acetate in hexanes), providing 3.13 g of the desired product.

e. Preparation of:

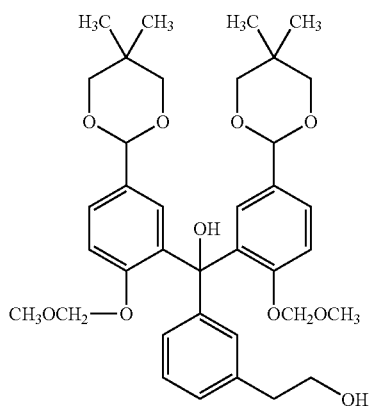

2(e)

Tetrabutylammonium fluoride (4.5 ml, 1.0M in tetrahydrofuran) was added to a solution of compound 2(d) (3.13 g, 4.08 mmol) in tetrahydrofuran (15 ml). The reaction mixture was stirred at room temperature, under argon, overnight. The solution was partitioned between ethyl acetate and water, and the layers were separated. The aqueous layer was extracted with ethyl acetate (2×50 ml), and the combined organics were washed with brine, dried (MgSO$_4$), filtered, and concentrated in vacuo. The crude product was purified via dry-flash chromatography (silica gel, 10% ethyl acetate in hexanes), providing 2.02 g of the desired product.

f. Preparation of:

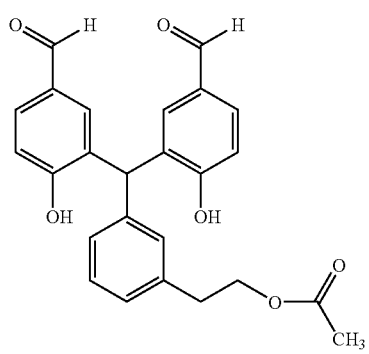

2(f)

Hydriodic acid (1.53 ml, 56 wt % in water) was added to a solution of compound 2(e) (1.00 g, 1.53 mmol) in glacial acetic acid (5 ml). The reaction was stirred at room temperature for 2.5 hours, diluted with water, and extracted with ethyl acetate (2×). The organic layers were combined and washed with ice water (3×50 ml), saturated aqueous NaHSO$_3$ (2×50 ml), and brine (1×30 ml). The solution was dried over magnesium sulfate, filtered, and rotary evaporated. The crude product was purified via flash chromatography (silica gel, 40% hexanes in ethyl acetate), providing 0.47 g (81%) of the desired product.

g. 3-[[Bis[[5-(5-methyl-1H-tetrazol-1-yl)imino]methyl]-2-hydroxyphenyl]methylene]benzeneethanol, acetate ester. Compound 2(f) (70 mg, 0.167 mmol) was dissolved in ethanol and added dropwise to a refluxing solution of 1-amino-5-methyltetrazole (49.7 mg, 0.501 mmol) and pyridinium para-toluenesulfonate (4 mg, 0.017 mmol) in ethanol. The reaction was heated to reflux for 2 hours, and then cooled to room temperature. The mixture was concentrated in vacuo, and recrystallized from hot ethanol to give 60 mg of the title compound as a yellow solid.

Example 3

Preparation of 3-[[Bis[[5-(5-methyl-1H-tetrazol-1-yl)imino]methyl]-2-hydroxyphenyl]methylene]benzeneethanol a. 3-Bromophenyl ethanol. A 12 L flask was inerted with argon. To the flask was charged (3-bromo-phenyl)-acetic acid (450.0 g, 2.09 mol) and methyl-t-butyl ether (3.0 L) with overhead agitation. A hazy solution was obtained, and borane-tetrahydrofuran complex (2.4 L, 1M) was added over 2.5 hours. The mixture was agitated for 2 hours and allowed to cool to 20° C. After completion of the reaction, the mixture was slowly charged with water (250 ml), followed by 1N NaOH (500 ml). The agitation was discontinued, and the mixture was allowed to settle. The layers were separated, and the product layer was washed with 1N NaOH (500 ml) and water (1000 ml). The product layer was concentrated by rotary evaporation to provide 414.0 (98%) of the product as a yellow oil.

b. 1-Bromo-3-(2-methoxyethyl)-benzene. A 12 L flask was inerted with argon. To the flask was charged sodium hydride (102.6 g, 60% dispersion in water, 2.57 mol) and tetrahydrofuran (1.9 L) with overhead stirring. The mixture was warmed to 40° C. and 1-bromo-3-(2-methoxyethyl)-benzene (396.7 g, 1.97 mol) was added over 1.5 hours. The mixture was agitated for an additional 1.5 hours at 40-45° C. The mixture was cooled to 10° C., and methyl iodide (182.0 ml, 2.92 mol) was added over 1 hour. The mixture was then allowed to warm to room temperature and agitation was continued overnight.

Ammonium hydroxide (200 ml) was slowly added to the mixture. The mixture was agitated for 1 hour, then water (1 L) and ethyl acetate (1.3 L) were added. The agitation was continued for 10 minutes. The agitation was stopped, and the mixture was allowed to settle. The layers were separated, and the upper organic layer was washed with water (2×400 ml). The organic layer was concentrated by rotary evaporation, and 390 g (92%) of the desired product was isolated via a short path vacuum distillation.

c. Preparation of:

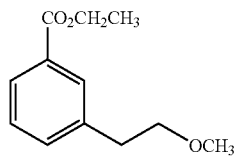

3(c)

1-Bromo-3-(2-methoxyethyl)benzene (579.8 g, 2.70 mol) and tetrahydrofuran (1.1 L) were added to a 2 L flask inerted with argon. The mixture was agitated until a homogenous solution had formed. Magnesium 50-mesh powder (65.6 g, 2.70 mol) and tetrahydrofuran (235 ml) were added to a 5 L flask inerted with argon. A portion of the first solution (30 ml) was added to the mixture in the 5 L flask, and the reaction mixture was heated to reflux. After the reaction had initiated, heating was discontinued, and the remaining solution from the 1 L flask was added to the 5 L flask at such a rate that reflux was maintained. After this addition was complete, the mixture was cooled to room temperature. The agitation was discontinued, and the mixture was allowed to settle.

Diethylcarbonate (1.3 L, 10.81 mol) and methyl-t-butyl ether (1.3 L) were added to a 12 L flask, inerted with argon. The resulting solution was cooled to 0° C., and the above Grignard was slowly added via cannula with vigorous agitation. After the addition was complete, the remaining sludge was poured into the diethylcarbonate solution. The reaction was agitated for 0.5 hours and quenched with 1N HCl (1.0 L). The mixture was cooled to room temperature, and saturated aqueous sodium chloride solution (1.0 L) was added. The agitation was continued for 10 minutes, then the mixture was allowed to settle. The layers were separated, and the upper organic layer was concentrated. The crude product was purified via a short path distillation to provide 428.5 g (76%) of the desired product.

d. Preparation of:

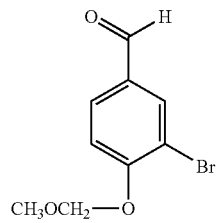

3(d)

Celite (1200.00 g) was added to a flask containing dichloromethane (9.00 L) with agitation. Phosphorus pentoxide (1200.0 g, 8.51 mol) was then added quickly with agitation. The mixture was cooled to 20° C. A separate mixture of dimethoxymethane (12.0 L) and 3-bromo-4-hydroxybenzaldehyde (1200.00 g 5.97 mol) was agitated, warmed to 30° C. until homogenous, then cooled to room temperature. This solution was added to the first mixture over a 1-hour period. The reaction mixture was warmed to room temperature and agitated for an additional 3 hours. The reaction mixture was then added to a chilled (−10° C.) solution of 12M NaOH (2.57 L) in water (18.00 L). This mixture was agitated, then the layers were allowed to separate. The organic layer was washed with water (6.00 L) and concentrated in vacuo. The product was crystallized from ethanol, and filtered out at −10° C. to provide 772.30 g of desired product. A second crop of crystals provided 195.00 g of the desired product.

e. Preparation of:

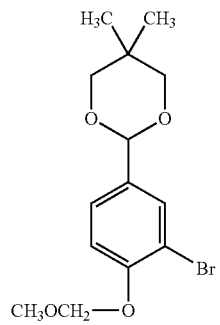

3(e)

A solution of compound 3(d) (1464.00 g, 5.98 mol), neopentyl glycol (809.44 g, 7.77 mol), 2,4,6-trimethylpyridinium p-toluenesulfonate (56.90 g, 0.19 mol), and cyclohexane (14.0 L) was refluxed with azeotropic removal of water for several hours, under argon. The cooled reaction mixture was quenched with 0.5N NaOH (3.59 L). The layers were allowed to separate, and the organic layer was washed with water (1.79 L). The solvent was removed in vacuo, and the product was crystallized from ethyl acetate (0.39 L) and hexanes (3.94 L). The crystals were collected at –10° C. and dried at room temperature to provide 1331.12 g of desired product. A second crop of crystals provided 330.00 g of the desired product.

f. Preparation of:

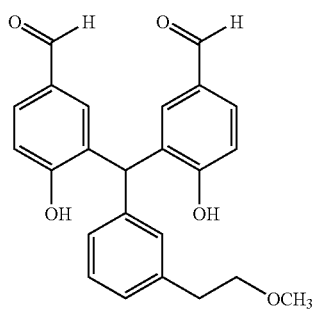

3(f)

To a 50 L reactor was charged compound 3(e) (1714.9 g, 5.18 mol). The reactor was inerted with nitrogen, and methyl t-butyl ether (13.3 kg) was added with agitation. The resulting solution was cooled to –10° C., and n-butyllithium (332 g, 1.6M in hexanes) was charged over 1 hour. A suspension formed during the addition, and the mixture was agitated for 45 minutes. A solution of compound 3(c) (500.0 g, 5.18 mol) was dissolved and diluted to 3.5 L with methyl t-butyl ether over ½ hour. The reaction was agitated for 1½ hour while allowing the temperature to rise to 8° C.

The reaction was quenched with ammonium chloride (570 g), dissolved, and diluted to 3.5 L with water. The mixture was agitated for 10 minutes, allowed to settle for 10 minutes, and the layers were separated. The upper organic layer was washed with water (3.5 L), repeating the previous separation. The aqueous layers were discarded. The organic layer was concentrated by distillation to an oil (30 to 50° C.; 15 to 24 inches Hg vacuum; 22 L distillate). Glacial acetic acid (2.87 L) was added to the hot solution, and the mixture was cooled to ambient temperature. The resulting solution was drained from the reactor and retained for the next step.

To a 22 L flask was charged hydriodic acid (2.73 L, 57 wt %) and glacial acetic acid (2.68 L). The mixture was cooled to 15° C., and the above-prepared solution was charged slowly through an addition funnel over ½ hour. The mixture was agitated for 1 hour at ambient temperature and transferred to the 50 L reactor. To the acid solution was charged 760 g of sodium bicarbonate dissolved and diluted to 3.5 L with water followed by 34.5 L water. The resulting suspension was agitated overnight at ambient temperature. The crude product was collected by vacuum filtration, washed with water, and air dried for two days.

To a 3 L flask was charged 677.0 g of the crude product and ethyl acetate (0.85 L). A suspension formed, and the mixture was heated to 65° C. for ½ hour. The mixture was cooled to 0° C. The resulting product was collected by vacuum filtration and washed with 0° C. ethyl acetate until the filtrate came through the filter cake colorless. The product was dried in a vacuum oven (35° C. 20-25 inches Hg vacuum) to provide 458.0 g of the desired product as a gray solid.

g. Preparation of:

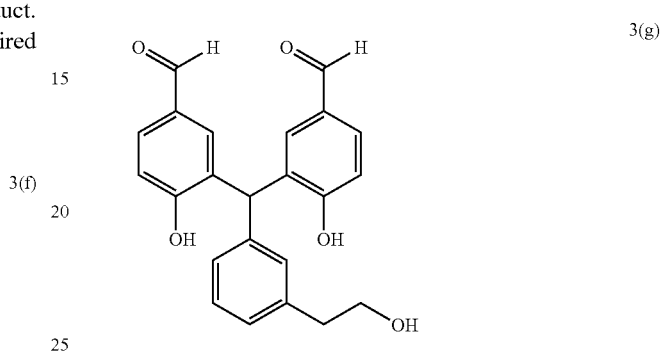

3(g)

D,L-Methionine (191.09 g, 1.28 mol) was added to a flask containing rapidly stirring methanesulfonic acid (1.00 L), under argon. When the reaction temperature returned to room temperature, compound 3(f) was added. The reaction mixture was stirred at room temperature for 3.5 hours. The reaction was quenched by adding ice (1 kg) followed by water (600 ml). The mixture was cooled in an ice-bath to below 20° C., and the solid was removed by filtration. The solid was rinsed with water and air-dried.

The isolated solid was dissolved in a mixture of tetrahydrofuran (600 ml) and water (400 ml). Ethyl acetate (600 ml) and saturated aqueous sodium chloride solution (600 ml) were mixed with the solution. The layers were separated, and the aqueous/sodium chloride phase was rinsed with additional ethyl acetate (400 ml). The organic phases were combined and washed with 50% saturated aqueous sodium chloride (2×500 ml), followed by a wash with saturated aqueous sodium chloride solution. The organic layer was concentrated in vacuo to provide an oil. The product was crystallized in t-butyl methyl ether to provide 53.53 g of the desired product as a pale yellow solid.

h. 3-[[Bis[[5-(5-methyl-1H-tetrazol-1-yl)imino]methyl]-2-hydroxyphenyl]methylene]benzeneethanol. Compound 3(g) (100.00 g, 0.268 mol) was dissolved in absolute ethanol (1700 ml) at 40° C. This solution was quickly added, over 45 minutes, to a solution of 1-amino-5-methyltetrazole (79.70 g, 0.804 mol), 2,4,6-trimethylpyridinium p-toluenesulfonate (7.86 g, 0.0268 mol), and absolute ethanol (500 ml). The reaction mixture was allowed to stir at a gentle reflux for 2 hours. A portion of the ethanol (1000 ml) was distilled away, and the remaining solution was cooled to room temperature and stirred overnight. The solution was cooled to 7° C. in an ice/water bath, and an off-white solid was isolated via filtration. The solid was rinsed with chilled ethyl acetate (2×150 ml) and t-butyl methyl ether and air dried to provide 135.15 g of the title product.

Example 4

Preparation of 2,2'-[[3-(4-Morpholinyl)phenyl]methylene]bis[4-[[(5-methyl-1H-tetrazol-1-yl)imino]methyl]]phenol a. Preparation of:

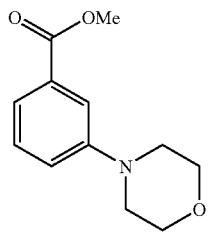

4(a)

A Schlenk flask containing methyl 3-bromobenzoate (2.00 g, 9.8 mmol), tris(dibenzylideneacetone)dipalladium(0) (0.090 g, 0.098 mmol), (S)-binaphthol (0.092 g, 0.147 mmol), and cesium carbonate (4.50 g, 13.8 mmol) was evacuated by vacuum and filled with argon. Morpholine (1.04 ml, 11.8 mmol) and toluene (24 ml) were added to the flask. The reaction vessel was closed and heated to 100° C. overnight. Upon completion of the reaction, the mixture was cooled to room temperature and diluted with ether. The mixture was washed with water and brine, dried (MgSO$_4$), filtered, and concentrated in vacuo. The crude product was purified via column chromatography (silica gel, 25% ethyl acetate in hexanes) to provide 1.90 g (90%) of pure product.

b. 2,2'-[[3-(4Morpholinyl)phenyl]methylene]bis[4-[[(5-methyl-1H-tetrazol-1-yl)imino]methyl]]phenol. The title compound (0.42 g) was prepared essentially according to the basic procedure described in steps d-f Example 1, above; however, compound 4(a) was used in step d instead of compound 1(c).

Example 5

Preparation of 2,2'-[[3-(1-Piperidinyl)phenyl]methylene]bis[4-[[(5-methyl-1H-tetrazol-1-yl)imino]methyl]]phenol a. Preparation of:

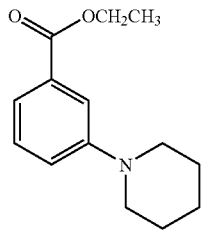

5(a)

A solution of ethyl 3-aminobenzoate (5.00 ml, 33.5 mmol), 1,5-dibromopentane (7.70 g, 33.5 mmol), and N,N-diisopropylethylamine (10.39 g, 80.4 mmol) in toluene (10 ml) was slowly added by an addition funnel to a flask containing refluxing toluene (150 ml). Since no reaction occurred after one hour, potassium iodide (100 mg) was added. The reaction was refluxed for about 64 hours. The layers were partitioned after adding water (100 ml), saturated NaCl (50 ml), and t-butyl methyl ether (100 ml). The organic layer was washed with saturated aqueous NaCl and dried with MgSO$_4$. The crude product was filtered, concentrated in vacuo, and purified via column chromatography (silica gel, 47.5% dichloromethane, 47.5% hexanes, and 5% ethyl acetate) to provide 5.68 g of the desired product.

b. Preparation of:

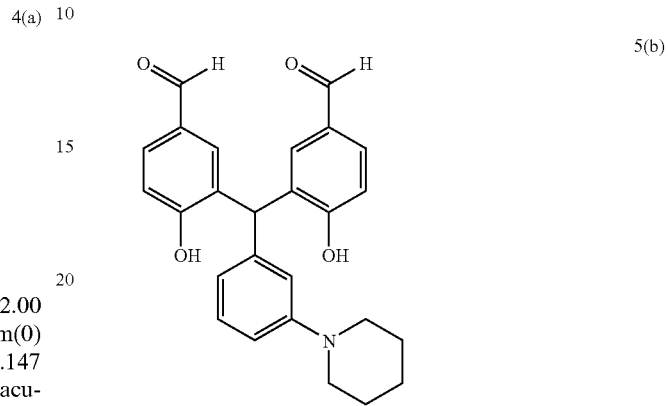

5(b)

The intermediate compound was prepared essentially according to the basic procedure described in steps d-e Example 1, above; however, compound 5(a) was used in step d instead of compound 1(c).

c. 2,2'-[[3-(1-Piperidinyl)phenyl]methylene]bis[4-[[(5-methyl-1H-tetrazol-1-yl)imino]methyl]]phenol. Compound 5(b) (3.00 g, 7.22 mmol) was dissolved in absolute ethanol (94 ml), and added dropwise to a refluxing solution of 1-amino-5-methyltetrazole (2.15 g, 21.7 mmol) and pyridinium para-toluenesulfonate (2.00 g, 7.94 mmol) in ethanol (94 ml). The reaction was heated to reflux for 2 hours, and then cooled to room temperature. The mixture was diluted t-butyl methyl ether (about 700 ml), and the tosic acid salt of the product was collected by filtration. The free base was isolated by first treating the salt in ethyl acetate and water with sodium bicarbonate, then washing the organics with McIlvans pH 5 buffer. The organic layer was dried with MgSO$_4$, filtered, and concentrated to provide 2.50 g of the title compound.

Example 6

Preparation of 3-[[Bis[[5-(5-methyl-1H-tetrazol-1-yl)imino]methyl]-2-hydroxyphenyl]methylene]-N,N-bis(methoxyethyl)benzenesulfonamide a. Preparation of:

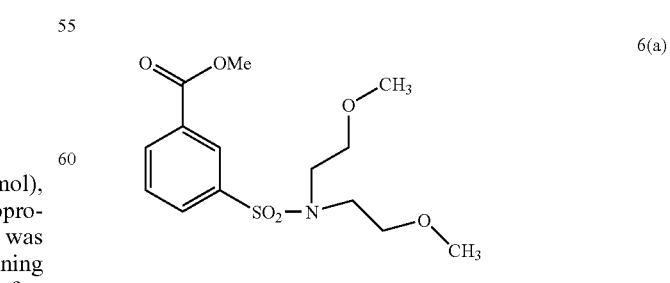

6(a)

A solution of 3-chlorosulfonyl benzoic acid (5.00 g, 22.7 mmol) in toluene was added dropwise over 30 minutes to a solution of triethylamine (5 ml) and bis-(2-methoxyethyl)amine (10.0 ml, 67.7 mmol) in toluene (35 ml). The mixture was heated to reflux for 24 hours. The solvent was removed by rotary evaporation. Methanol was added, and the remaining volatiles were co-evaporated (3×). Dry methanol and thionyl chloride (2 ml) were added, and the reaction was stirred for 72 hours. The product was isolated after an aqueous work-up and purification via flash chromatography (silica gel, 50% ethyl acetate in hexanes).

b. The title compound (0.43 g, yellow solid) was prepared essentially according to the basic procedure described in steps d-f of Example 1, above; however, compound 6(a) was used in step d instead of compound 1(c).

Example 7

Preparation of 3-[[Bis[[5-(5-methyl-1H-tetrazol-1-yl)imino]methyl]-2-hydroxyphenyl]methylene]-N-(hydroxyethyl)-N-methylbenzenesulfonamide a. Preparation of:

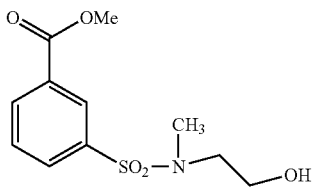

7(a)

3-(Chlorosulfonyl)benzoic acid (5.00 g, 22.7 mmol) was dissolved in tetrahydrofuran (30 ml) and added dropwise over 40 minutes to a solution of N-methyl ethanolamine (5.00 ml, 62.2 mmol), triethylamine (3 ml), and tetrahydrofuran (30 ml). The reaction was stirred at room temperature overnight. The solvent was removed by rotary evaporation, diluted with ethyl acetate and washed with 1N HCl. The organic layer was concentrated by rotary evaporation and dried in vacuo to provide the crude acid, which was taken on to the next step without further purification.

Thionyl chloride (2 ml) was added dropwise to a solution of the crude acid, from above, in methanol (100 ml). The reaction was stirred at room temperature for 72 hours. Since little reaction had taken place, the solution was then heated to reflux for 4 hours. The reaction was cooled to room temperature, and the solvent was removed by rotary evaporation. Hydrochloric acid was added to the resulting oil until an acidic pH was reached. The crude product was extracted three times with ethyl acetate, and the organic layers were combined. The solvent was removed by rotary evaporation to provide 4.5 g of the product as a white solid.

b. Preparation of:

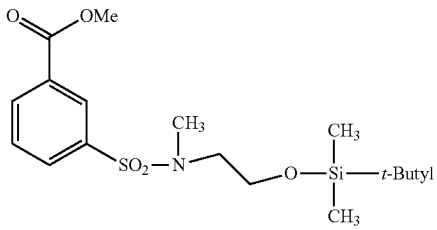

7(b)

Imidazole (4.00 g, 46.5 mmol) and tert-butyldimethylsilyl chloride (4.00 g, 26.5 mmol) were added to a solution of compound 7(a) (4.00 g, 14.6 mmol) in N,N-dimethylformamide (30 ml). The reaction mixture was stirred at 20° C. for 24 hours, then diluted with ethyl acetate. The solution was rinsed with water (2 times), 1N HCl, and brine. The organic layer was concentrated on a rotary evaporator to provide the crude product. The desired product was isolated via flash chromatography (silica gel, ethyl acetate/hexanes) to provide 5.0 g of desired product as a white solid.

c. Preparation of:

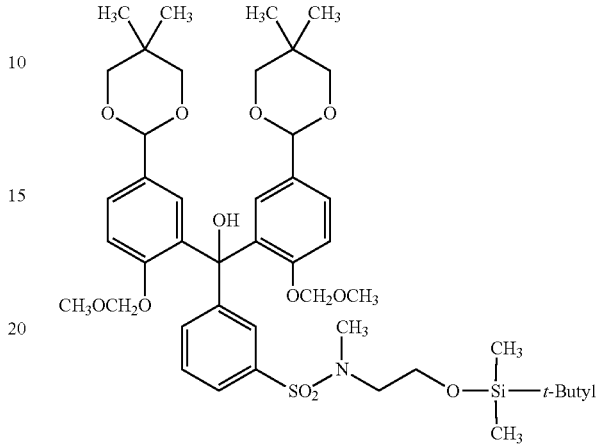

7(c)

2-(4-Methoxymethoxyphenyl)-5,5-dimethyl-1,3-dioxane (6.56 g, 26.0 mmol), prepared according to step b, example 1, was mixed with dry tetrahydrofuran (85 ml) in a 3-neck flask, under argon. N,N,N',N'-Tetramethylethylenediamine (3.92 ml, 26.0 mmol) was added to the solution, and the resulting mixture was cooled to around −5° C. in an ice/NaCl bath. Sec-butyrithium (22.0 ml, 1.3M in cyclohexane, 28.6 mmol) was added via a syringe, maintaining the temperature of the reaction around 0° C. The reaction was stirred for 20 minutes, then a solution of compound 7(b) (3.36 g, 8.67 mmol) in dry tetrahydrofuran (35 ml) was added dropwise to the reaction. After this addition, the solution was stirred for 2 hours at 0° C. The reaction was then quenched with 20% aqueous NH$_4$Cl, and the organic solvents were removed in vacuo. An additional amount of 20% H$_4$Cl solution was added to the aqueous mixture, and then the mixture was extracted two times with ethyl acetate. The organic layers were combined and washed with saturated aqueous NaCl. The crude product was chromatographed (silica gel, ethyl acetate/hexanes gradient), yielding 3.50 g of the desired product as a white solid.

d. Preparation of:

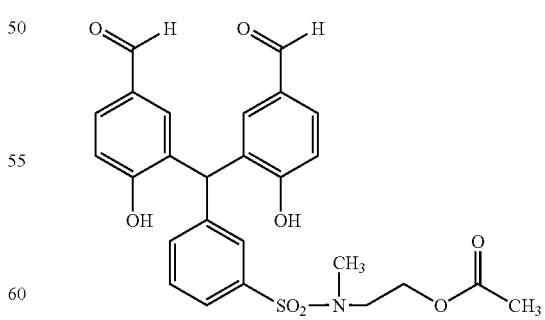

7(d)

Hydriodic acid (4.0 ml, 57 wt % in water) was added to a solution of compound 7(c) (3.0 g, 3.7 mmol) in glacial acetic acid (40 ml). The reaction was stirred at room temperature for 16 hours. The reaction mixture was poured over ice and water, than extracted with ethyl acetate. The organic layer was washed with 10% aqueous NaHSO$_3$ and saturated aqueous NaCl solution, then rotary evaporated. The resulting solid was chromatographed (silica gel, ethyl acetate/hexanes gradient) and recrystallized (ethyl acetate/hexanes) yielding 0.85 g of the desired product as an orange solid.

e. Preparation of:

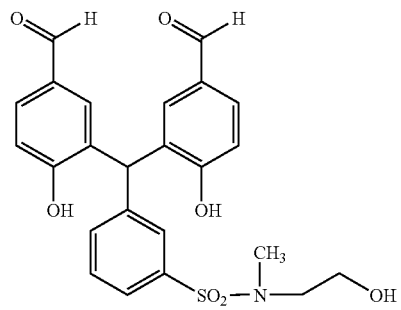

7(e)

Milled potassium carbonate (0.30 g, 2.15 mmol) was added to a solution of compound 7(d) (0.55 g, 1.08 mmol) in methanol (40 ml) and water (5 ml). The reaction was stirred at room temperature for 16 hours. The solution was acidified with 1M HCl, and concentrated in vacuo. The residue was dissolved in ethyl acetate and washed with water. The organic layer was concentrated in vacuo, and the crude product was purified via flash chromatography (silica gel, ethyl acetate), to provide 0.24 g of the desired product as a yellow solid.

f. 3-[[Bis[[5-(5-methyl-1H-tetrazol-1-yl)imino]methyl]-2-hydroxyphenyl]methylene]-N-(hydroxyethyl)-N-methyl-benzenesulfonamide. Compound 7(e) (0.21 g, 0.447 mmol) was dissolved in absolute ethanol (5 ml), and added dropwise to a refluxing solution of 1-amino-5-methyltetrazole (0.13 g, 1.34 mmol) and pyridinium para-toluenesulfonate (11 mg, 0.044 mmol) in ethanol (5 ml). The reaction was heated to reflux for 2 hours, and then cooled to room temperature. The mixture was sonicated, and the solid was collected by filtration and dried under vacuum, yielding 0.14 g of the product as a yellow solid.

Example 8

Preparation of 3-[[Bis[[5-(5-methyl-1H-tetrazol-1-yl)imino]methyl]-2-hydroxyphenyl]methylene]benzenepropanol a. Preparation of:

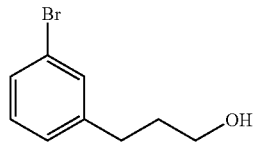

8(a)

Diisobutylaluminum hydride (54.5 ml, 1M in CH$_2$Cl$_2$) was added dropwise to a mechanically stirred solution of 3-bromophenylpropionic acid (5.0 g, 21.8 mmol) in toluene (50 ml) in an ice water bath. Gas evolution was observed. The reaction was slowly warmed to room temperature and stirred overnight. The reaction was quenched with saturated aqueous potassium sodium tartrate (37 ml) and stirred for 3 days at room temperature. The mixture was extracted with ethyl acetate (2×50 ml). The combined organics were washed with brine, dried over MgSO$_4$, filtered, and concentrated in vacuo to provide 2.76 g of desired product.

b. Preparation of:

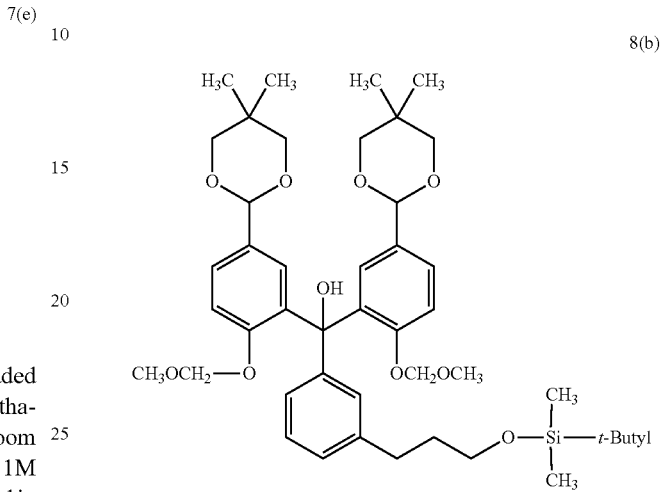

8(b)

The intermediate compound was prepared essentially according to the basic procedure described Example 2, steps c-d above, however compound 8(a) was used in step c instead of 3-bromophenyl ethanol.

c. Preparation of:

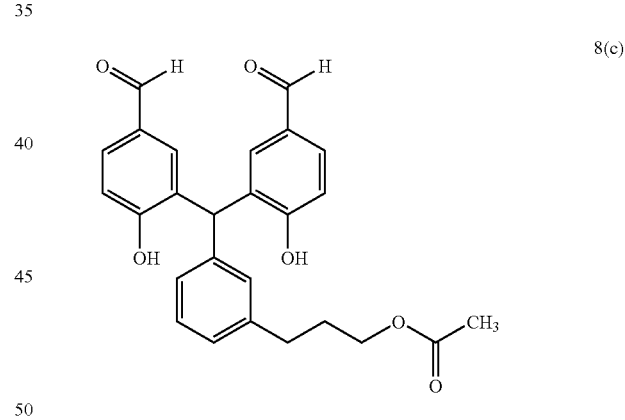

8(c)

Hydriodic acid (3.64 ml, 57% in water) was added to a solution of the compound 8(b)) (2.84 g, 3.64 mmol) in acetic acid (5 ml). The reaction was stirred at room temperature for one hour, quenched with 10% aqueous NaHSO$_3$ and concentrated in vacuo. The residue was partitioned between ethyl acetate and water. The layers were separated, and the aqueous layer was rinsed with ethyl acetate. The combined organics were washed with saturated aqueous NaHCO$_3$ and brine, dried over MgSO$_4$, filtered and concentrated in vacuo. The residue was purified via column chromatography (silica gel, 25% hexanes in ethyl acetate, two times), to provide the desired product.

d. The title compound was then prepared essentially according to the basic procedure described Example 3, steps a and b above; however, compound 8(c) was used in step a instead of compound 2(f)

Example 9

Preparation of 2,2'-[[3-(4-Morpholinylsulfonyl)phenyl]methylene]bis[4-[[(5-methyl-1H-tetrazol-1-yl)imino]methyl]]phenol a. Preparation of:

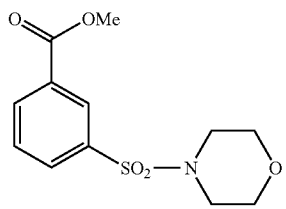

9(a)

A solution of 3-chlorosulfonyl benzoic acid (5.00 g, 22.7 mmol) in tetrahydrofuran (30 ml) was added dropwise to a solution of triethylamine (3 ml) and morpholine (5.00 g, 57.4 mmol) in tetrahydrofuran (30 ml). The mixture was heated to reflux for 18 hours. The solvent was removed by rotary evaporation, and the crude product was diluted with ethyl acetate and washed with 1N HCl. Dry methanol (100 ml) and thionyl chloride (2 ml) were added, and the reaction was stirred for 24 hours. The solvent was removed in vacuo, and 2.62 g of the desired product (white solid) was isolated via flash chromatography (silica gel, ethyl acetate/hexanes).

b. 2,2'-[[3-(4-Morpholinylsulfonyl)phenyl]methylene]bis[4-[[(5-methyl-1H-tetrazol-1-yl)imino]methyl]]phenol. The title compound (0.44 g, yellow solid) was prepared essentially according to the basic procedure described in steps d-f Example 1, above; however, compound 9(a) was used in step d instead of compound 1(c).

Example 10

Preparation of 2,2'-[[3-(Methoxyethoxy)phenyl]methylene]bis[4-[[(5-methyl-1H-tetrazol-1-yl)imino]methyl]]phenol a. Preparation of:

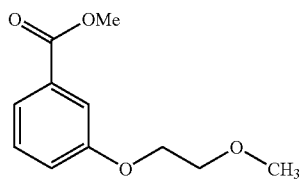

10(a)

Diethyl azodicarboxylate (6.99 ml, 44.36 mmol) was added to a mixture of methyl 3-hydroxy benzoate (4.50 g, 29.58 mmol), triphenylphosphine (9.31 g, 35.49 mmol), tetrahydrofuran (75 ml), and 2-methoxyethanol (2.56 ml, 32.5 mmol). The reaction mixture was heated to reflux for about 16 hours. The solvent was removed by rotary evaporation, and the residue was partitioned between ethyl acetate and 1M NaOH. The solvent was removed from the organic layer by rotary evaporation, and the crude product was purified via flash chromatography (silica gel, ethyl acetate/hexanes gradient) to provide 5.46 g (87%) of pure product as a clear oil.

b. Preparation of:

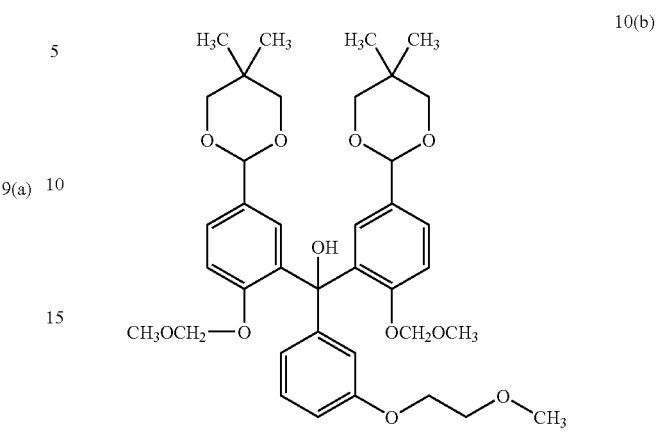

10(b)

2-(4-Methoxymethoxyphenyl)-5,5-dimethyl-1,3-dioxane (6.55 g, 25.97 mmol), prepared according to Example 1, step b, above, was mixed with dry tetrahydrofuran (85 ml), under argon. N,N,N',N'-Tetramethylethylenediamine (3.92 ml, 25.97 mmol) was added to the solution, and the resulting mixture was cooled to around −5° C. in an ice/NaCl bath. Sec-butyllithium (21.98 ml, 1.3M in cyclohexane, 28.57 mmol) was added slowly. The reaction was stirred for 20 minutes at 0° C., and then a solution of compound 10(a) (1.82 g, 8.66 mmol) in dry tetrahydrofuran (35 ml) was added dropwise to the reaction over about 20 minutes. After this addition, the solution was stirred for 2 hours at 0° C., then slowly warmed to room temperature. The reaction was quenched with 20% aqueous $NH_4Cl$, and the organic solvents were removed in vacuo. The mixture was diluted with additional $NH_4Cl$ and extracted two times with ethyl acetate. The organic layers were combined, dried with brine, and concentrated on rotary evaporator. The crude product was chromatographed (silica gel, ethyl acetate/hexanes gradient), yielding 4.64 g of the desired product as an off-white solid.

c. Preparation of:

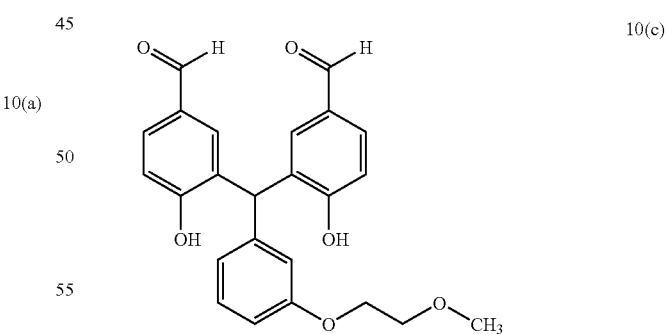

10(c)

Hydriodic acid (3.0 ml, 57 wt % in water) was added to a solution of compound 10(b) (2.0 g, 2.93 mmol) in acetic acid (30 ml). The reaction was stirred at room temperature for 16 hours. The reaction mixture was poured onto ice water (about 100 ml) and extracted with ethyl acetate. The organic layer was washed with 10% aqueous sodium bisulfite and brine, and rotary evaporated. The crude product was purified via flash chromatography (silica gel, ethyl acetate/hexanes gradient), yielding 0.65 g of the desired product.

d. 2,2'-[[3-(Methoxyethoxy)phenyl]methylene]bis[4-[[(5-methyl-1H-tetrazol-1-yl)imino]methyl]]phenol. Compound 10(c) (0.59 g, 1.45 mmol) was dissolved in absolute ethanol (16 ml) and added dropwise to a refluxing solution of 1-amino-5-methyltetrazole (0.43 g, 4.33 mmol) and pyridinium para-toluenesulfonate (36.4 mg, 0.145 mmol) in ethanol (16 ml). The reaction was heated to reflux for 2 hours, and then cooled to room temperature. The solvent was removed by rotary evaporation, and the remaining solid was triturated with water. A solid was collected by filtration and recrystallized in ethanol to provide the title compound.

Example 11

Preparation of 2,2'-[[[3-Bis(phenylmethyl)amino]phenyl]methylene]bis[4-[[(5-methyl-1H-tetrazol-1-yl)imino]methyl]]phenol a. Preparation of:

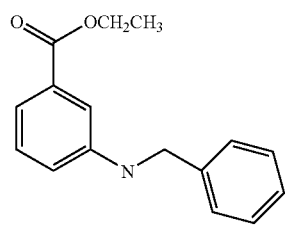

11(a)(i)

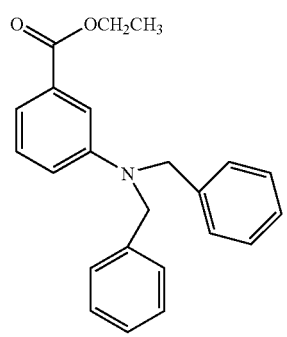

11(a)(ii)

Ethyl 3-aminobenzoate (9.8 g, 0.059 mol), benzyl chloride (20 ml, 0.17 mol), and potassium carbonate (38 g, 0.27 mol) were mixed with ethanol (100 ml) and heated to reflux for about 100 hours. The solvent was removed by rotary evaporation, and the remaining oil was dissolved in ethyl acetate and rinsed with water, 1N HCl, and saturated aqueous Na$_2$CO$_3$. The aqueous layer was extracted with ethyl acetate, and the combined organics were concentrated and purified via flash chromatography (silica gel, 10% ethyl acetate in hexanes) to provide 5.1 g of compound 11(a)(i) and 12.3 g of compound 11(a)(ii).

b. 2,2'-[[[3-Bis(phenylmethyl)amino]phenyl]methylene]bis[4-[[(5-methyl-1H-tetrazol-1-yl)imino]methyl]]phenol. The title compound (0.52 g) was prepared essentially according to the basic procedure described in Example 10, steps b-d, above; however, compound 11(a)(ii) was used in step b instead of compound 10(a).

Example 12

Preparation of 3-[[Bis[[5-(5-methyl-1H-tetrazol-1-yl)imino]methyl]-2-hydroxyphenyl]methylene]phenoxyethanol, acetate ester a. Preparation of:

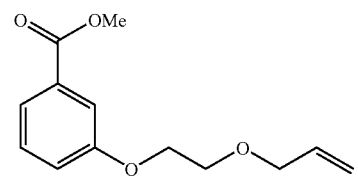

12(a)

Diethyl azodicarboxylate (6.99 ml, 44.36 mmol) was added to a mixture of methyl 3-hydroxy benzoate (4.50 g, 29.58 mmol), triphenylphosphine (9.31 g, 35.49 mmol), tetrahydrofuran (75 ml), and 2-allyloxyethanol (3.48 ml, 32.53 mmol). After stirring at room temperature for one minute, the reaction mixture was heated to reflux for about 16 hours. The solvent was removed by rotary evaporation, and the residue was dissolved in ethyl acetate and diluted with water. The layers were separated and the organics were rinsed with brine. The solvent was removed from the organic layer by rotary evaporation, and the crude product was purified via flash chromatography (silica gel, ethyl acetate/hexanes gradient in 1% increments) to provide 5.62 g of the product as a clear oil.

b. Preparation of:

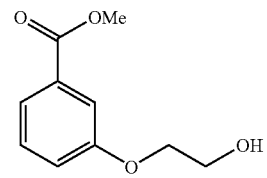

12(b)

Rhodium(III) chloride trihydrate (1.83 g, 6.96 mmol) was added to a solution of (5.48 g, 23.19 mmol) in ethanol (25 ml). The deep red reaction mixture was heated to reflux for one hour. The ethanol was removed by rotary evaporation, and the crude product was purified via flash chromatography (silica gel, ethyl acetate/hexanes gradient) to provide 4.15 g of the product as a light orange oil.

c. Preparation of:

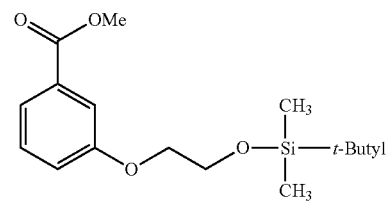

12(c)

Imidazole (4.0 g, 59 mmol) and tert-butyldimethylsilyl chloride (4.7 g, 31 mmol) were added to a solution of compound 12(b) (4.15 g, 21 mmol) in N,N-dimethylformamide (30 ml). The reaction was stirred at 20° C. for 72 hours. The reaction mixture was diluted with ethyl acetate. The solution was rinsed with water (2 times), 1N HCl, and brine. The organic layer was concentrated on a rotary evaporator to provide the crude product. The desired product was isolated via flash chromatography (silica gel, ethyl acetate/hexanes).

d. Preparation of:

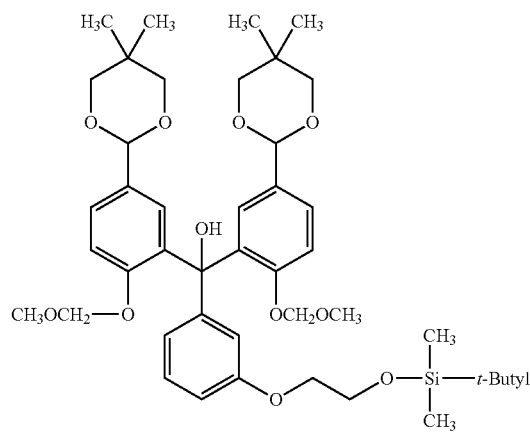

12(d)

2-(4-Methoxymethoxyphenyl)-5,5-dimethyl-1,3-dioxane (6.56 g, 26.0 mmol), prepared according to Example 1, step b, above, was mixed with dry tetrahydrofuran (85 ml), under argon. N,N,N',N'-Tetramethylethylenediamine (3.92 ml, 26.0 mmol) was added to the solution, and the resulting mixture was cooled to around −5° C. in an ice/NaCl bath. Sec-butyllithium (22.0 ml, 1.3M in cyclohexane, 28.60 mmol) was added slowly. The reaction was stirred for 20 minutes at 0° C., and then a solution of compound 12(c) (2.69 g, 8.67 mmol) in dry tetrahydrofuran (35 ml) was added dropwise to the reaction over about 20 minutes. After this addition, the solution was stirred for 2 hours at 0° C., then slowly warmed to room temperature. The reaction was quenched with 20% aqueous NH$_4$Cl (5 ml), and the organic solvents were removed in vacuo. The mixture was diluted with additional NH$_4$Cl and extracted two times with ethyl acetate. The organic layers were combined, dried with brine, and concentrated on rotary evaporator. The crude product was chromatographed (silica gel, ethyl acetate/hexanes gradient), yielding 4.59 g (68%) of the desired product as a white solid.

e. Preparation of:

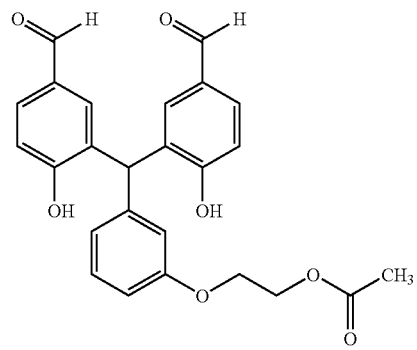

12(e)

Hydriodic acid (4.0 ml, 57 wt % in water) was added to a solution of compound 12(d) (2.50 g, 3.19 mmol) in acetic acid (40 ml). The reaction was stirred at room temperature for about 16 hours. The reaction mixture was poured onto ice water (about 100 ml) and extracted with ethyl acetate. The organic layer was washed with 10% sodium bisulfite and brine, and rotary evaporated. The crude product was purified via flash chromatography (silica gel, ethyl acetate/hexanes gradient) and recrystallization in ethyl acetate/hexanes, yielding 0.83 g (60%) of the desired product as a pale green powder.

f. 3-[[Bis[[5-(5-methyl-1H-tetrazol-1-yl)imino]methyl]-2-hydroxyphenyl]methylene]phenoxyethanol, acetate ester. Compound 12(e) (0.20 g, 0.46 mmol) was dissolved in absolute ethanol (5 ml), and added dropwise to a refluxing solution of 1-amino-5-methyltetrazole (0.137 g, 1.38 mmol) and pyridinium para-toluenesulfonate (12 mg, 0.046 mmol) in ethanol (5 ml). The reaction was heated to reflux for 2 hours, and then cooled to room temperature. A solid was collected by filtration and dried under vacuum to provide 0.21 g of the title compound as a pale green solid.

Example 13

Preparation of 3-[[Bis[[5-(5-methyl-1H-tetrazol-1-yl)imino]methyl]-2-hydroxyphenyl]methylene]-N-(acetoxyethyl)-N-methylbenzenesulfonamide The title compound (0.14 g, yellow solid) was prepared essentially according to the basic procedure described in Example 7, above; however, step e was omitted.

Example 14

Preparation of 3-[[Bis[[5-(5-methyl-1H-tetrazol-1-yl)imino]methyl]-2-hydroxyphenyl]methylene]phenoxyethanol a. Preparation of:

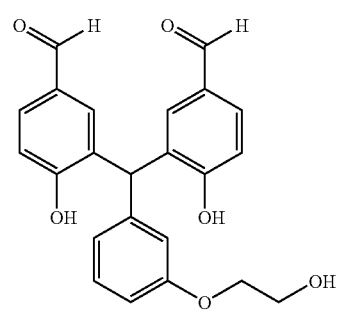

14(a)

Milled potassium carbonate (0.32 g, 2.30 mmol) was added to solution of compound 12(e) (0.50 g, 1.15 mmol) in methanol (40 ml) and water (5 ml). The reaction was stirred at room temperature for 16 hours. The mixture was acidified with 1N HCl (~5 ml), and the methanol was removed by rotary evaporation. The residue was dissolved in ethyl acetate and washed with water. The organic layer was concentrated, and the crude product was purified by flash chromatography (silica gel, ethyl acetate) to provide 0.20 g of the product as a pale yellow product.

b. 3-[[Bis[[5-(5-methyl-1H-tetrazol-1-yl)imino]methyl]-2-hydroxyphenyl]methylene]phenoxyethanol. Compound 14(a) (0.20 g, 0.51 mmol) was dissolved in absolute ethanol (5 ml) and added dropwise to a refluxing solution of 1-amino-5-methyltetrazole (0.15 g, 1.53 mmol) and pyridinium para-toluenesulfonate (13 mg, 0.051 mmol) in ethanol (5 ml). The reaction was heated to reflux for 15 minutes, and then cooled to room temperature. A solid was collected by filtration and dried in vacuo to provide 0.37 g of the title compound as a pale green solid.

Example 15

Preparation of 2-Hydroxy-N-[3-[[bis[[5-(5-methyl-1H-tetrazol-1-yl)imino]methyl]-2-hydroxylphenyl]methylene]phenyl]-N-(methylethyl)acetamide a. Preparation of:

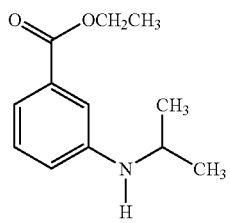

15(a)

Ethyl 3-aminobenzoate (5.30 g, 32.1 mmol), 2-iodopropane (6.78 g, 39.88 mmol), and potassium carbonate (6.0 g, 43.41 mmol) were mixed with ethanol (40 ml) and heated to reflux for 20 hours. The reaction was cooled to room temperature and concentrated by rotary evaporation. The residue was dissolved in ethyl acetate and rinsed with water and brine. The organic layer was concentrated by rotary evaporation, and the product was purified by flash chromatography (silica gel, ethyl acetate/hexanes) to provide 4.7 g (71%) of the desired product as a clear oil.

b. Preparation of:

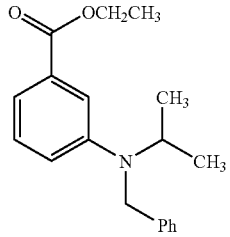

15(b)

Potassium carbonate (11.15 g, 80.67 mmol) and then benzyl chloride (6.96 ml, 60.50 mmol) were added to a solution of compound 15(a) (4.18 g, 20.17 mmol) in ethanol (120 ml). The mixture was heated to reflux for 48 hours. The solvent was removed by rotary evaporation. The residue was dissolved in ethyl acetate and rinsed with water. The crude product was purified two times via flash chromatography (silica gel, ethyl acetate/hexanes gradient) to provide 4.58 g (76%) of pure product as a clear oil.

c. Preparation of:

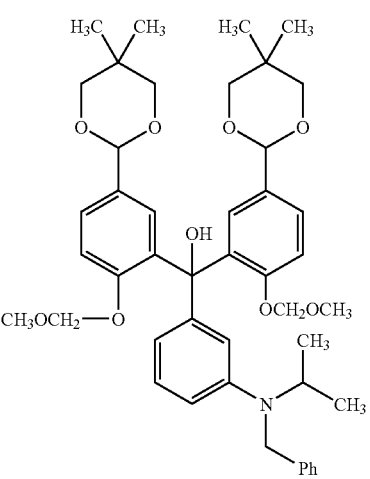

15(c)

2-(4-Methoxymethoxyphenyl)-5,5-dimethyl-1,3-dioxane (10.94 g, 43.38 mmol), prepared according to step b, example 1, was mixed with dry tetrahydrofuran (150 ml) in a 3-neck flask, under argon. N,N,N',N'-Tetramethylethylenediamine (6.54 ml, 43.38 mmol) was added to the solution, and the resulting mixture was cooled to around −5° C. in an ice/NaCl bath. Sec-butyllithium (36.70 ml, 1.3M in cyclohexane, 47.71 mmol) was added via a syringe pump, maintaining the temperature of the reaction around 0° C. The reaction was stirred for 20 minutes, then a solution of compound 15(b) (4.30 g, 14.46 mmol) in dry tetrahydrofuran (60 ml) was added dropwise to the reaction. After this addition, the solution was stirred for 2 hours at 0° C. The reaction was quenched with saturated aqueous NH$_4$Cl, and the organic solvents were removed in vacuo. The mixture was extracted two times with ethyl acetate. The organic layers were combined and washed with saturated aqueous NaCl, and concentrated in vacuo. The crude product was chromatographed (silica gel, ethyl acetate/hexanes gradient), yielding 7.12 g (65%) of the desired product as a yellow solid.

d. Preparation of:

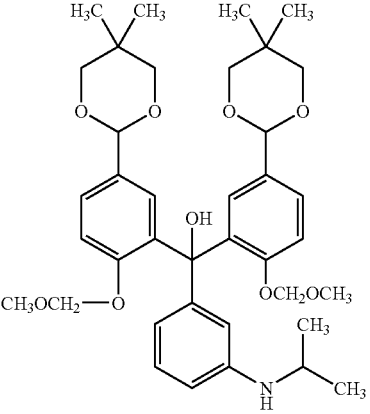

15(d)

A mixture of 10% palladium on carbon (0.10 g) and water (2 ml) was added to a solution of compound 15(c) (1.0 g, 1.32 mmol) in ethanol (30 ml). The reaction flask was placed under 55 psi of hydrogen gas and agitated for four hours. The mixture was filtered through Celite and concentrated in vacuo. The product was passed through a plug of silica gel, rinsing with ethyl acetate, to remove remaining palladium on carbon. The solvent was removed by rotary evaporation to provide 0.84 g of the product as a white solid.

e. Preparation of:

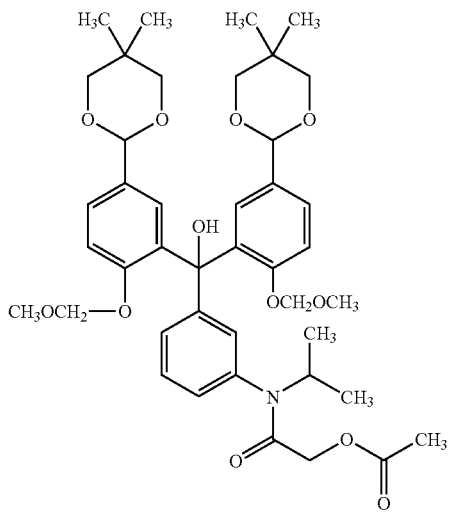

15(e)

Triethylamine (0.94 ml, 6.76 mmol), and acetoxyacetyl chloride (0.73 ml, 6.76 mmol) were added to a solution of compound 15(d) (0.90 g, 1.35 mmol) in dichloromethane (50 ml). The reaction mixture was stirred for 2 hours. The solvent was removed by rotary evaporation, and ethyl acetate was added to the residue. The solution was washed with water and brine, and the organic layer was concentrated in vacuo. The crude product was purified via flash chromatography (silica gel, ethyl acetate/hexanes gradient) to provide 1.0 g of the crude product as a yellow solid. The compound was taken on to the next step without further purification.

f. Preparation of:

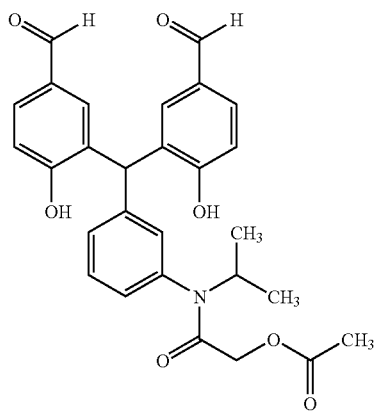

15(f)

Hydriodic acid (2.0 ml, 57 wt % in water) was added to a solution of compound 15(e) (1.0 g, 1.31 mmol) in acetic acid (30 ml). The reaction was stirred at room temperature for about 16 hours. The reaction mixture was poured onto water (~20 ml) and extracted with ethyl acetate. The organic layer was washed with 10% sodium bisulfite (~20 ml) and brine, and rotary evaporated. The crude product was purified via flash chromatography (silica gel, ethyl acetate/hexanes gradient), yielding 0.24 g of the desired product as a yellow solid.

g. Preparation of:

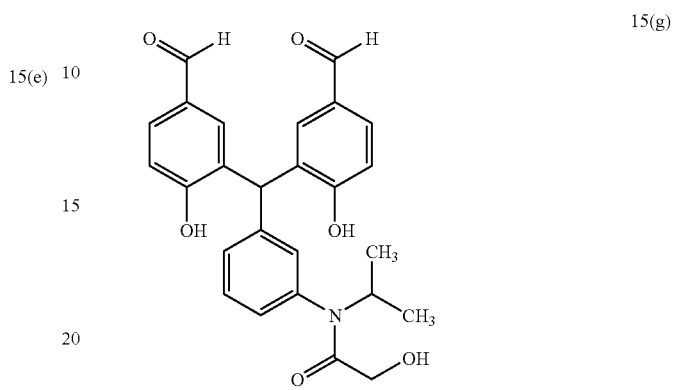

15(g)

Potassium carbonate (0.124 g, 0.899 mmol) was added to a solution of compound 15(f) (0.22 g, 0.449 mmol) in methanol (20 ml) and water (3 ml). The reaction was stirred at room temperature for 48 hours. The solution was acidified with 1M hydrochloric acid (about 2 ml), and concentrated in vacuo. The residue was dissolved in ethyl acetate and washed with water. The organic layer was concentrated in vacuo, and the crude product was purified via flash chromatography (silica gel, ethyl acetate), to provide 0.11 g of the desired product as a yellow solid.

h. 2-Hydroxy-N-[3-[[bis[[5-(5-methyl-1H-tetrazol-1-yl)imino]methyl]-2-hydroxylphenyl]methylene]phenyl]-N-(methylethyl)acetamide. Compound 15(g) (90 mg, 0.201 mmol) was dissolved in absolute ethanol (7 ml), and added dropwise to a refluxing solution of 1-amino-5-methyltetrazole (60 mg, 0.60 mmol) and pyridinium para-toluenesulfonate (5 mg, 0.02 mmol) in ethanol (7 ml). The reaction was heated to reflux for 2 hours, and then stirred at room temperature for about 16 hours. The solvent was removed by rotary evaporation, and a solid was precipitated with water. The product was collected by filtration and dried in vacuo to provide 80 mg of the title compound as a white solid.

Example 16

Preparation of 2-(Acetyloxy)-N-[3-[[bis[[5-(5-methyl-1H-tetrazol-1-yl)imino]methyl]-2-hydroxyphenyl]methylene]phenyl]-N-propylacetamide a. Preparation of:

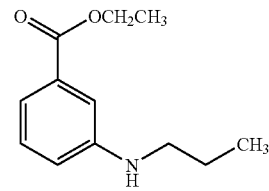

16(a)

Ethyl 3-aminobenzoate (4.00 g, 24.2 mmol), iodopropane (10 ml, 103 mmol), and potassium carbonate (14 g, 101 mmol) were mixed with ethanol (100 ml) and heated to reflux for 40 hours. The reaction was cooled to room temperature and concentrated by rotary evaporation. The residue was dissolved in ethyl acetate and rinsed with water and brine. The organic layer was concentrated by rotary evaporation, and the product was purified by flash chromatography (silica gel, ethyl acetate/hexanes) to provide 3.9 g of the desired product as a clear oil.

b. Preparation of:

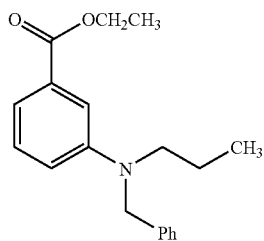

16(b)

Potassium carbonate (4.29 g, 31.07 mmol) and then benzyl chloride (2.68 ml, 23.30 mmol) were added to a solution of compound 16(a) (1.61 g, 7.77 mmol) in ethanol (75 ml). The mixture was heated to reflux for 16 hours. The solvent was removed by rotary evaporation. The residue was dissolved in ethyl acetate and rinsed with water. The crude product was purified via flash chromatography (silica gel, ethyl acetate/ hexanes gradient) and dried in vacuo to provide 3.0 g of the product as a clear oil. This product was taken on to the next step without further purification.

c. Preparation of:

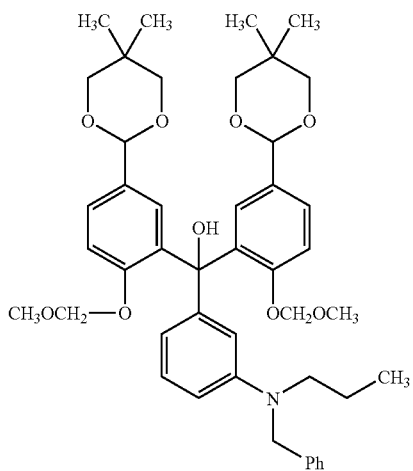

16(c)

2-(4-Methoxymethoxyphenyl)-5,5-dimethyl-1,3-dioxane (6.31 g, 25.02 mmol), prepared according to step b, example 1, was mixed with dry tetrahydrofuran (85 ml) in a 3-neck flask, under argon. N,N,N',N'-Tetramethylethylenediamine (3.78 ml, 25.02 mmol) was added to the solution, and the resulting mixture was cooled to around −5 to 0° C. in an ice/NaCl bath. Sec-butyllithium (21.17 ml, 1.3M in cyclohexane, 27.52 mmol) was added via a syringe. The reaction was stirred for 20 minutes, then a solution of compound 16(b) (2.48 g, 8.34 mmol) in dry tetrahydrofuran (35 ml) was added dropwise to the reaction. After this addition, the solution was stirred for 2 hours at 0° C. The reaction was then quenched with saturated aqueous NH$_4$Cl, and the organic solvents were removed in vacuo. The mixture was extracted with ethyl acetate, washed with saturated aqueous NaCl, and concentrated in vacuo. The crude product was purified via flash chromatography (silica gel, ethyl acetate/hexanes gradient), to provide the product as an off-white solid.

d. Preparation of:

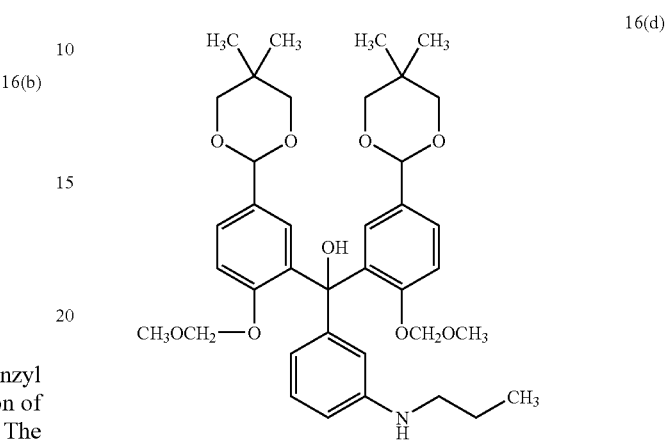

16(d)

A mixture of 10% palladium on carbon (0.10 g) in water (2 ml) was added to a solution of compound 16(c) (1.0 g, 1.32 mmol) in ethanol (30 ml). The reaction flask was placed under 55 psi of hydrogen gas and agitated for four hours. The mixture was filtered through Celite and concentrated in vacuo. The product was passed through a plug of silica gel, rinsing with ethyl acetate, to remove remaining catalyst. The solvent was removed by rotary evaporation to provide 0.83 g of the product as a white solid.

e. Preparation of:

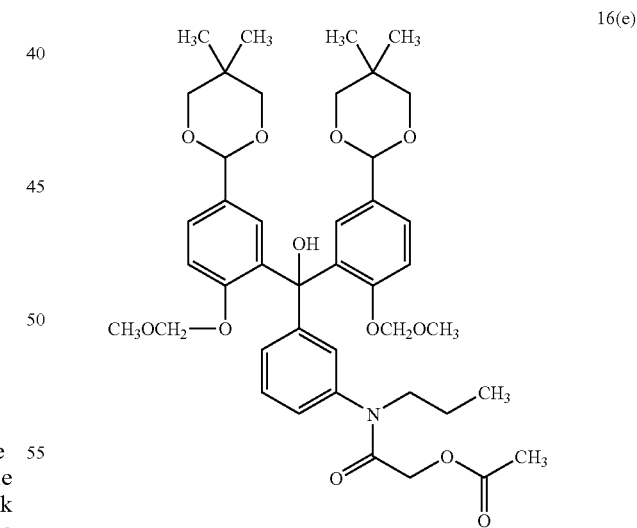

16(e)

4-Dimethylaminopyridine (0.138 g, 1.13 mmol), triethylamine (0.52 ml, 3.75 mmol), and acetoxyacetyl chloride (0.40 ml, 3.75 mmol) were added to a solution of compound 16(d) (0.50 g, 0.75 mmol) in dichloromethane (30 ml). The reaction mixture was stirred for 16 hours. The solvent was removed by rotary evaporation, and ethyl acetate was added to residue. The solution was washed with water and brine, and the organic layer was concentrated in vacuo. The crude product was purified via flash chromatography (silica gel, ethyl acetate/hexanes gradient) to provide 0.12 g of the desired product as a yellow solid.

f. Preparation of:

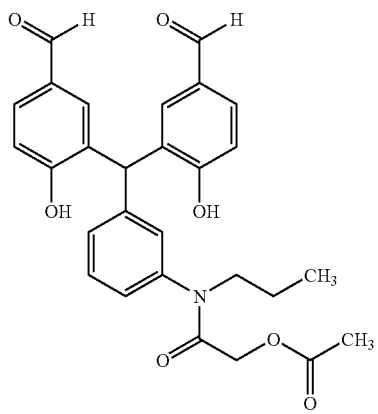

16(f)

Hydriodic acid (1.0 ml, 57 wt % in water) was added to a solution of compound 16(e) (0.14 g, 0.18 mmol) in acetic acid (20 ml). The reaction was stirred at room temperature for about 16 hours. The reaction mixture was poured onto water (about 20 ml) and extracted with ethyl acetate. The organic layer was washed with 10% sodium bisulfite and brine, and rotary evaporated. The crude product was purified via flash chromatography (silica gel, ethyl acetate/hexanes gradient), yielding 40 mg of the desired product as a yellow solid.

g. 2-(Acetyloxy)-N-[3-[[bis[[5-(5-methyl-1H-tetrazol-1-yl)imino]methyl]-2-hydroxyphenyl]methylene]phenyl]-N-propylacetamide. Compound 16(f) (45 mg, 0.092 mmol) was dissolved in absolute ethanol (3 ml), and added dropwise to a refluxing solution of 1-amino-5-methyltetrazole (27 mg, 0.28 mmol) and pyridinium para-toluenesulfonate (3 mg, 0.0092 mmol) in ethanol (3 ml). The reaction was heated to reflux for 2 hours, and then cooled to room temperature and stirred for about 16 hours. The solvent was removed by rotary evaporation, and a solid was precipitated with water. The solid was collected by filtration, dried in vacuo, and recrystallized (ethyl acetate/hexanes) to provide 25 mg of the title compound as a white solid.

Example 17

Preparation of 2,2'-[[3-[1-(4-Methylpiperazinyl)methyl] phenyl]methylene]bis[4-[[(5-1H-tetrazol-1-yl)imino]methyl]]phenol [tosic acid salt]

a. Preparation of:

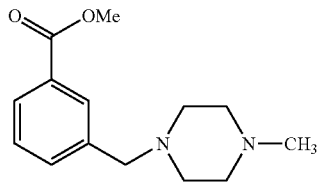

17(a)

A solution of 1-methylpiperazine (4.8 ml, 40 mmol) in tetrahydrofuran (5 ml) was slowly added to a solution of methyl 3-(bromomethyl)benzoate (5.00 g, 20 mmol) in tetrahydrofuran (50 ml). The reaction was stirred at room temperature, under argon, for about 32 hours. Solids were removed by filtration, and the filtrate was concentrated in vacuo. The residue was dissolved in dichloromethane and washed with 2N HCl (175 ml). The aqueous layer was treated with 2M NaOH (200 ml) and extracted with additional dichloromethane. The organic layers were combined, dried with MgSO$_4$, filtered through florisil, concentrated in vacuo, and dried to provide 2.34 g of the desired product.

b. Preparation of:

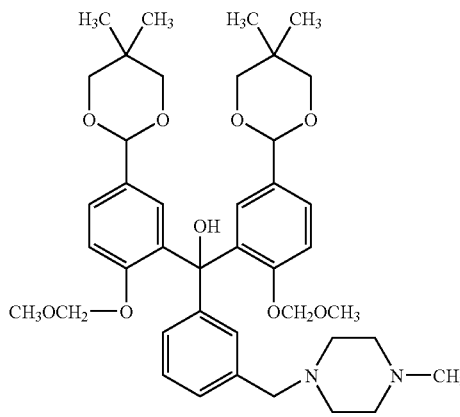

17(b)

2-(4-Methoxymethoxyphenyl)-5,5-dimethyl-1,3-dioxane (7.07 g, 28.0 mmol), prepared according to Example 1, step b, above, was mixed with dry tetrahydrofuran (94 ml), under argon. N,N,N',N'-Tetramethylethylenediamine (4.3 ml, 28.5 mmol) was added to the solution, and the resulting mixture was cooled to around 0° C. in an ice/NaCl bath. Sec-butyllithium (24 ml, 1.3M in cyclohexane, 31.2 mmol) was added dropwise. The reaction was stirred for ~15 minutes below 0° C., and then a solution of compound 17(a) (2.33 g, 9.4 mmol) in dry tetrahydrofuran (32 ml) was added dropwise to the reaction. After this addition, the solution was stirred for 4 hours at 0° C., then quenched with saturated aqueous NH$_4$Cl. The mixture was extracted two times with ethyl acetate. The organic layers were combined, dried with brine and magnesium sulfate, filtered, and concentrated on rotary evaporator. The crude product was chromatographed (silica gel, 0-4% methanol in chloroform), yielding 6.76 g of the desired product.

c. Preparation of:

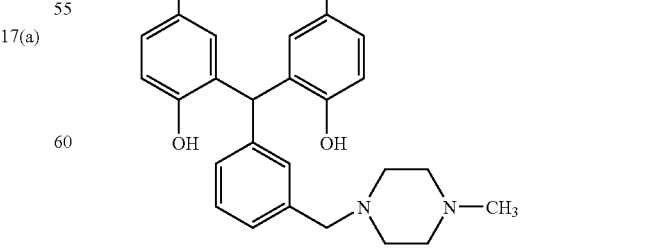

17(c)

Hydriodic acid (4.2 ml, 58 wt % in water) was added to a solution of compound 17(b) (3.01 g, 4.18 mmol) in glacial acetic acid (60 ml). The reaction was stirred at room temperature for about 16 hours. The reaction mixture was concentrated in vacuo, and partitioned between ethyl acetate and sodium bicarbonate solution. Solid sodium bisulfate was added, and the mixture was extracted several times with ethyl acetate. The combined organics were dried with sodium sulfate, filtered, and rotary evaporated. The resulting solid was triturated with hexanes, to provide 1.86 g of the desired product.

d. 2,2'-[[3-[1-(4-Methylpiperazinyl)methyl]phenyl]methylene]bis[4-[[(5-methyl-1H-tetrazol-1-yl)imino]methyl]]phenol [tosic acid salt]. Compound 17(c) (0.31 g, 0.70 mmol) was dissolved in 30 ml absolute ethanol, and added dropwise to a refluxing solution of 1-amino-5-methyltetrazole (0.20 g, 2.02 mmol) and pyridinium para-toluenesulfonate (0.18 g, 0.72 mmol) in 10 ml ethanol. The reaction was heated to reflux for about 16 hours, and then cooled to room temperature. The solution was diluted with a small amount of ethanol and a larger amount of diethyl ether. The solid, which formed upon sonication, was collected by filtration and dried under vacuum, providing the desired product.

Example 18

Preparation of 2,2'-[[3-(Diethylaminomethyl)phenyl]methylene]bis[4-[[(5-methyl-1H-tetrazol-1-yl)imino]methyl]]phenol [tosic acid salt]

a. Preparation of:

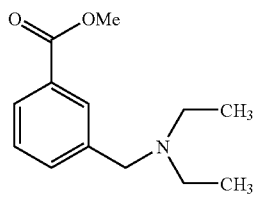

18(a)

Diethylamine (5 ml, 48.3 mmol) was added to a solution of methyl 3-(bromomethyl)benzoate (5.12 g, 22.4 mmol) in tetrahydrofuran (46 ml), and the reaction was stirred at room temperature for about 72 hours. The reaction mixture was partitioned between dichloromethane and water, and washed with 2N HCl (200 ml). 2N NaOH was added to the aqueous layer until basic. The aqueous layer was extracted with additional dichloromethane, and the organics were combined, dried with MgSO$_4$, filtered through florisil, and concentrated in vacuo to provide 4 g of the desired product.

b. 2,2'-[[3-(Diethylaninomethyl)phenyl]methylene]bis[4-[[(5-methyl-1H-tetrazol-1-yl)imino]methyl]]phenol [tosic acid salt]. The title compound was prepared essentially according to the basic procedure described in Example 17, steps b-d, above; however, compound 18(a) was used in step b instead of compound 17(a).

Example 19

Preparation of 2,2'-[[3-(Dimethylaminomethyl)phenyl]methylene]bis[4-[[(5-methyl-1H-tetrazol-1-yl)imino]methyl]]phenol [tosic acid salt]

a. Preparation of:

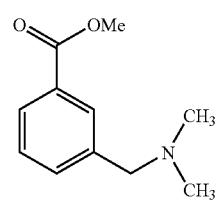

19(a)

Dimethylamine (20 ml, 2M in tetrahydrofuran, 40 mmol) was slowly added to a solution of methyl 3-(bromomethyl)benzoate (5.00 g, 20 mmol) in tetrahydrofuran (50 ml). The reaction was stirred at room temperature, under argon, for about 32 hours. Solids were removed by filtration, and the filtrate was concentrated in vacuo. The residue was dissolved in dichloromethane and washed with 2N HCl (200 ml). The aqueous layer was treated with 2M NaOH (250 ml) and extracted with additional dichloromethane (2 times). The organic layers were combined, dried with MgSO$_4$, filtered through florisil, concentrated in vacuo, and dried to provide 1.8 g of the desired product.

b. 2,2'-[[3-(Dimethlaminomethyl)phenyl]methylene]bis[4-[[(5-methyl-1H-tetrazol-1-yl)imino]methyl]]phenol [tosic acid salt]. The title compound was prepared essentially according to the basic procedure described in Example 17, steps b-d, above; however, compound 19(a) was used in step b instead of compound 17(a).

Example 20

Preparation of 2,2'-[[3-[4-(Morpholinyl)methyl]phenyl]methylene]bis[4-[[(5-methyl-1H-tetrazol-1-yl)imino]methyl]]phenol [tosic acid salt]

a. Preparation of:

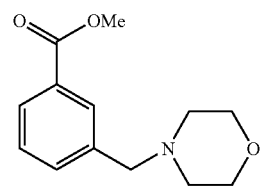

20(a)

A solution of morpholine (3.8 ml, 40 mmol) in tetrahydrofuran (4 ml) was slowly added to a solution of methyl 3-(bromomethyl)benzoate (5.00 g, 20 mmol) in tetrahydrofuran (50 ml). The reaction was stirred at room temperature, under argon, for about 32 hours. Solids were removed by filtration, and the filtrate was concentrated in vacuo. The residue was dissolved in dichloromethane and washed with 2N HCl (175 ml). The aqueous layer was treated with 2M NaOH (200 ml) and extracted with additional dichloromethane. The organic layers were combined, dried with MgSO$_4$, filtered through florisil, concentrated in vacuo, and dried to provide 3.87 g of the desired product.

b. 2,2'-[[3-[4-(Morpholinyl)methyl]phenyl]methylene]bis[4-[[(5-methyl-1H-tetrazol-1-yl)imino]methyl]]phenol [tosic acid salt]. The title compound was prepared essentially according to the basic procedure described in Example 17, steps b-d, above; however, compound 20(a) was used in step b instead of compound 17(a).

Example 21

Preparation of 2,2'-[[3-[N-(4-Hydroxybutyl)-N-ethylamino]phenyl]methylene]bis[4-[[(5-methyl-1H-tetrazol-1-yl)imino]methyl]]phenol a. Preparation of:

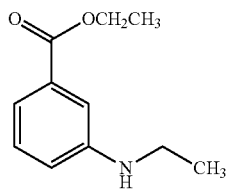

21(a)

Ethyl 3-aminobenzoate (20 g, 0.12 mol) was added to a mixture of Raney Nickel (40 g) in ethanol (400 ml). The mixture was heated to reflux for about 16 hours. The reaction mixture was cooled to room temperature and filtered through Celite. The solvent was removed by rotary evaporation to provide 20.76 g of the desired product as a white solid.

b. Preparation of:

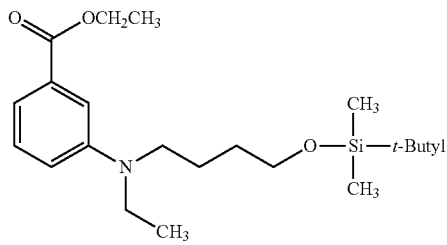

21(b)

Tert-Butyl(4-iodobutoxy)dimethylsilane (40 ml, 0.15 mol) and diisopropylethylamine (26 ml, 0.15 mol) were added to a solution of compound 21(a) (10.0 g, 52 mmol) in acetonitrile (200 ml), then heated to reflux for about 16 hours. The mixture was cooled to room temperature, diluted with water and extracted three times into ethyl acetate. The combined organics were dried with MgSO$_4$, filtered, and rotary evaporated. The crude product was purified via column chromatography (two times, silica gel, 2% and 0.5% ethyl acetate in hexanes) to provide 8.1 g of the desired product.

c. Preparation of:

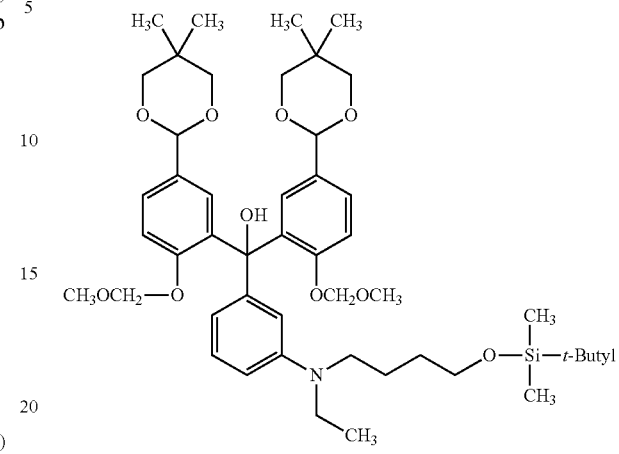

21(c)

2-(4-Methoxymethoxyphenyl)-5,5-dimethyl-1,3-dioxane (16.2 g, 64.0 mmol), prepared according to step b, above, was mixed with dry tetrahydrofuran (200 ml), under argon. N,N,N',N'-Tetramethylethylenediamine (9.66 ml, 64.0 mmol) was added to the solution, and the resulting mixture was cooled to around −10° C. in an ice/NaCl bath. Sec-butyllithium (54.2 ml, 1.3M in cyclohexane, 70.4 mmol) was added dropwise, maintaining the temperature below 0° C. The reaction was stirred for 15 minutes at 0° C., and then a solution of compound 21(b) (8.1 g, 21.3 mmol) in dry tetrahydrofuran (83 ml) was added dropwise to the reaction. After this addition, the solution was stirred for 2 hours at 0° C., then quenched with 20% aqueous NH$_4$Cl. The organic solvents were removed in vacuo. The mixture was extracted two times with ethyl acetate (45 ml). The organic layers were combined, dried with magnesium sulfate, filtered, and concentrated on rotary evaporator. The crude product was chromatographed (silica gel, 15-20% ethyl acetate in hexanes), yielding 9.51 g of the desired product.

d. Preparation of:

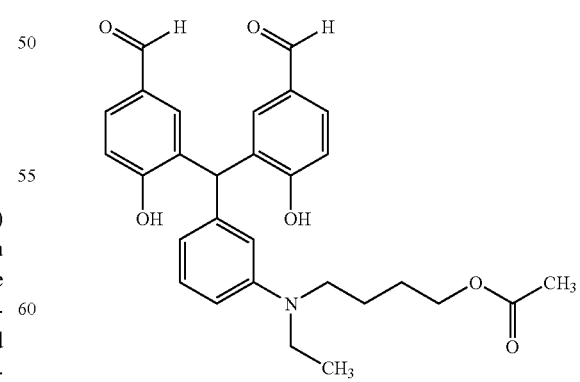

21(d)

Hydriodic acid (11.3 ml, 58 wt % in water) was added to a solution of compound 21(c) (9.50 g, 11.3 mmol) in glacial acetic acid (113 ml). The reaction was stirred at room temperature for 2 hours. The acetic acid was removed by rotary evaporation, and 10% sodium bisulfite was added to the residue. NaHCO$_3$ was added until a pH ~8 was achieved, and then the product was extracted into ethyl acetate (three times). The combined organics were dried over magnesium sulfate, filtered, and rotary evaporated. The resulting solid was purified by recrystallization (ethyl acetate/hexanes) and column chromatography (silica gel, 50-100% ethyl acetate in hexanes), yielding 3.62 g of the desired product.

e. Preparation of:

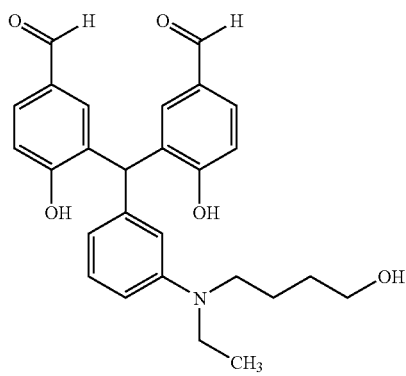

21(e)

Milled potassium carbonate (2.06 g, 14.9 mmol) was added to a solution of compound 21(d) (3.31 g, 6.76 mmol) in methanol (80 ml) and water (2 ml). The reaction was stirred at room temperature for about 16 hours. The solvents were removed by rotary evaporation, and the residue was dissolved in ethyl acetate and water (10 ml). The mixture was neutralized with 1M HCl (~pH 7), and the layers were separated. The aqueous layer was extracted several times with ethyl acetate. The combined organic layers were dried over magnesium sulfate, filtered, and rotary evaporated to provide 3.01 g of the desired product.

f. 2,2'-[[3-[N-(4-Hydroxybutyl)-N-ethylamino]phenyl]methylene[bis[4-[[(5-methyl-1H-tetrazol-1-yl)imino]methyl]]phenol. Compound 21(e) (2.77 g, 6.19 mmol) was dissolved in absolute ethanol (75 ml), and added dropwise to a refluxing solution of 1-amino-5-methyltetrazole (1.84 g, 18.6 mmol) and pyridinium para-toluenesulfonate (1.71 g, 6.8 mmol) in 75 ml ethanol. The reaction was heated to reflux for 2 hours, and then cooled to room temperature. The mixture was diluted t-butyl methyl ether (about 1.5 L), and the tosic acid salt of the product was collected by filtration.

The isolated salt was mixed with water (50 ml), ethyl acetate (200 ml), and NaHCO$_3$ (1.04 g) to convert to the free base, and extracted with additional ethyl acetate (2×100 ml). The combined organic layers were dried over magnesium sulfate, filtered, and rotary evaporated. The solid was dissolved in ethyl acetate along with pH 6 buffer (McIlvan's buffer, NaHPO$_3$ and citric acid) and was recrystallized in hot ethanol to provide 2.0 g of the title compound.

Example 22

Preparation of 2-(Acetyloxy)-N-[3-[[Bis[[5-(5-methyl-1H-tetrazol-1-yl)imino]methyl]-2-hydroxyphenyl]methylene]phenyl]-2-methylpropanamide a. Preparation of:

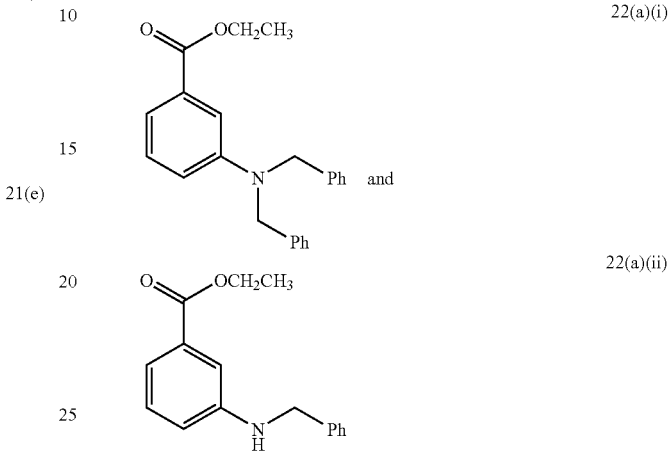

Ethyl 3-aminobenzoate (11.77 g, 71.25 mmol), benzyl chloride (25 ml, 217 mmol), and potassium carbonate (36 g, 260 mmol) were mixed with ethanol and heated to reflux for about 10 days. The solvent was removed by rotary evaporation, and the remaining oil was dissolved in ethyl acetate and rinsed with water, dilute HCl, and saturated Na$_2$CO$_3$. The aqueous layer was extracted with ethyl acetate, and the combined organics were concentrated and purified via flash chromatography (silica gel, 10% ethyl acetate in hexanes) to provide both the monobenzyl amine (compound 22(a)(i)) and the dibenzyl amine (compound 22(a)(ii)) products.

b. Preparation of:

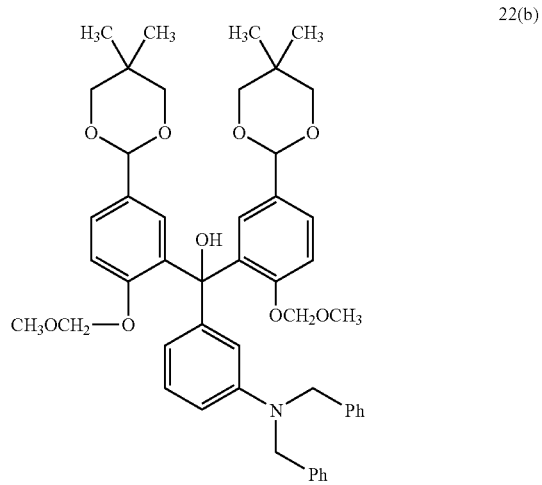

2-(4-Methoxymethoxyphenyl)-5,5-dimethyl-1,3-dioxane (7.6 g, 30.1 mmol), prepared according to step b, example 1, was mixed with dry tetrahydrofuran (100 ml) in a 3-neck flask, under argon. N,N,N',N'-Tetramethylethylenediamine (4.48 ml, 29.7 mmol) was added to the solution, and the resulting mixture was cooled to around 0° C. in an ice/NaCl bath. Sec-butyllithium (26 ml, 1.3M in cyclohexane, 33.8 mmol) was added in two portions. The reaction was stirred for 25 minutes, then a solution of compound 22(a)(ii) (3.4 g, 9.84 mmol) in dry tetrahydrofuran (40 ml) was added dropwise to the reaction over 30 minutes. After this addition, the solution was stirred for 1.5 hours at 0° C. The reaction was then quenched with saturated aqueous NI$_4$Cl (7 ml), and stirred at room temperature for about 16 hours. The organic solvents were removed in vacuo, and the mixture was extracted with ethyl acetate, washed with saturated aqueous NH$_4$Cl, and concentrated in vacuo. The crude product was chromatographed (two times, silica gel, ethyl acetate/hexanes) to provide the desired product as a white solid.

c. Preparation of:

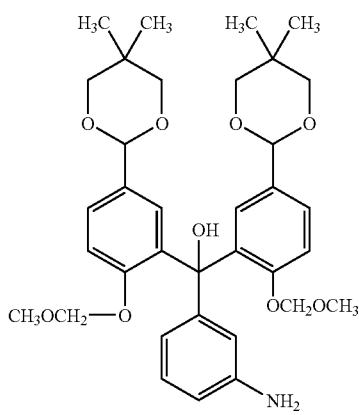

22(c)

10% Palladium on carbon (0.5 g) was mixed with methanol (100 ml) and added to compound 22(b) (10.0 g, 12.4 mmol). The reaction flask was placed under 50 psi of hydrogen gas and agitated for four hours. The mixture was filtered through Celite and concentrated in vacuo. The product was passed through a plug of silica gel, rinsing with ethyl acetate to remove remaining palladium on carbon. The solvent was removed by rotary evaporation to provide 7.13 g (92%) of the desired product as a white solid.

d. Preparation of:

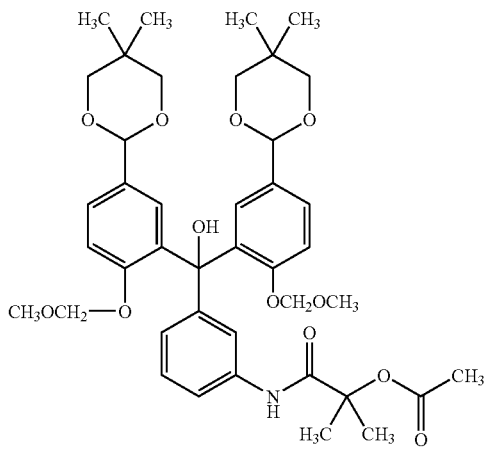

22(d)

1-Chlorocarbonyl-1-methylethyl acetate (0.22 ml, 1.52 mmol) was added to a solution of compound 22(c) (0.83 g, 1.33 mmol) and triethylamine (0.4 ml, 2.86 mmol) in dichloromethane. The mixture was stirred at room temperature for 23 hours. The solvent was removed by rotary evaporation, and the residue was diluted with ethyl acetate, washed with water, dried with brine, and concentrated in vacuo. The crude product was purified via column chromatography (silica gel, ethyl acetate/hexanes) to provide 0.78 g (78%) of the desired product as a white solid.

e. Preparation of:

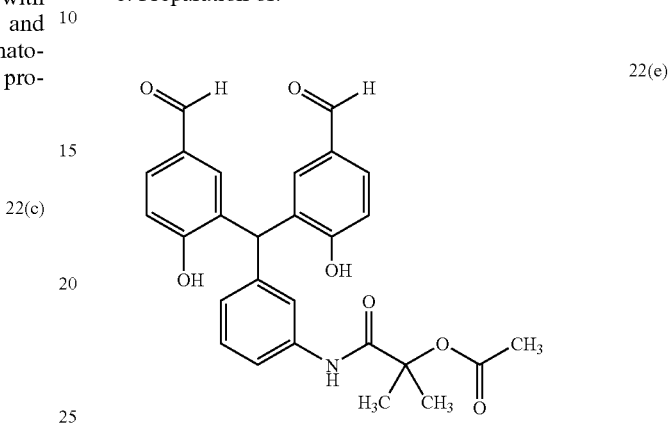

22(e)

Hydriodic acid (1.0 ml, 56 wt % in water) was added to a mixture of compound 22(d) (0.78 g, 1.04 mmol) in glacial acetic acid (15 ml). The reaction was stirred at room temperature for 3 hours, and quenched with saturated sodium sulfite. About ½ of the solvent was removed by rotary evaporation, and saturated aqueous sodium bicarbonate was added dropwise, until the mixture was basic. The mixture was extracted with ethyl acetate (several times), and the combined organics were rotary evaporated. The crude product was purified via flash chromatography (silica gel, 50% hexanes in ethyl acetate), providing the desired product as a white solid.

f. 2-(Acetyloxy)-N-[3-[[Bis[[5-(5-methyl-1H-tetrazol-1-yl)imino]methyl]-2-hydroxyphenyl]methylene]phenyl]-2-methylpropanamide. The title compound (0.10 g) was then prepared essentially according to the basic procedure described in Example 12 step f; however, compound 22(e) was used instead of compound 12(e).

Example 23

Preparation of N-[3-[[Bis[[5-(5-methyl-1H-tetrazol-1-yl)imino]methyl]-2-hydroxyphenyl]methylene]phenyl]-2-methoxyacetamide The title compound was prepared essentially according to the basic procedure described in Example 22, above; however, methoxyacetyl chloride was used in step d instead of 1-chlorocarbonyl-1-methylethyl acetate.

Example 24

Preparation of N-[3-[[Bis[[5-(5-methyl-1H-tetrazol-1-yl)imino]methyl]-2-hydroxylphenyl]methylene]phenyl]-cyclopropanecarboxamide The title compound was prepared essentially according to the basic procedure described in Example 22, above; however, cyclopropanecarbonyl chloride was used in step d instead of 1-chlorocarbonyl-1-methylethyl acetate.

Example 25

Preparation of N-[3-[[Bis[[5-(5-methyl-1H-tetrazol-1-yl)imino]methyl]-2-hydroxylphenyl]methylene]phenyl]-N-(butylsulfonyl)butane sulfonamide The title compound was prepared essentially according to the basic procedure described in Example 22, above; however, 1.64 equivalents of 1-butanesulfonyl chloride was used in step d instead of 1-chlorocarbonyl-1-methylethyl acetate.

Example 26

Preparation of N-[3-[[Bis[[5-(5-methyl-1H-tetrazol-1-yl)imino]methyl]-2-hydroxylphenyl]methylene]phenyl]-N-(2,2,2-trifluoroethylsulfonyl)-2,2,2-trifluoroethane sulfonamide The title compound was prepared essentially according to the basic procedure described in Example 22, above; however, 3.0 equivalents of 2,2,2-trifluoroethanesulfonyl chloride was used in step d instead of 1-chlorocarbonyl-1-methylethyl acetate.

Example 27

Preparation of N-[3-[[Bis[[5-(5-methyl-1H-tetrazol-1-yl)imino]methyl]-2-hydroxylphenyl]methylene]phenyl]-2-hydroxy-2-methyl-propanamide a. Preparation of:

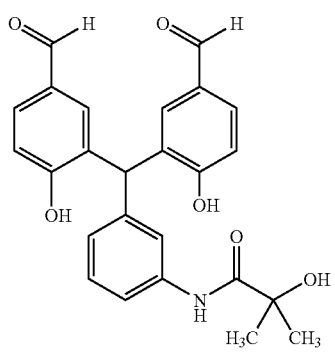

27(a)

Potassium carbonate (0.30 g, 2.17 mmol) was added to a solution of compound 22(e) (0.20 g, 0.43 mmol) in methanol (20 ml) and water (3 ml). The reaction mixture was stirred at room temperature for 24 hours. The mixture was concentrated in vacuo, diluted with ethyl acetate, and rinsed with water, 1N HCl, and brine. The ethyl acetate was removed by rotary evaporation, and the crude product was purified via flash chromatography (silica gel, 50/50 ethyl acetate/hexanes+1% acetic acid) to provide 0.15 g of the desired product.

b. N-[3-[Bis[[5-(5-methyl-1H-tetrazol-1-yl)imino]methyl]-2-hydroxylphenyl]methylene]phenyl]-2-hydroxy-2-methyl-propanamide. The title compound (0.15 g) was then prepared essentially according to the basic procedure described in Example 12 step f; however, compound 27(a) was used instead of compound 12(e).

Example 28

Preparation of N-[3-[[Bis[[5-(5-methyl-1H-tetrazol-1-yl)imino]methyl]-2-hydroxylphenyl]methylene]phenyl]-N-(propylsulfonyl)propane sulfonamide The title compound was prepared essentially according to the basic procedure described in Example 22, above; however, 1.5 equivalents of 1-propanesulfonyl chloride was used in step d instead of 1-chlorocarbonyl-1-methylethyl acetate.

Example 29

Preparation of N-[3-[[Bis[[5-(5-methyl-1H-tetrazol-1-yl)imino]methyl]-2-hydroxylphenyl]methylene]phenyl]-N-(3-chloropropylsulfonyl)-3-chloropropane sulfonamide a. Preparation of:

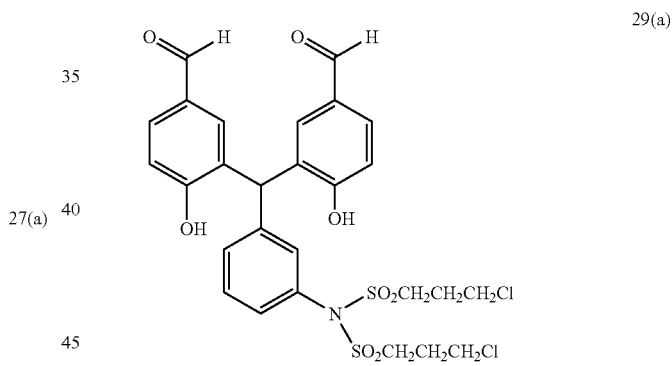

29(a)

The intermediate compound was prepared essentially according to the basic procedure described in Example 22, steps a-e above; however, 3.3 equivalents of 3-chloropropanesulfonyl chloride was used in step d instead of 1-chlorocarbonyl-1-methylethyl acetate.

b. N-[3-[[Bis[[5-(5-methyl-1H-tetrazol-1-yl)imino]methyl]-2-hydroxylphenyl]methylene]phenyl]-N-(3-chloropropylsulfonyl)-3-chloropropane sulfonamide. Compound 29(a) (40 mg, 0.064 mmol) was dissolved in absolute ethanol (7 ml) and added dropwise to a refluxing solution of 1-amino-5-methyltetrazole (19 mg, 0.191 mmol) and pyridinium para-toluenesulfonate (2 mg, 0.0064 mmol) in ethanol (7 ml). The reaction was heated to reflux for 2 hours, and then cooled to room temperature. The solvent was concentrated on rotary evaporator until ~2 ml of ethanol remained. The mixture was stirred with water (5 ml), and the resulting solid was isolated by filtration and dried to provide 40 mg (74%) of the title compound as an off-white solid.

Example 30

Preparation of 2-(Acetyloxy)-N-[3-[[bis[[5-(5-methyl-1H-tetrazol-1-yl)imino]methyl]-2-hydroxyphenyl]methylene]phenyl]acetamide a. Preparation of:

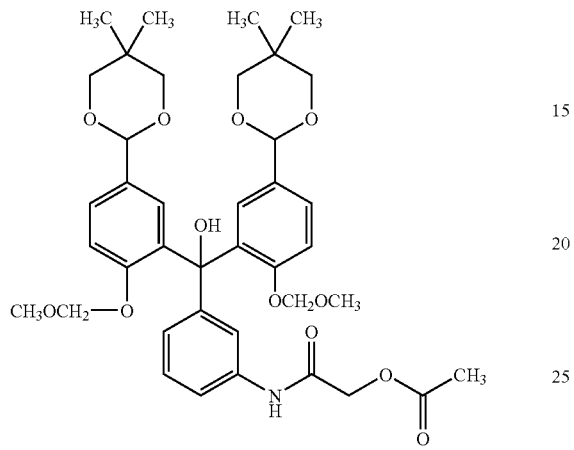

30(a)

The intermediate compound was prepared essentially according to the basic procedure described in Example 22, steps a-d above; however, acetoxyacetyl chloride was used in step d instead of 1-chlorocarbonyl-1-methylethyl acetate.

b. Preparation of:

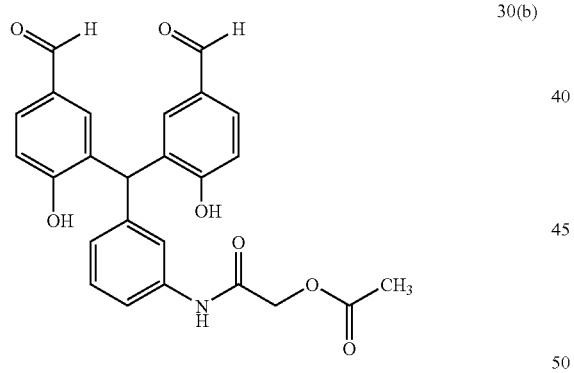

30(b)

Hydriodic acid (~1 ml, 57 wt % in water) was added to a solution of compound 30(a) (0.270 g, 0.373 mmol) in acetic acid (15 ml). The reaction was stirred at room temperature for 16 hours. The reaction mixture was poured onto ice water (about 100 ml) and extracted with ethyl acetate. The organic layer was washed with 10% sodium bisulfite and brine, and rotary evaporated, co-evaporating with dichloromethane. The crude product was purified via flash chromatography (silica gel, ethyl acetate/hexanes gradient), yielding 50 mg of the desired product as a yellow solid.

c. 2-(Acetyloxy)-N-[3-[[bis[[5-(5-methyl-1H-tetrazol-1-Yl)imino]methyl]-2-hydroxyphenyl]methylene]phenyl]acetamide. Compound 30(b) (40 mg, 0.089 mmol) was dissolved in absolute ethanol (3 ml), and added dropwise to a refluxing solution of 1-amino-5-methyltetrazole (26.5 mg, 0.268 mmol) and pyridinium para-toluenesulfonate (3 mg, 0.0089 mmol) in ethanol (3 ml). The reaction was heated to reflux for 2 hours, and then cooled to room temperature overnight. The solid was collected by filtration and dried to provide 40 mg (74%) of the title compound.

Example 31

Preparation of N-[3-[[Bis[[5-(5-methyl-1H-tetrazol-1-yl)imino]methyl]-2-hydroxylphenyl]methylene]phenyl]-N-(methylsulfonyl)methane sulfonamide The title compound was prepared essentially according to the basic procedure described in Example 30, above; however, methanesulfonyl chloride was used in step a instead of acetoxyacetyl chloride.

Example 32

Preparation of 2,2'-[[3-[2-(1,1-Dioxide-2,3,4,5-tetrahydro)isothiazolyl]phenyl]methylene]bis[4-[[(5-methyl-1H-tetrazol-1-yl)imino]methyl]]phenol a. Preparation of:

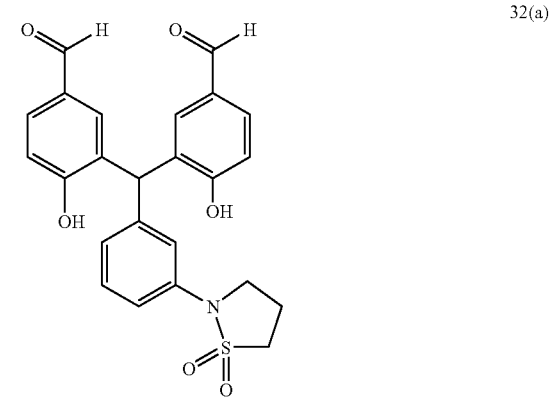

32(a)

Compound 29(a) (0.100 g 0.159 mmol) was refluxed in saturated aqueous sodium carbonate (10 ml) for two hours. After cooling to room temperature, 1N HCl was added until pH 7 was reached. The mixture was extracted with ethyl acetate (2×). The aqueous layer was further acidified with 1N HCl until pH 1, and again extracted with ethyl acetate (2×). The organics were combined, and the solvent was removed by rotary evaporation. The crude solid was purified via column chromatography (silica gel, ethyl acetate/hexanes+1% acetic acid) to provide 63 mg (88%) of the product as a white solid.

b. 2,2'-[[3-[2-(1,1-Dioxide-2,3,4,5-tetrahydro)isothiazolyl]phenyl]methylene]bis[4-[[(5-methyl-1H-tetrazol-1-yl)imino]methyl]]phenol. Compound 32(a) (63 mg, 0.14 mmol) was dissolved in absolute ethanol (7 ml), and added dropwise to a refluxing solution of 1-amino-5-methyltetrazole (42 mg, 0.419 mmol) and pyridinium para-toluenesulfonate (4 mg, 0.014 mmol) in ethanol (7 ml). The reaction was heated to reflux for 2 hours, and then cooled to room temperature. The mixture was rotary evaporated, and the residue was dissolved in ethanol. A solid was precipitated with water, which was filtered to provide 60 mg of the title product as a yellow solid.

Example 33

Preparation of 2-Hydroxy-N-[3-[[bis[[5-(5-methyl-1H-tetrazol-1-yl)imino]methyl]-2-hydroxylphenyl]methylene]phenyl]acetamide a. Preparation of:

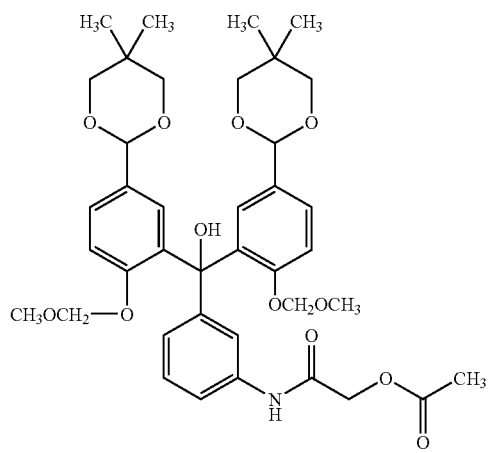

33(a)

Triethylamine (0.3 ml) and acetoxyacetyl chloride (0.070 ml, 0.65 mmol) were added to a solution of compound 22(c) (0.30 g, 0.48 mmol) in dichloromethane (30 ml). The reaction mixture was stirred for 20 hours. The solvent was removed by rotary evaporation, and ethyl acetate was added to the residue. The solution was washed with water and brine, and the organic layer was concentrated in vacuo. The crude product was purified via flash chromatography (silica gel, ethyl acetate/hexanes gradient) to provide 1.0 g of the desired product as a clear oil.

b. Preparation of:

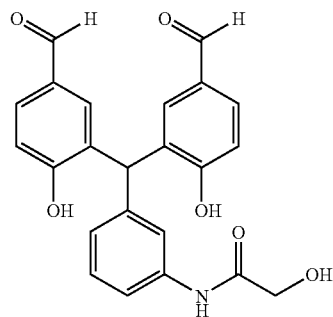

33(b)

Hydriodic acid (1.0 ml, 57 wt % in water) was added to a solution of compound 33(a) (0.5 g, 0.69 mmol) in acetic acid (15 ml). The reaction was stirred at room temperature for 20 hours. The reaction was quenched with the dropwise addition of saturated aqueous sodium sulfite. The product was extracted into ethyl acetate, and the organic layer was washed with water and saturated $Na_2CO_3$. The solvent was removed in vacuo, and the crude product was purified via flash chromatography (silica gel, ethyl acetate/hexanes gradient) to provide 110 mg (39%) of the desired product as a white solid.

c. 2-Hydroxy-N-[3-[[bis[[5-(5-methyl-1H-tetrazol-1-yl)imino]methyl]-2-hydroxylphenyl]methylene]phenyl]acetamide. Compound 33(b) (110 mg, 0.271 mmol) was dissolved in absolute ethanol (7 ml) and added dropwise to a refluxing solution of 1-amino-5-methyltetrazole (81 mg, 0.814 mmol) and pyridinium para-toluenesulfonate (7 mg, 0.027 mmol) in ethanol (7 ml). The reaction was heated to reflux for 2 hours, and then cooled to room temperature. The solvent was concentrated on rotary evaporator until ~2 ml of ethanol remained. The mixture was stirred with water (5 ml), and the resulting solid was isolated by filtration and dried to provide 60 mg of the title compound as a yellow solid.

Example 34

Preparation of 2,2'-[[3-[N-(3-Hydroxypropyl)-N-ethylamino]phenyl]methylene]bis[4-[[(5-methyl-1H-tetrazol-1-yl)imino]methyl]]phenol a. Preparation of:

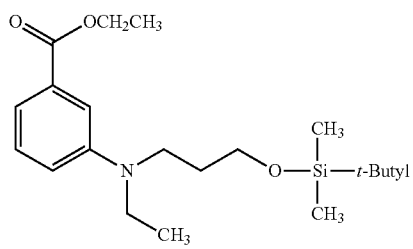

34(a)

(3-Bromopropoxy)-tert-butyldimethylsilane (18 ml, 78 mmol), sodium iodide (1.9 g, 13 mmol), and diisopropylethylamine (14 ml, 78 mmol) were added to a solution of compound 21(a) (5.0 g, 26 mmol) in acetonitrile (60 ml). The reaction mixture was heated to reflux for 4 hours, then stirred at room temperature for about 72 hours. Since the reaction did not go to completion, the reaction was again refluxed with an additional equivalent of sodium iodide and additional (3-bromopropoxy)-tert-butyldimethylsilane (6 ml). The mixture was cooled to room temperature, concentrated in vacuo and extracted two times into ethyl acetate. The combined organics were dried with $MgSO_4$, filtered, and rotary evaporated. The crude product was purified via column chromatography (silica gel, 5-20% ethyl acetate in hexanes) to provide 4.36 g of the desired product.

b. 2,2'-[[3-[N-(3-Hydroxypropyl)-N-ethylamino]phenyl]methylene]bis[4-[[(5-methyl-1H-tetrazol-1-yl)imino]methyl]]phenol. The tosic acid salt of the title compound was then prepared essentially according to the basic procedure described in Example 21 steps c-f; however, compound 34(a) was used in step c instead of compound 21(b).

The free base was isolated by adding sodium bicarbonate (0.148 g, 17.6 mmol) to a suspension of the salt in water (10 ml). Ethyl acetate was added to the suspension until the solids dissolved. The mixture was extracted several times with ethyl acetate, and the combined organics were dried over $MgSO_4$, filtered, and concentrated by rotary evaporation to provide 0.41 g of the desired product.

Example 35

Preparation of 2,2'-[[3-[N-(2-Hydroxyethyl)-N-ethylamino]phenyl]methylene]bis[4-[[(5-methyl-1H-tetrazol-1-yl)imino]methyl]]phenol The title compound was prepared essentially according to the basic procedure described in Example 34, above; however, (2-bromoethoxy)-tert-butyldimethylsilane was used in step a instead of (3-bromopropoxy)-tert-butyldimethylsilane.

Example 36

Preparation of 2,2'-[[3-[1-(4-Hydroxypiperidinyl)]phenyl]methylene]bis[4-[[(5-methyl-1H-tetrazol-1-yl)imino]methyl]]phenol a. Preparation of:

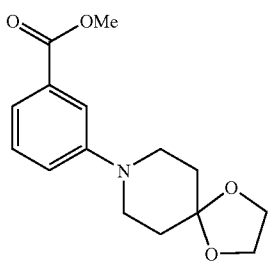

36(a)

A Schlenk flask containing methyl 3-bromobenzoate (5.00 g, 23.3 mmol), tris(dibenzylideneacetone)dipalladium(0) (0.215 g, 0.233 mmol), (S)-binaphthol (0.215 g, 0.345 mmol), and cesium carbonate (10.65 g, 32.7 mmol) was evacuated by vacuum and filled with argon. 1,4-Dioxa-8-azaspiro[4.5]decane (3.65 ml, 28.6 mmol) and toluene (50 ml) were added to the flask. The reaction vessel was closed and heated to 100° C. overnight. Upon completion of the reaction, the mixture was cooled to room temperature and diluted with water. The mixture was extracted with ethyl acetate, dried (MgSO₄), filtered, and concentrated in vacuo. The crude product was purified via column chromatography (silica gel, 25% ethyl acetate in hexanes) to provide 2.37 g of pure product.

b. Preparation of:

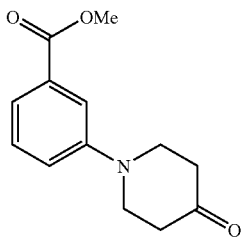

36(b)

Compound 36(a)(2.5 g, 9.0 mmol) was mixed in a solution of 10% sulfuric acid (25 ml) and tetrahydrofuran (12.5 ml) for several days. The solvent was removed in vacuo, and the residue was partitioned between water and ethyl acetate. Saturated sodium bicarbonate was added to the mixture until it was basic. The aqueous layer was extracted two times with ethyl acetate. The combined organics were dried (MgSO₄), filtered, and concentrated in vacuo. The crude product was purified via column chromatography (silica gel, 200 g; 10-30% ethyl acetate in hexanes) to provide 1.24 g of the desired product.

c. Preparation of:

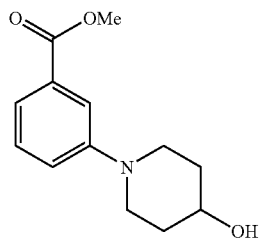

36(c)

Sodium borohydride (92 mg, 2.44 mmol) was added to a chilled (0° C. in ice/NaCl bath) solution of compound 36(b) (1.14 g, 4.89 mmol) in methanol (12 ml). The mixture was stirred for 20 minutes and diluted with water. The solution was extracted with dichloromethane, and the combined organics were dried (MgSO₄), filtered, and dried in vacuo to provide 1.27 g of the desired product. This reaction was repeated and the products were mixed together and taken on to the following step.

d. Preparation of:

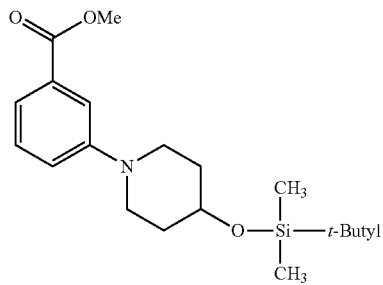

36(d)

Compound 36(c) (1.78 g, 7.6 mmol) was mixed with tert-butyldimethylsilyl chloride (1.26 g, 0.836 mmol), imidazole (0.57 g, 8.36 mmol), and dry dichloromethane (50 ml), and stirred at room temperature for about 16 hours. The mixture was diluted with dichloromethane and washed with water and brine. The organic layer was dried over MgSO₄, filtered, and concentrated in vacuo. The product was purified via column chromatography (silica gel, 300 g; 10% ethyl acetate in hexanes) to provide 1.90 g of the desired product.

e. Preparation of:

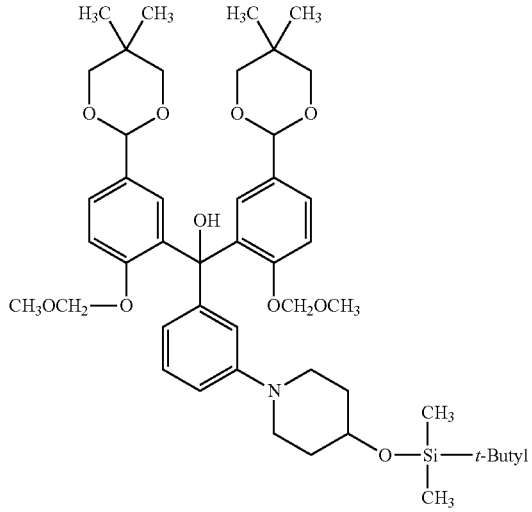

36(e)

2-(4-Methoxymethoxyphenyl)-5,5-dimethyl-1,3-dioxane (4.11 g, 16.3 mmol), prepared according to step b, above, was mixed with dry tetrahydrofuran (50 ml), under argon. N,N, N',N'-Tetramethylethylenediamine (2.46 ml, 16.3 mmol) was added to the solution, and the resulting mixture was cooled to around −10° C. in an ice/NaCl bath. Sec-butyllithium (12.8 ml, 1.4M in cyclohexane, 17.9 mmol) was added dropwise, maintaining the temperature below 0° C. The reaction was stirred for 20 minutes at 0° C., and then a solution of compound 36(d) (1.90 g, 5.44 mmol) in dry tetrahydrofuran (20 ml) was added dropwise to the reaction. After this addition, the solution was stirred for 3 hours at −10° C., then quenched with 20% aqueous $NH_4Cl$. The organic solvents were removed in vacuo. The mixture was extracted two times with ethyl acetate (150 ml). The organic layers were combined, dried with magnesium sulfate, filtered, and concentrated on rotary evaporator. The crude product was chromatographed (silica gel, 15% ethyl acetate in hexanes), yielding 2.60 g of the desired product.

f. Preparation of:

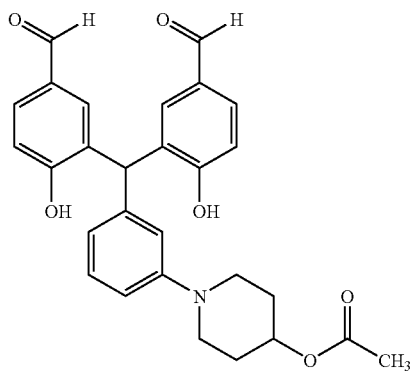

36(f)

Hydriodic acid (2.8 ml, 58 wt % in water) was added to a solution of compound 36(e) (2.3 g, 2.8 mmol) in glacial acetic acid (28 ml). The reaction was stirred at room temperature for about 16 hours. The acetic acid was removed by rotary evaporation. The residue was partitioned between ethyl acetate and water. Sodium thiosulfate was added to remove the iodine. $NaHCO_3$ was added until a pH ~8 was achieved, and NaCl was added to saturate the aqueous layer. The product was extracted into ethyl acetate (3×100 ml), and the combined organics were dried over magnesium sulfate, filtered, and rotary evaporated. The resulting solid was purified by recrystallization (ethyl acetate/hexanes), yielding 1.34 g of the desired product.

g. Preparation of:

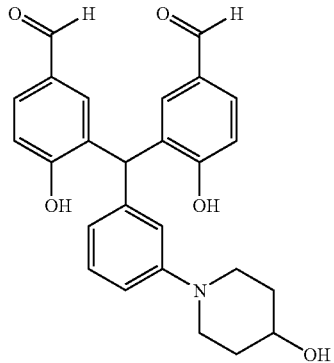

36(g)

Milled potassium carbonate (0.79 g, 5.68 mmol) was added to a solution of compound 36(f) (1.34 g, 2.84 mmol) in methanol (30 ml) and water (1 ml). The reaction was stirred at room temperature for about 16 hours. The solvents were removed by rotary evaporation, and the residue was dissolved in a small amount of water and ethyl acetate. The mixture was neutralized with 1M HCl (~pH 7), and the layers were separated. The aqueous layer was extracted several times with ethyl acetate. The combined organic layers were dried over magnesium sulfate, filtered, and rotary evaporated. The crude product was purified via column chromatography (silica gel, 75-100% ethyl acetate/hexanes) to provide 0.64 g of the desired product.

h. 2,2'-[[3-[1-(4-Hydroxypiperidinyl)]phenyl]methylene] bis[4-[[(5-methyl-1H-tetrazol-1-yl)imino]methyl]]phenol. Compound 36(g) (0.30 g, 0.69 mmol) was dissolved in absolute ethanol (9 ml) and added dropwise to a refluxing solution of 1-amino-5-methyltetrazole (0.207 g, 2.09 mmol) and pyridinium para-toluenesulfonate (0.192 g, 0.765 mmol) in ethanol (9 ml). The reaction was heated to reflux for 3 hours, and then cooled to room temperature. The mixture was diluted with t-butyl methyl ether, and the tosic acid salt of the product was collected by filtration.

The free base was isolated by adding sodium bicarbonate to a suspension of the salt in water and ethyl acetate. The mixture was extracted several times with ethyl acetate, and the combined organics were dried over $MgSO_4$, filtered, and concentrated by rotary evaporation to provide 0.266 g of the desired product.

Example 37

Preparation of 2,2'-[[3-[N-(3-Hydroxypropyl)-N-methylamino]phenyl]methylene]bis[4-[[(5-methyl-1H-tetrazol-1-yl)imino]methyl]]phenol a. Preparation of:

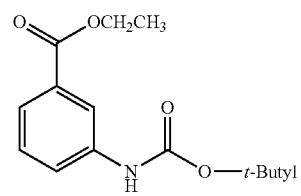

37(a)

Di-tert-butyl dicarbonate (14.5 g, 66.55) was dissolved in tetrahydrofuran (50 ml) and was added to a solution of ethyl 3-aminobenzoate (9.03 ml, 60.5 mmol) and N,N-diisopropylethylamine (11.6 ml, 66.55 mmol) in tetrahydrofuran (50 ml) under argon. The reaction mixture was stirred at room temperature overnight. The mixture was diluted with water and concentrated in vacuo. The residue was diluted with water, and the product was extracted into ethyl acetate, dried with $MgSO_4$, filtered, and concentrated in vacuo. The residue was triturated with hexanes to provide the product as a white solid (15.5 g).

b. Preparation of:

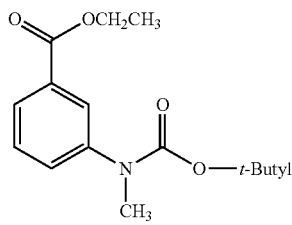

37(b)

Compound 37(a) (14.5 g, 54.65 mmol) was added to a mixture of NaH (1.44 g, 60.12 mmol) in N,N-dimethylformamide (150 ml). After H₂ generation slowed, methyl iodide (4.42 ml, 71.09 mmol) was added, and the reaction was stirred at room temperature for about 16 hours. The reaction mixture was diluted with water and extracted into ethyl acetate. The organic layer was dried over MgSO₄ and concentrated in vacuo, to provide the desired product.

b. Preparation of:

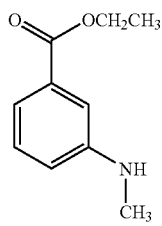

37(c)

4M Hydrochloric acid (46.8 ml) was added to a solution of compound 37(b) (13.07 g, 46.8 mmol) in tetrahydrofuran (150 ml). The reaction mixture was heated to reflux for about 13 hours. The mixture was concentrated in vacuo and dissolved in ethyl acetate. The solution was washed with saturated aqueous NaHCO₃ and brine, dried with MgSO₄, and concentrated in vacuo. The product was purified by flash chromatography (silica gel, ethyl acetate/hexanes) to provide 4.5 g of the desired product.

c. Preparation of:

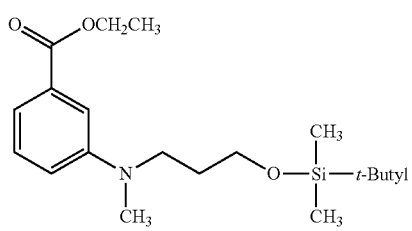

37(d)

A mixture of compound 37(c) (1.5 g, 8.37 mmol), (3-bromopropoxy)-tert-butyldimethylsilane (3.88 ml, 16.74 mmol), N,N-diisopropylethylamine (2.92 ml, 16.74 mmol), sodium iodide (1.88 g, 12.56 mmol) and acetonitrile (4 ml) were separated into four equal portions and sealed into round bottom, glass tubes. The flasks were heated to 140-145° C. in a microwave, while stirring under pressure. The reaction mixtures were combined and diluted with water. The product was extracted with ethyl acetate, dried with MgSO₄, and concentrated in vacuo. The residue was purified via chromatography (two times, silica gel, 5-20% ethyl acetate in hexanes) to provide 1.72 g of the desired product.

d. Preparation of:

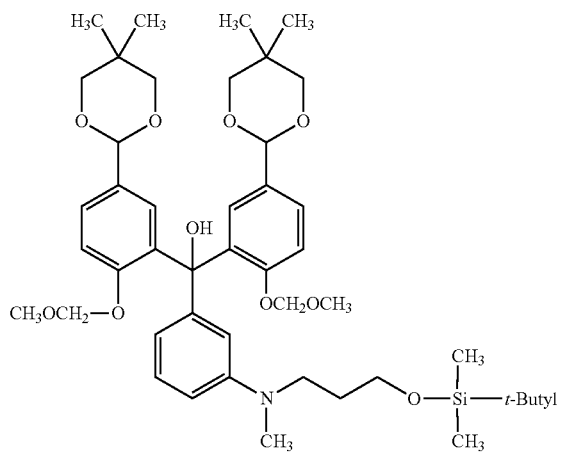

37(e)

2-(4-Methoxymethoxyphenyl)-5,5-dimethyl-1,3-dioxane (3.70 g, 14.67 mmol), prepared according to step b, example 1 above, was mixed with dry tetrahydrofuran (40 ml), under argon. N,N,N',N'-Tetramethylethylenediamine (2.21 ml, 14.67 mmol) was added to the solution, and the resulting mixture was cooled to around –10° C. Sec-butyllithium (12.42 ml, 1.3M in cyclohexane, 16.14 mmol) was added dropwise. The reaction was stirred for 15-20 minutes at –8 to 0° C., and then a solution of compound 37(d) (1.72 g, 4.89 mmol) in dry tetrahydrofuran (20 ml) was added dropwise to the reaction. After this addition, the solution was stirred for 2 to 2.5 hours at –10 to 0° C. The reaction was quenched with saturated aqueous NH₄Cl, and the organic solvents were removed in vacuo. The mixture was extracted with ethyl acetate, washed with saturated aqueous NaCl, dried with magnesium sulfate, filtered, and concentrated on rotary evaporator. The crude product was purified via chromatography (silica gel, 20% ethyl acetate in hexanes) to provide 1.56 g of the desired product.

f. Preparation of:

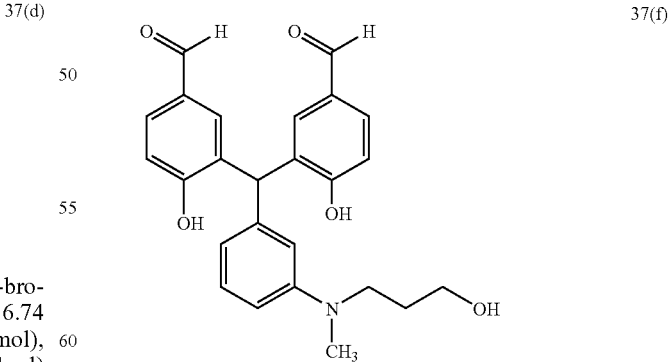

37(f)

Hydriodic acid (1.88 ml, 57 wt % in water) was added to a solution of compound 37(e) (1.55 g, 1.91 mmol) in glacial acetic acid (20 ml). The reaction was stirred at room temperature for 3 hours. The reaction mixture was concentrated in vacuo, and the residue was diluted with water and ethyl acetate, then treated with aqueous sodium thiosulfate. The pH of the aqueous layer was adjusted to pH 7 with sodium bicarbonate, and the mixture was extracted with ethyl acetate. The combined organics were washed with aqueous saturated brine, dried over magnesium sulfate, filtered, and rotary evaporated. The resulting solid was purified via flash chromatography (silica gel, 50-80% ethyl acetate in hexanes), yielding 0.28 g of the intermediate product.

The product was treated with potassium carbonate (0.55 g) in a solution of methanol and water (12:1), and was stirred at room temperature overnight. The methanol was removed by rotary evaporation, and the mixture was again stirred at room temperature for about 16 hours. The pH of the mixture was adjusted to ~pH 7 with 1N HCl. The product was extracted with ethyl acetate, dried over MgSO$_4$, and concentrated in vacuo. The residue was purified via flash chromatography (silica gel, ethyl acetate/hexanes) to provide 0.2 g of the desired product.

g. 2,2'-[[3-[N-(3-Hydroxypropyl)-N-methylamino]phenyl]methylene]bis[4-[[(5-methyl-1H-tetrazol-1-yl)imino]methyl]]phenol. 1-Amino-5-methyltetrazole (71 mg, 0.72 mmol) and pyridinium para-toluenesulfonate (6 mg, 0.024 mmol) were dissolved in absolute ethanol (10 ml) and heated to reflux for 15 minutes. Compound 37(f) (0.17 g, 0.41 mmol) in ethanol (6 ml) was added dropwise to the solution. The reaction was stirred at reflux for 3 hours, and then cooled to room temperature overnight. The solvent was removed in vacuo and diluted with t-butyl methyl ether to provide the tosic acid salt, which was isolated by filtration and dried in vacuo. This solid was treated with sodium bicarbonate (20 mg) in water (6 to 7 ml) and ethyl acetate to form the free base. The layers were separated, and the aqueous layer was extracted with ethyl acetate. The combined organics were dried over MgSO$_4$, filtered, and concentrated by rotary evaporation to provide 0.12 g of the desired product.

Example 38

Preparation of 2,2'-[[3-[N-(4-Acetoxybutyl)-N-ethylamino]phenyl]methylene]bis[4-[[(5-methyl-1H-tetrazol-1-yl)imino]methyl]]phenol The title compound (0.186 g) was prepared essentially according to the procedure described in Example 21, above; however, step e of example 21 was omitted.

Example 39

Preparation of 2,2'-[[3-[N-(2-Hydroxyethyl)-N-methylamino]phenyl]methylene]bis[4-[[(5-methyl-1H-tetrazol-1-yl)imino]methyl]]phenol The title compound (20 mg) was prepared essentially according to the basic procedure described in Example 37; however, (2-bromoethoxy)-tert-butyldimethylsilane was used in step d instead of (3-bromopropoxy)-tert-butyldimethylsilane.

Example 40

Preparation of 2,2'-[[3[N-(4-Hydroxybutyl)-N-methylamino]phenyl]methylene]bis[4-[[(5-methyl-1H-tetrazol-1-yl)imino]methyl]]phenol The title compound (20 mg) was prepared essentially according to the basic procedure described in Example 37; however, tert-butyl-(4-iodobutoxy)dimethylsilane was used in step d instead of (3-bromopropoxy)-tert-butyldimethylsilane.

Example 41

Preparation of 2,2'-[[3-[N-(2-Hydroxyethyl)-N-propylamino]phenyl]methylene]bis[4-[[(5-methyl-1H-tetrazol-1-yl)imino]methyl]]phenol a. Preparation of:

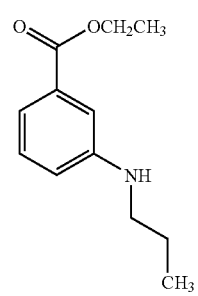

41(a)

Ethyl 3-aminobenzoate (15 g, 91 mmol) was added to a mixture of Raney Nickel (30 g) in propanol (300 ml). The mixture was heated to reflux for about 16 hours. The reaction mixture was cooled to room temperature, filtered through Celite, and concentrated by rotary evaporation. The crude product was dissolved in ethyl acetate, washed with brine, dried with MgSO$_4$, filtered, and concentrated in vacuo. The product was purified via column chromatography (silica gel, 5% ethyl acetate in hexanes) to provide 13.83 g of the desired product as a white solid.

e. Preparation of:

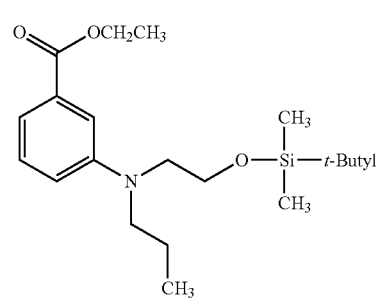

41(b)

(2-Bromoethoxy)-tert-butyldimethylsilane (20.7 ml, 96 mmol) and diisopropylethylamine (12.2 ml, 72 mmol) were added to a solution of compound 41(a) (5.0 g, 24 mmol) in acetonitrile (100 ml), then heated to reflux for two days. The mixture was cooled to room temperature and stirred for several days. The reaction mixture was partitioned between water and ethyl acetate. The organic layer was washed with water (3×) and rotary evaporated. The crude product was purified via column chromatography (silica gel, 1% ethyl acetate in hexanes) to provide 2.31 g of the desired product.

f. Preparation of:

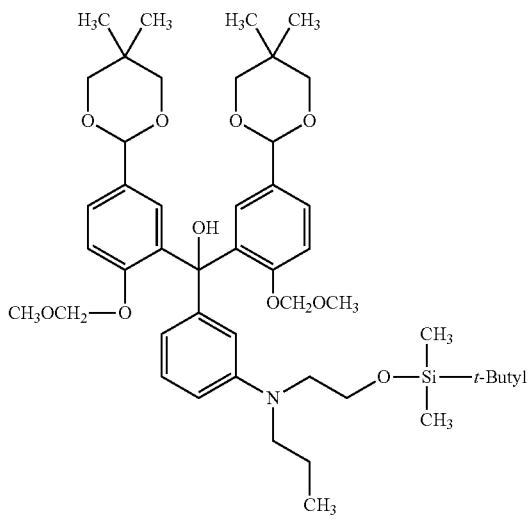

2-(4-Methoxymethoxyphenyl)-5,5-dimethyl-1,3-dioxane (4.78 g, 18.46 mmol), prepared according to step b, example 1 above, was mixed with dry tetrahydrofuran (60 ml), under argon. N,N,N',N'-Tetramethylethylenediamine (2.87 ml, 20.86 mmol) was added to the solution, and the resulting mixture was cooled to around −10° C. Sec-butyllithium (16 ml, 1.3M in cyclohexane, 20.86 mmol) was added dropwise. The reaction was stirred for 15-20 minutes, and then a solution of compound 41(b) (2.31 g, 6.32 mmol) in dry tetrahydrofuran (20 ml) was added dropwise to the reaction. After this addition, the solution was stirred for 3 hours at −15 to 0° C. The reaction was quenched with saturated aqueous $NH_4Cl$ (10 ml), and the organic solvents were removed in vacuo. The mixture was extracted with ethyl acetate, washed with saturated aqueous NaCl, dried with magnesium sulfate, filtered, and concentrated on rotary evaporator. The crude product was purified via chromatography (silica gel, 20%-30% ethyl acetate in hexanes) to provide 1.42 g of the desired product.

g. Preparation of:

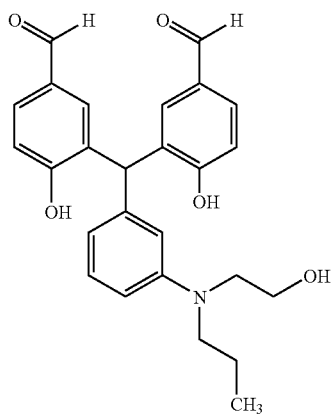

Hydriodic acid (1.40 ml, 57 wt % in water, 10.49 mmol) was added to a solution of compound 41(c) (1.92 g, 2.33 mmol) in glacial acetic acid (20 ml). The reaction was stirred at room temperature for ~4 hours. The reaction mixture was concentrated in vacuo to about ⅔ the volume, and the residue was diluted with water and ethyl acetate, then treated with aqueous sodium thiosulfate. The pH of the aqueous layer was adjusted to pH 7 with sodium bicarbonate, and the layers were separated. The aqueous layer was extracted with ethyl acetate. The combined organics were washed with aqueous saturated brine, dried over magnesium sulfate, filtered, and rotary evaporated. The residue was diluted with ethyl acetate, and a solid was precipitated with hexanes. The solid was isolated by filtration and dried under vacuum.

The product was treated with potassium carbonate in a solution of methanol and water (12:1) and was stirred at room temperature overnight. The methanol was removed by rotary evaporation, and the remaining mixture was partitioned between water and ethyl acetate. The aqueous layer was neutralized with 1M HCl. The organic layers were combined, dried over $MgSO_4$, and concentrated in vacuo to provide 0.488 g of the desired product.

e. 2,2'-[[3-[N-(2-Hydroxyethyl)-N-propyl]amino]phenyl]methylene]bis[4-[[(5-methyl-1H-tetrazol-1-yl)imino]methyl]]phenol. The title compound (0.33 g) was then prepared essentially according to the basic procedure described in Example 37 step g; however, compound 41(d) was used instead of compound 37(f).

Example 42

Preparation of 2,2'-[[3-[N-(4-Hydroxybutyl)-N-propylamino]phenyl]methylene]bis[4-[[(5-methyl-1H-tetrazol-1-yl)imino]methyl]]phenol The tosic acid salt of the title compound was prepared essentially according to the basic procedure described in Example 41; however, tert-butyl-(4-iodobutoxy)dimethylsilane was used in step b instead of (2-bromoethoxy)-tert-butyldimethylsilane.

The free base was isolated by treating a solution of the salt in ethyl acetate and water with sodium bicarbonate, then washing the product with McIlvans pH 6 buffer to provide the desired product.

Example 43

Preparation of 2,2'-[[3-[N-(6-Hydroxyhexyl)-N-ethylamino]phenyl]methylene]bis[4-[[(5-methyl-1H-tetrazol-1-yl)imino]methyl]]phenol The title compound (0.98 g) was prepared essentially according to the basic procedure described in Example 41 steps b-e; however, compound 21(a) was used instead of compound 41(a) and (6-bromohexyloxy)-tert-butyldimethylsilane was used instead of (2-bromoethoxy)-tert-butyldimethylsilane in step b.

Example 44

Preparation of 2,2'-[[3-[N-(5-Hydroxypentyl)-N-ethylamino]phenyl]methylene]bis[4-[[(5-methyl-1H-tetrazol-1-yl)imino]methyl]]phenol a. Preparation of.

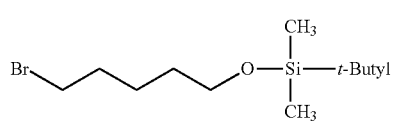
44(a)

A mixture of 5-bromo-1-pentanol (25 g, 0.15 mol), imidazole (24.8 g, 0.165 mol), tert-butyldimethylsilyl chloride (24.8 g, 0.165 mol), and dichloromethane (100 ml) was stirred at room temperature, under argon, overnight. The solid was removed by filtration. The filtrate was washed with water (2×), dried with $MgSO_4$, filtered through Celite, and concentrated on rotary evaporator to provide 38 g of desired product.

b. 2,2'-[[3-[N-(5-Hydroxypentyl)-N-ethylamino]phenyl]methylene]bis[4-[[(5-methyl-1H-tetrazol-1-yl)imino]methyl]]phenol. The title compound (0.98 g) was prepared essentially according to the basic procedure described in Example 41 steps b-e; however, compound 21(a) was used instead of compound 41(a), and compound 44(a) was used instead of (2-bromoethoxy)-tert-butyldimethylsilane in step b.

Other compounds of the invention having anti-pneumovirus activity may be prepared following the various synthetic routes described hereinabove. Examples include, without limitation the compounds of Tables 1 and 2:

TABLE 1

| Example # | $R_1$ | Name |
|---|---|---|
| 1. | —$CH_2CF_3$ | 2,2'-[[3-(2,2,2-Trifluoroethyl)phenyl]methylene]bis[4-[[(5-methyl-1H tetrazol-1-yl)imino]methyl]]phenol |
| 2. | —$CH_2CH_2OCCH_3$ (O) | 3-[[Bis[[5-(5-methyl-1H-tetrazol-1-yl)imino]methyl]-2-hydroxyphenyl]methylene] benzeneethanol, acetate ester |
| 3. | —$CH_2CH_2OH$ | 3-[[Bis[[5-(5-methyl-1H-tetrazol-1-yl)imino]methyl]-2-hydroxyphenyl]methylene] benzeneethanol |
| 4. | —N(morpholinyl) | 2,2'-[[3-(4-Morpholinyl)phenyl)methylene] bis[4-[[(5-methyl-1H-tetrazol-1-yl)imino]methyl]]phenol |
| 5. | —N(piperidinyl) | 2,2'-[[3-(1-Piperidinyl)phenyl]methylene] bis[4-[[(5-methyl-1H-tetrazol-1-yl)imino]methyl]]phenol |
| 6. | —$SO_2N(CH_2CH_2OCH_3)_2$ | 3-[[Bis[[5-(5-methyl-1H-tetrazol-1-yl)imino]methyl)-2-hydroxyphenyl]methylene]-N,N-bis(methoxyethyl)benzenesulfonamide |

TABLE 1-continued

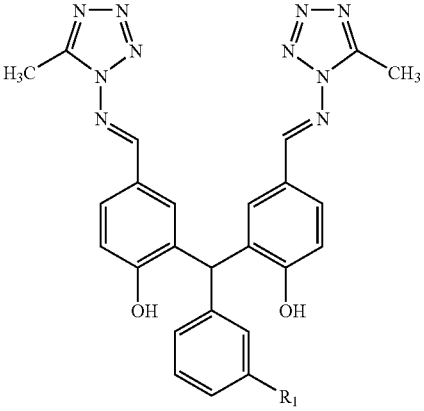

| | | |
|---|---|---|
| 7. | 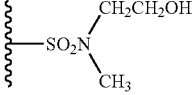 | 3-[[Bis[[5-(5-methyl-1H-tetrazol-1-yl)imino]methyl]-2-hydroxyphenyl]methylene]-N-(hydroxyethyl)-N-methylbenzenesulfonamide |
| 8. | —(CH$_2$)$_3$OH | 3-[[Bis[[5-(5-methyl-1H-tetrazol-1-yl)imino]methyl]-2-hydroxyphenyl]methylene] benzenepropanol |
| 9. | 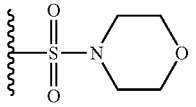 | 2,2'-[[3-(4-Morpholinylsulfonyl)phenyl] methylene]bis[4-[[(5-methyl-1H-tetrazol-1-yl)imino]methyl]]phenol |
| 10. | —OCH$_2$CH$_2$OCH$_3$ | 2,2'-[[3-(Methoxyethoxy)phenyl]methylene] bis[4-[[(5-methyl-1H-tetrazol-1-yl)imino]methyl]]phenol |
| 11. | 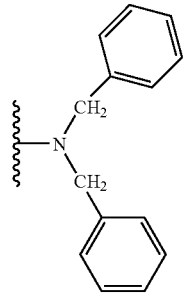 | 2,2'-[[3-Bis(phenylmethyl)amino]phenyl] methylene]bis]4-[[(5-methyl-1H-tetrazol-1-yl)imino]methyl]]phenol |
| 12. | 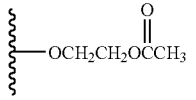 | 3-[[Bis[[5-(5-metbyl-1H-tetrazol-1-yl)imino]methyl]-2-hydroxyphenyl]methylene] phenoxyethanol, acetate ester |
| 13. | 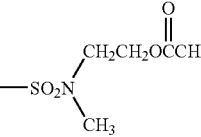 | 3-[[Bis[[5-(5-methyl-1H-tetrazol-1-yl)imino]methyl]-2-hydroxyphenyl]methylene]-N-(acetoxyethyl)-N-methylbenzenesulfonamide |
| 14. | —OCH$_2$CH$_2$OH | 3-[[Bis[[5-(5-methyl-1H-tetrazol-1-yl)imino]methyl]-2-hydroxyphenyl]methylene] phenoxyethanol |

TABLE 1-continued

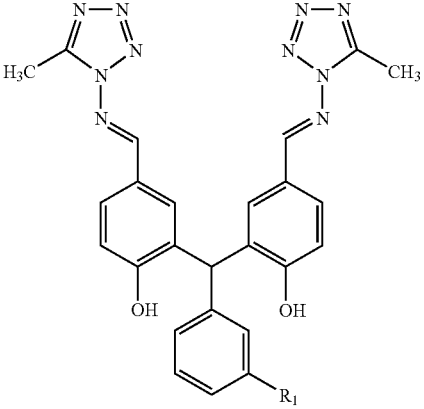

| | | |
|---|---|---|
| 15. | 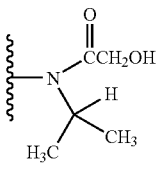 | 2-Hydroxy-N-[[3-[bis[[5-(5-methyl-1H-tetrazol-1-yl)imino]methyl]-2-hydroxylphenyl]methylene]phenyl]-N-(methylethyl)acetamide |
| 16. | 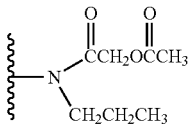 | 2-(Acetyloxy)-N-[3-[[bis[[5-(5-methyl-1H-tetrazol-1-yl)imino]methyl]-2-hydroxyphenyl]methylene]phenyl]-N-propylacetamide |
| 17. | 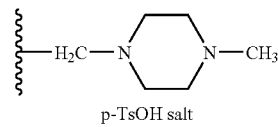<br>p-TsOH salt | 2,2'-[[3-[1-(4-Methylpiperazinyl)methyl]phenyl]methylene]bis[4-[[(5-methyl-1H-tetrazol-1-yl)imino]methyl]]phenol |
| 18. | 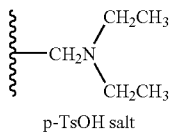<br>p-TsOH salt | 2,2'-[[3-(Diethylaminomethyl)phenyl]methylene]bis[4-[[(5-methyl-1H-tetrazol-1-yl)imino]methyl]]phenol |
| 19. | 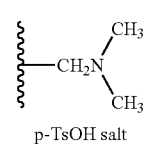<br>p-TsOH salt | 2,2'-[[3-(Dimethylaminomethyl)phenyl]methylene]bis [4-[[(5-methyl-1H-tetrazol-1-yl)imino]methyl]]phenol |
| 20. | 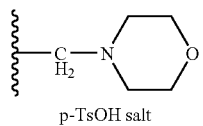<br>p-TsOH salt | 2,2'-[[3-[4-(Morpholinyl)methyl]phenyl]methylene]bis[4-[[(5-methyl-1H-tetrazol-1-yl)imino]methyl]]phenol |
| 21. | 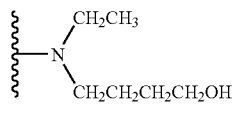 | 2,2'-[[3-[N-(4-Hydroxybutyl)-N-ethylamino]phenyl]methylene]bis[4-[[5-methyl-1H-tetrazol-1-yl)imino]methyl]]phenol |
| 22. | 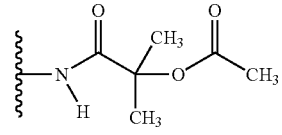 | 2-(Acetyloxy)-N-[3-[[Bis[[5-(5-methyl-1H-tetrazol-1-yl)imino]methyl]-2-hydroxyphenyl]methylene]phenyl]-2-methylpropanamide |

TABLE 1-continued

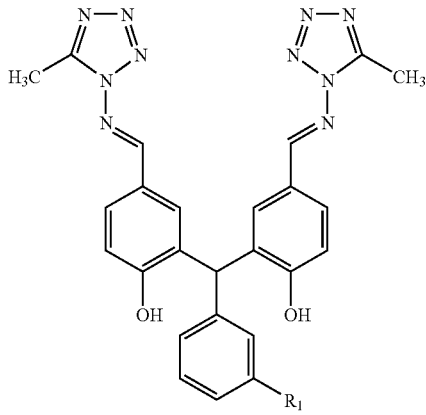

| | | |
|---|---|---|
| 23. | [structure: -NH-C(=O)-CH2OCH3] | N-[3-[[Bis[[5-(5-methyl-1H-tetrazol-1-yl)imino]methyl]-2-hydroxylphenyl]methylene]phenyl]-2-methoxyacetamide |
| 24. | [structure: -NH-C(=O)-cyclopropyl] | N-[3-[[Bis[[5-(5-methyl-1H-tetrazol-1-yl)imino]methyl]-2-hydroxylphenyl]methylene]phenyl]-cyclopropanecarboxamide |
| 25. | [structure: -N(SO2CH2CH2CH2CH3)2] | N-[3-[[Bis[[5-(5-methyl-1H-tetrazol-1-yl)imino]methyl]-2-hydroxylphenyl]methylene]phenyl-N-(butylsulfonyl)butane sulfonamide |
| 26. | [structure: -N(SO2CH2CF3)2] | N-[3-[[Bis[]5-(5-methyl-1H-tetrazol-1-yl)imino]methyl]-2-hydroxylphenyl]methylene]phenyl]-N-(2,2,2-trifluoraethylsulfonyl)-2,2,2-trifluoroethane sulfonamide |
| 27. | [structure: -NH-C(=O)-C(CH3)2OH] | N-[3-[[Bis[[5-(5-methyl-1H-tetrazol-1-yl)imino]methyl]-2-hydroxylphenyl]methylene]phenyl]-2-hydroxy-2-methyl-propanamide |
| 28. | [structure: -N(SO2CH2CH2CH3)2] | N-13-[[Bis[[5-(5-methyl-1H-tetrazol-1-yl)imino]methyl]-2-hydroxylphenyl]methylene]phenyl]-N-(propylsulfonyl)propane sulfonamide |
| 29. | [structure: -N(SO2CH2CH2CH2Cl)2] | N-[3-[[Bis[[5-(5-methyl-1H-tetrazol-1-yl)imino]methyl]-2-hydroxylphenyl]methylene]phenyl]-N-chloropropylsulfonyl)-3-chloropropane sulfonamide |
| 30. | [structure: -NH-C(=O)-CH2OC(=O)CH3] | 2-(Acetyloxy)-N-[3-[[bis[[5-(5-methyl-1H-tetrazol-1-yl)imino]methyl]-2-hydroxyphenyl]methylene]phenyl]acetamide |

TABLE 1-continued

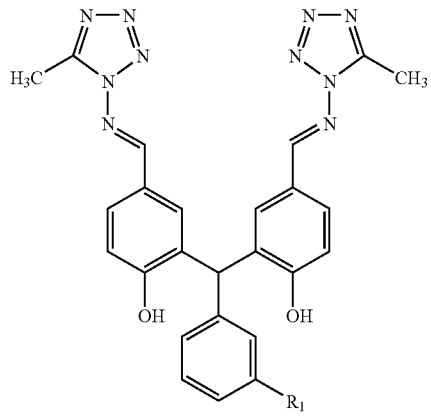

| | | |
|---|---|---|
| 31. | ⁓N(SO₂CH₃)(SO₂CH₃) | N-[3-[[Bis[[5-(5-methyl-1H-tetrazol-1-yl)imino]methyl]-2-hydroxylphenyl]methylene]phenyl]-N-(methylsulfonyl)methane sulfonamide |
| 32. | ⁓N(isothiazolidine 1,1-dioxide) | 2,2'-[[3-[2-(1,1-Dioxide-2,3,4,5-tetrahydro)isothiazolyl]phenyl]methylene]bis[4-[(5-methyl-1H-tetrazol-1-yl)imino]methyl]phenol |
| 33. | ⁓NH-C(O)CH₂OH | 2-Hydroxy-N-[3-[[bis[[5-(5-methyl-1H-tetrazol-1-yl)imino]methyl]-2-hydroxylphenyl]methylene]phenyl]acetamide |
| 34. | ⁓N(CH₂CH₃)(CH₂CH₂CH₂OH) | 2,2'[[3-[N-(3-Hydroxypropyl)-N-ethylamino]phenyl]methylene]bis[4-[[(5-methyl-1H-tetrazol-1-yl)imino]methyl]]phenol |
| 35. | ⁓N(CH₂CH₃)(CH₂CH₂OH) | 2,2'-[[3-[N-(2-Hydroxyethyl)-N-ethylamino]phenyl]methylene]bis[4-[[(5-methyl-1H-tetrazol-1-yl)imino]methyl]]phenol |
| 36. | ⁓N(4-hydroxypiperidinyl) | 2,2'-[[3-[1-(4-Hydroxypiperidinyl)]phenyl]methylene]bis[4-[[(5-methyl-1H-tetrazol-1-yl)imino]methyl]]phenol |
| 37. | ⁓N(CH₃)(CH₂CH₂CH₂OH) | 2,2'-[[3-[N-(3-Hydroxypropyl)-N-methylamino]phenyl]methylene]bis[4-[[(5-methyl-1H-tetrazol-1-yl)imino]methyl]]phenol |
| 38. | ⁓N(CH₂CH₃)(CH₂CH₂CH₂CH₂OC(O)CH₃) | 2,2'-[[3-[N-(4-Acetoxybutyl)-N-ethylamino]phenyl]methylene]bis[4-[[5-methyl-1H-tetrazol-1-yl)imino]methyl]]phenol |
| 39. | ⁓N(CH₃)(CH₂CH₂OH) | 2,2'-[[3-[N-(2-Hydroxyethyl)-N-methylamino]phenyl]methylene]bis[4-[[(5-methyl-1H-tetrazol-1-yl)imino]methyl]]phenol |

TABLE 1-continued

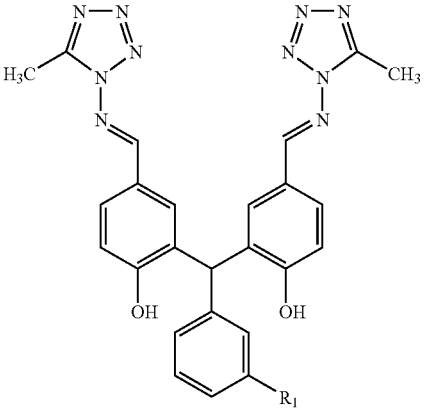

| | | |
|---|---|---|
| 40. | 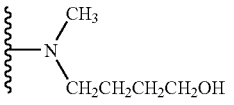 | 2,2'[[3-[N-(4-Hydroxybutyl)-N-methylamino]phenyl]methylene]bis[4-[[(5-methyl-1H-tetrazol-1-yl)imino]methyl]]phenol |
| 41. | 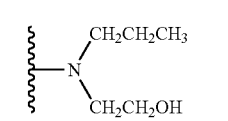 | 2,2'-[[3-[N-(2-Hydroxyethyl)-N-propylamino]phenyl]methylene]bis[4-[[(5-methyl-1H-tetrazol-1-yl)imino]methyl]]phenol |
| 42. | 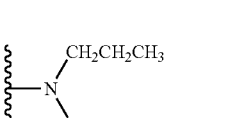 | 2,2'-[[3-[N-(4-Hydroxybutyl)-N-propylamino]phenyl]methylene]bis[4-[[(5-methyl-1H-tetrazol-1-yl)imino]methyl]]phenol |
| 43. | 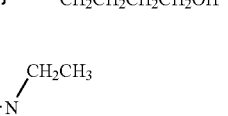 | 2,2-[[3-[N-(6-Hydroxyhexyl)-N-ethylamino]phenyl]methylene]bis[4-[[(5-methyl-1H-tetrazol-1-yl)imino]methyl]]phenol |
| 44. | 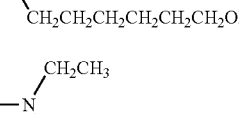 | 2,2'-[[3-[N-(5-Hydroxypentyl)-N-ethylamino]phenyl]methylene]bis[4-[[(5-methyl-1H-tetrazol-1-yl)imino]methyl]]phenol |

| Example # | NMR Data* | Mass Spec. |
|---|---|---|
| 1. | $^1$H NMR in DMSO: 10.51 (s, 2H); 9.15 (s, 2H); 7.80 (dd, 2H, J=1.76, 8.21 Hz); 7.46 (d, 2H, J=1.76 Hz); 7.34 (m, 1H);7.22 (m, 1H); 7.13 (s, 1H); 7.08 (d, (q, 2H, J=11.72 Hz); 2.45 (s, 6H) | 575 |
| 2. | $^1$H NMR in DMSO: 1052 (s, 2H); 9.15 (s, 2H); 7.80 (dd, J = 2.3, 1.7, 8.8, 8.2 Hz, 2H); 7.45 (d, J = 1.7 Hz, 2H); 7.26 (t, J = 7.6 Hz., 1H); 7.13 (d, J = 7.6 Hz, 1H); 6.98 (m, 4H); 6.06 (s, 1H); 4.15 (t, J = 7.0, 6.4 Hz, 2H); 2.83 (t, J = 6.4, 7.0 Hz, 2H); 2.45 (s, 6H); 1.85 (s, 3H) | 581 |
| 3. | $^1$H NMR in DMSO: 10.52 (s, 2H); 9.15 (s, 2H); 7.80 (dd, J=1.7, 2.3, 8.5 Hz, 2H); 7.48 (d, J=1.7 Hz, 2H); 7.22 (t, J=7.6 Hz, 1H); 7.09 (d, J=7.6 Hz, 1H); 6.96 (m, 4H); 6.06 (s, 1H); 3.55 (t, J=7.6, 7.0 Hz, 2H); 2.67 (t, J=7.0 Hz, 2H); 2.46 (s, 6H) | 537 |
| 4. | $^1$H NMR in DMSO: 10.52 (s, 2H); 9.16 (s, 2H); 7.80 (d, 2H, J = 8.21); 7.49 (s, 2H); 7.18 (t, 1H, J = 7.62); 6.98 (d, 2H, J = 8.21); 6.82 (d, 1H, J = 8.79): 6.71 (s, 1H); 6.54 (d, 1H, J = 7.03); 6.02 (s, 1H); 3.68 (bs, 4H); 3.03 (bs, 4H); 2.47 (s, 6H) | 579 |

TABLE 1-continued

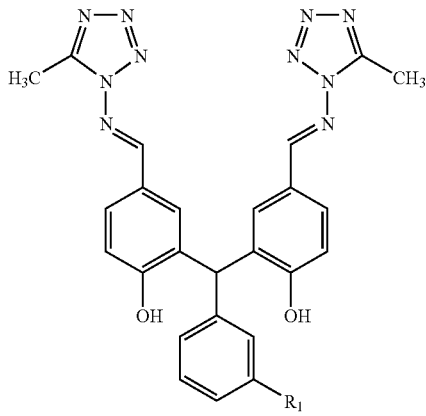

| | | |
|---|---|---|
| 5. | ¹H NMR in DMSO: 10.55 (s, 2H); 9.16 (s, 2H); 7.83 (dd, J=1.8, 7.0 Hz, 2H); 750 (s, 3H); 725 (m, 1H); 7.12 (d, J=7.6 Hz, 1H); 7.02 (d, J=8.2 Hz, 3H); 6.06 (s, 1H); 3.35 (m, 4H); 1.65 (m, 4H); 1.54 (m, 2H) | 578 578 |
| 6. | ¹H NMR in DMSO: 10.65 (s, 2H); 9.18 (s, 2H); 7.85 (dd, 2H, J= 8.21, 2.34); 7.71 (d, 1H, J=8.21); 7.57 (t, 1H, J= 8.21); 7.47 (d, 3H, J=2.34); 7.41 (d, 1H, J= 7.62); 7.04 (d, 2H, J=8.21); 6.15 (s, 1H); 3.31 (m, 4H); 3.23 (m, 4H); 3.09 (s, 6H); 2.47 (s, 6H) ¹³C NMR (75 MHz, DMSO) 160.55, 159.44, 149.93, 144.55, 140.22, 133.93, 131.70, 130.86, 130.43, 130.11, 127.53, 125.48, 123.03, 116.69, 71.01, 58.55, 48.32, 43.65, 8.76 | 688 |
| 7. | ¹H NMR in DMSO: 10.64 (brs, 2H); 9.16 (s, 2H); 7.84 (dd, 2H, J= 8.21, 1.76); 7.63 (6, 1H, J=8.21); 7.58 (t, 1H, J=7.62); 7.45 (d, 2H, J=1.76); 7.40 (d, 2H, J= 1.76); 7.02 (6, 2H, J=8.21); 6.13 (s, 1H); 3.45 (m, 2H); 2.88 (t, 2H, J=5.86); 2.61 (s, 3H); 2.44 (s, 6H) ¹³C NMR (75 MHz, DMSO) 160.56, 159.49, 149.93, 144.65, 137.63, 134.08, 131.63, 130.98, 130.40, 130.16, 127.72, 125.65, 123.06, 116.66, 59.72, 52.65, 3.74, 36.25, 8.77 | 630 |
| 8. | ¹H NMR in DMSO: 10.51 (s, 2H); 9.15 (s, 2H); 7.79 (dd, J=1.8, 8.4Hz, 2H); 7.47 (6, J=2.2 Hz, 2H); 7.22 (t, J=7.9, 7.5 Hz, 1H) 7.07 (d, J=7.5 Hz, 1H); 6.99 (d, J=8.4 Hz, 2H); 6.93 (s, 1H); 6.90 (d, J=7.5 Hz, 2H); 6.05 (s, 1H); 4.37 (bs, 1H); 3.37 (bs, 2H); 2.55 (m, H); 2.46 (s, 6H); 1.66 (m, 2H) | — |
| 9. | ¹H NMR in DMSO: 10.68 (brs, 2H); 9.18 (s, 2H); 7.86 (dd, 2H, J= 8.21, 1.76); 7.63 (m, 2H); 7.46 (m, 3H); 7.37 (s, 1H); 7.04 (6, 2H, J=8.79); 6.14 (s, 1H); 3.51 (m, 4H); 2.75 (m, 4H); 2.46 (s, 6H) ¹³C NMR (75 MHz, DMSO) 160.58, 159.42, 149.92, 144.86, 134.97, 134.49, 13159, 131.07, 130.33, 130.20, 128.40, 126.21, 123.07, 116.64, 65.89, 46.50, 43.91, 8.77 | 642 |
| 10. | ¹H NMR in DMSO: 10.51 (s, 2H); 9.14 (s, 2H); 7.79 (dd, 2H, J=8.21, 2.34); 7.46 (s, 2H); 7.22 (t, 1H, J= 8.21); 6.99 (d, 2H, J=8.21); 6.81 (dd, 1H, J=7.62, 2.34); 6.68 (d, 1H, J=7.62); 6.57 (m, 1H); 6.03 (s, 1H); 4.00 (m, 2H); 3.58 (m, 2H); 3.23 (s. 3H); 2.45 (s, 6H); ¹³C NMR (75 MHz, DMSO) 160.52, 159.57, 159.17, 149.89, 144.61, 131.80, 131.28, 130.47, 130.02, 122.84, 122.35, | 569 |

TABLE 1-continued

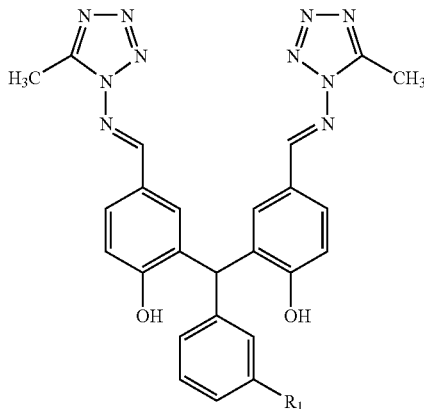

| | | |
|---|---|---|
| | 116.54, 112.15, 71.06, 67.42, 58.79, 43.33, 8.77 | |
| 11. | ¹H NMR in DMSO:<br>10.42 (s, 2H); 9.03 (s, 2H); 7.76 (dd, 2H, J= 8.21, 1.76); 7.24 (d, 2H, J=1.76); 7.20–7.10 (m, 10H); 7.03 (t, 1H, J=7.62); 6.94 (d, 2H, J= 8.21); 6.56 (d, 1H, J=7.62); 6.40 (m, 2H); 5.94 (s, 1H); 4.58 (s, 4H); 2.48 (s, 6H)<br>¹³C NMR (75 MHz, DMSO)<br>160.43, 159.45, 149.90, 148.89, 143.33, 139.63, 131.84, 131.57, 130.04, 129.57, 128.95, 127.31, 127.25, 122.58, 118.22, 116.46, 114.38, 111.19, 55.28, 43.21, 8.81 | 688 |
| 12. | ¹H NMR in DMSO:<br>10.52 (s, 2H); 9.14 (s, 2H); 7.80 (dd, 2H, J= 8.21, 1.76); 7.46 (d, 2H, J=1.76); 7.23 (t, 1H, J=7.62); 6.99 (d, 2H, J=8.21); 6.83 (d, 1H, J= 8.21); 6.69 (t, 1H, J=8.21); 6.60 (s, 1H); 6.03 (s, 1H); 4.26 (m, 2H); 4.10 (m, 2H); 2.45 (s, 6H); 1.97 (s, 3H)<br>¹³C NMR (75 MHz, DMSO)<br>170.98, 160.52, 159.57, 158.92, 149.89, 144.71, 131.85, 131.22, 130.43, 130.07, 122.85, 122.57, 116.56, 116.49, 112.33, 66.32, 63.23, 43.37, 21.28, 8.77 | 596 |
| 13. | ¹H NMR in DMSO:<br>10.64 (s, 2H); 9.17 (s, 2H); 7.84 (dd, 2H, J= 8.21, 1.76); 7.65 (d, 1H, J=8.21); 7.58 (t, 1H, J=7.62); 7.45 (d, 2H, J=1.76); 7.41 (m, 2H); 7.02 (d, 2H, J=8.21); 6.13 (s, 1H); 4.03 (t, 2H, J=5.27); 3.11 (t, 2H, J=5.27); 2.62 (s, 3H); 2.45 (s, 6H); 1.92 (s, 3H)<br>¹³C NMR (75 MHz, DMSO)<br>170.75, 160.56, 159.49, 149.92, 144.74, 137.72, 134.20, 131.72, 130.89, 130.35, 130.26, 127.74, 125.61, 123.06, 116.69, 61.71, 49.10, 43.75, 35.92, 21.21, 8.78 | 673 |
| 14. | ¹H NMR in DMSO:<br>10.52 (brs, 2H); 9.14 (s, 2H); 7.79 (dd, 2H, J= 8.21, 1.76); 7.46 (d, 2H, J=1.76); 7.22 (t, 1H, J=7.62); 6.98 (d, 2H, J=8.21); 6.80 (dd, 1H, 8.21, 2.34); 6.67 (d, 1H, J=7.62); 6.57 (s, 1H); 6.03 (s, 1H); 4.75 (t, 1H, J=5.28); 3.89 (t, 2H, J=5.28); 3.64 (m, 2H); 2.45 (s, 6H)<br>¹³C NMR (75 MHz, DMSO)<br>160.53, 159.56, 159.39, 149.90, 144.57, 131.79, 131.30, 130.48, 130.01, 122.85, 122.22, 116.61, 116.54, 112.08, 70.05, 60.23, 43.34, 8.78 | 555 |
| 15. | ¹H NMR in DMSO:<br>10.56 (brs, 2H); 9.14 (s, 2H); 7.79 (dd, 2H, J=8.21, 2.34); 7.41 (m, 3H); 7.12 (m, 2H); 7.00 (d, 2H, J=8.21); 6.82 (s, 1H); 6.06 (s, 1H); 4.7 (m, 1H); 4.32 (t, 1H, J=5.86); 3.47 (brs, 2H); 2.43 (s, 6H); 0.90 (brs, 6H) | 608 |
| 16. | ¹H NMR in DMSO:<br>10.56 (brs, 2H); 9.12 (s, 2H); 7.80 (dd, 2H, J=8.21, 1.76); 7.42 (m, 3H); 7.22 (m, 1H); 7.06 | 650 |

TABLE 1-continued

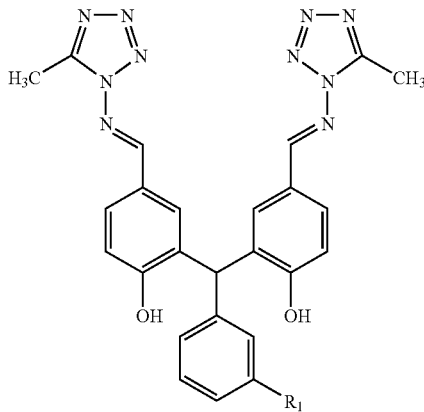

| | | |
|---|---|---|
| | (d, 2H, J=7.62); 7.00 (d, 2H, J=8.79); 6.07 (s, 1H); 4.23 (brs, 2H); 3.50 (t, 2H, J=7.03); 2.42 s, 6H); 1.83 (brs, 3H); 1.32 (m, 2H); 0.71 (t, 3H, J=7.03) | |
| 17. | $^1$H NMR in DMSO: 10.56 (2H, s); 9.15 (2H, s); 7.83 (2H, dd, J=2.0,8.2); 7.47 (2H, d, J=8.2); 7.44 (2H, d, J=2.4); 7.1 (2H, d, J=8.2); 7.01 (2H, d, J=8.2); 6.09 (1H, s); 3.5 (br s, 2H); 2.9 (br s, 2H); 2.7 (br s, 2H); 2.5 (3H, s) | 605 |
| 18. | $^1$H NMR in DMSO: 10.6 (1H, s); 9.16 (2H, s); 7.85 (dd, 2H, J=2, 8.8); 7.45 (7H, m, J=8.21); 7.07 (5H, m, J=8.21, 8.8); 6.1 (1H, s); 4.29 (d, 2H, J=4.7); 3.02 (br m, 4H); 2.47 (6H, s); 2.29 (3H, s); 1.13 (6H, t, J=7.0, 6.0) $^{13}$C NMR (DMSO) 159.85, 158.92, 150.89, 149.14, 145.63, 143.95, 143.25, 137.58, 131.58, 131.25, 130.18, 129.81, 128.87, 127.99, 126.38, 125.43, 127.17, 115.89, 54.90, 45.94, 42.75, 0.71, 8.03, 8.04, 7.89 | 578 |
| 19. | $^1$H NMR in DMSO: 10.59 (2H, s); 9.160 (2H, s); 7.84 (2H, dd, J=2.0, 8.8); 7.42 (7H, m, J=8.2, 5.3, 7.6); 7.26 (1H, s); 7.16 (1H, d, J=7.62); 7.11 (1H, d, J=8.21); 7.02 (2H, d, J=8.21); 6.1 (1H, s); 4.24 (2H, d, J=4.7); 2.68 (6H, d, J=4.7); 2.46 (6H, s); 2.29 (3H, s) | 550 |
| 20. | $^1$H NMR in DMSO: 10.6 (2H, s); 9.16 (2H, s); 7.85 (2H, dd, J=2.0, 8.2, 1.8); 7.47 (2H, d, J=7.62); 7.45 (2H, d, J=1.76); 7.11 (2H, d, J=7.62); 7.03 (2H, d, J=8.21); 6.11 (1H, s); 4.34 (br s, 2H); 3.9 (2H, m); 3.6 (br m, 2H); 2.47 (6H, s) | 594 |
| 21. | $^1$H NMR in DMSO: 10.48 (s, 2H); 9.15 (s, 2H); 7.78 (dd, 2H, J=1.76, 8.12 Hz); 7.55 (s, 2H); 7.07 (t, 1H, J=8.21 Hz); 6.98 (d, 2H, J=8.21 Hz): 6.51 (d, 1H, J=9.96Hz): 6.33 (m, 2H); 6.00 (s, 1H); 4.27 (t, 1H, J=5.74 Hz); 3.26 (m, 4H, overlapping H$_2$O); 3.13 (t, 2H, J=7.33 Hz); 2.46 (s, 6H); 1.41 (m, 2H); 1.29 (m, 2H); 0.99 (t, 3H, J=6.59 Hz) | — |
| 22. | $^1$H NMR in DMSO: 10.56 (brs, 2H); 9.44 (s, 1H); 9.16 (s, 2H); 7.81 (dd, 2H, J=8.79, 2.34); 7.53–7.46 (m, 4H); 7.23 (t, 1H, J=7.62); 7.00 (d, 2H, J=8.79); 6.76 (d, 1H, J=7.62); 6.05 (s, 1H); 2.46 (s, 6H); 2.04 (s, 3H); 1.52 (s, 6H) $^{13}$C NMR (75 MHz, DMSO) 171.36, 170.12, 160.53, 159.5, 149.90, 143.53, 139.60, 131.72, 131.22, 130.67, 128.85, 124.70, 122.84, 121.84, 119.20, 116.53, 80.43, 43.49, 25.14, 22.15, 8.78 | 636 |
| 23. | $^1$H NMR in DMSO: 10.55 (s, 2H); 9.68 (s, 1H); 9.16 (s, 2H); 7.81 (dd, 2H, J=8.21, 1.76); 7.60 (d, 1H, J=8.21); | 580 |

TABLE 1-continued

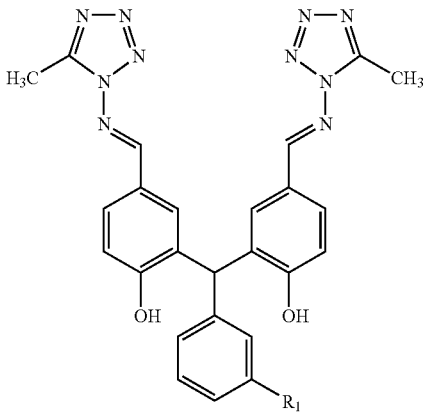

| | | |
|---|---|---|
| | 7.49 (d, 2H, J=1.76); 7.42 (s, 1H); 7.25 (t, 1H, J=7.62); 7.01 (d, 2H, J=8.79); 6.80 (d, 1H, J=8.21); 6.04 (s, 1H); 3.93 (s, 2H); 3.33 (s, 3H); 2.46 (s, 6H) | |
| 24. | $^1$H NMR in DMSO: 10.54 (s, 2H): 10.09 (s, 1H); 9.16 (s, 2H); 7.81 (dd, 2H, J=8.21. 1.76); 7.54 (d, 1H, J=8.79); 7.49 (d, 2H, J=1.76); 7.33 (s, 1H); 7.22 (t, 1H, J=7.62); 7.01 (d, 2H, J=8.79); 6.75 (d, 1H, J=7.62); 6.03 (s, 1H); 2.46 (s, 6H); 1.72 (m, 1H); 0.74 (m, 4H) | 576 |
| 25. | $^1$H NMR in DMSO: 10.63 (brs, 2H); 9.14 (s, 2H); 7.83 (dd, 2H, J=8.21, 1.76); 7.46 (t, 1H, J=7.62); 7.44 (d, 2H, J=1.76); 7.38 (d, 1H, J=7.62): 7.26 (d, 1H, J=7.62); 7.07 (s, 1H); 7.02 (d, 4H, J=8.21); 6.11 (s, 1H); 3.51 (t, 4H, J=7.03); 2.46 (s, 6H); 1.63 (m, 4H); 1.30 (m, 4H); 0.76 (t, 6H, J=7.03) | 748 |
| 26. | $^1$H NMR in DMSO: 10.62 (s, 2H); 9.14 (s, 2H); 7.83 (dd, 2H, J=8.21, 1.76); 7.50 (m, 2H); 7.44 (d, 2H, J=1.76); 7.34 (s, 1H); 7.26 (m, 1H); 7.02 (d, 2H, J=8.21); 6.14 (s, 1H); 5.16 (m, 2H); 5.03 (m, 2H); 2.46 (s, 6H) | 801 |
| 27. | $^1$H NMR in DMSO: 10.54 (s, 2H); 9.45 (s, 1H); 9.16 (s, 2H); 7.81 (dd, 2H, J=8.21, 1.76); 7.61 (d, 1H, J=8.21); 7.55 (s, 1H); 7.50 (d, 2H, J=1.76); 7.24 (t, 1H, J=7.62); 7.00 (d, 2H, J=8.79); 6.78 (d, 1H, J=8.21); 6.04 (s, 1H); 5.61 (brs, 1H): 2.46 (s, 6H); 1.31 (s, 6H) | 594 |
| 28. | $^1$H NMR in DMSO: 10.64 (brs, 2H); 9.15 (s, 2H); 7.84 (dd, 2H, J=8.79, 1.76); 7.46 (m, 3H); 7.37 (d, 1H, J=8.21); 726 (d, 1H, J=8.21); 7.08 (s, 1H); 7.02 (d, 2H, J=8.21); 6.12 (s, 1H); 3.50 (t, 4H, J=7.62); 2.47 (s, 6H); 1.68 (m, 4H); 0.89 (t, 6H, J=7.62) | 720 |
| 29. | $^1$H NMR in DMSO: 10.62 (brs, 2H); 9.15 (s, 2H); 7.83 (dd, 2H, J=8.21, 1.76); 7.48 (t, 1H, J=7.62); 7.44 (s, 2H); 7.40 (d, 1H, J=7.62); 7.28 (d, 1H, J=7.62); 7.12 (s, 1H); 7.02 (d, 2H, J=8.21); 6.12 (s, 1H); 3.73–3.62 (m, 8H); 2.47 (s, 6H); 2.12 (m, 4H) | 790 |
| 30. | $^1$H NMR in DMSO: 10.53 (s, 2H); 9.96 (s, 1H); 9.13 (s, 2H); 7.79 (dd, 2H, J=8.21, 1.76); 7.50 (d, 1H, J=7.62); 7.45 (s, 2H); 7.24 (m, 2H); 6.98 (d, 2H, J=8.21); 6.78 (d, 1H, J=7.62); 6.02 (s, 1H); 4.55 (s, 2H); 2.43 (s, 6H); 2.05 (s, 3H) | 608 |
| 31. | $^1$H NMR in DMSO: 10.63 (s, 2H); 9.14 (s, 2H); 7.83 (dd, 2H, J=8.21, 1.76); 7.45 (m, 4H); 7.22 (m, 2H); 7.02 (d, 2H, J=8.21); 6.12 (s, 1H); 3.43 (s, 6H); 2.47 (s, 6H) | 664 |

TABLE 1-continued

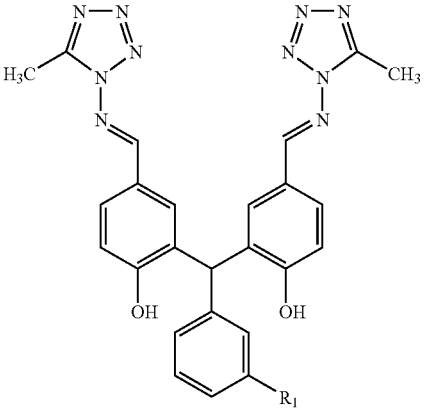

| | | |
|---|---|---|
| 32. | ¹H NMR in DMSO:<br>10.58 (brs, 2H); 9.15 (s, 2H); 7.82 (dd, 2H, J=8.21, 1.76); 7.48 (d, 2H, J=1.76); 7.32 (t, 1H, J=7.62); 7.09 (dd, 1H, J=8.21, 2.34); 7.00 (m, 3H); 6.84 (d, 1H, J=7.62); 6.06 (s, 1H); 3.68 (t, 2H, J=6.45); 3.46 (t, 2H, J=6.45); 2.47 (s, 6H); 2.35 (m, 2H) | 612 |
| 33. | ¹H NMR in DMSO:<br>10.55 (brs, 2H); 9.58 (s, 1H); 9.16 (s, 2H); 7.81 (dd, 2H, J=8.21, 1.76); 7.61 (d, 1H, J=7.62); 7.49 (s, 2H); 7.46 (s, 1H); 7.24 (t, 1H, J=7.62); 7.00 (d, 2H J=8.79); 6.80 (d, 1H, J=7.62); 6.04 (s, 1H); 5.49 (m, 1H); 3.92 (d, 2H, J=4.69); 2.46 (s, 6H) | 566 |
| 34. | ¹H NMR in DMSO:<br>10.47 (s, 2H) 9.15 (s, 2H); 7.77 (dd, 2H, J=2.34, 8.50 Hz); 7.54 (d, 2H, J=1.76 Hz): 7.07 (t, 1H, J=8.21); 6.98 (d, 2H, J=8.21 Hz); 6.54 (d, 1H, J=8.21 Hz); 6.39 (s, 1H); 6.32 (d, 1H, J=7.62 Hz); 5.99 (s, 1H); 4.39 (bs, 1H); 3.35 (m, 2H); 3.22 (m, 4H); 2.46 (s, 6H); 1.58 (m, 2H); 0.98 (t, 3H, J=6.74 Hz) | 596 |
| 35. | ¹H NMR in DMSO:<br>10.48 (s, 2H); 9.15 (s, 2H); 7.78 (dd, 2H, J=1.76, 8.21 Hz); 7.54 (d, 2H, J=1.76 Hz); 7.08 (t, 1H, J=8.21 Hz); 6.98 (d, 2H, J=8.21 Hz); 6.54 (d, 1H, J=8.21 Hz); 6.43 (s, 1H); 6.31 (d, 1H, J=7.03 Hz); 5.99 (s, 1H); 4.59 (bt, 1H, J=5.28 Hz); 3.45 (m, 2H); 3.25 (m, 4H); 2.47 (s, 6H); 0.99 (t, 3H, J=6.74 Hz) | 581 |
| 36. | ¹H NMR in DMSO:<br>10.49 (s, 2H); 9.15 (s, 2H); 7.78 (dd, 2H, J=1.76, 8.21 Hz); 7.50 (s, 2H); 7.13 (t, 1H, J=7.62 Hz); 6.98 (d, 2H, J=8.21 Hz); 6.80 (d, 1H, J=8.21 Hz); 6.68 (s, 1H); 6.47 (d, 1H, J=7.62 Hz); 6.01 (s, 1H); 4.60 (d, 1H, J=4.10 Hz); 3.57 (m, 1H); 3.41 (m, 2H); 2.76 (m, 2H); 2.47 (s, 6H); 1.73 (m, 2H); 1.41 (m, 2H) | (M + H)+ 549.1<br>(M − H)− 592.2 |
| 37. | ¹H NMR in DMSO:<br>10.47 (s, 2H); 9.14 (s, 2H): 7.80 (dd, J=2.35, 8.50, 1.76 Hz, 2H); 7.53 (d, J=1.76 Hz, 2H); 7.12 (t, J=2.62, 8.21 Hz, 1H); 6.99 (d, J=8.21 Hz, 2H); 6.58 (d, J=8.21 Hz, 1H); 6.44 (s, 1H); 6.35 (d, J=7.62 Hz, 1H); 6.0 (s, 1H); 4.39 (s, 1H); 3.38 (t, J=5.86, 5.86 Hz, 2H); 3.25 (m, 2H); 2.80 (s, 3H); 2.46 (s, 6H); 1.62 (m, 2H) | 580 m/z<br>(M − H) |
| 38. | ¹H NMR in DMSO:<br>10.48 (s, 2H); 9.15 (s, 2H); 7.77 (dd, 2H, J=2.34, 8.21 Hz); 7.54 (d, 2H, J=2.34 Hz); 7.08 (t, 1H, J=7.62 Hz); 6.98 (d, 2H, J=8.21 Hz); 6.52 (d, 1H, J=8.21 Hz); 6.34 (m, 2H); 6.00 (s, 1H); 3.86 (bt, 2H, J=5.86 Hz); 3.23 (m, 2H); 3.14 (m, 2H); 2.45 (s, 6H); 1.89 (s, 3H); 1.43 (m, 4H); 0.99 (t, 3H, J=6.74 Hz) | (M − H)+ 652.9<br>(M − H)− 650.9 |
| 39. | ¹H NMR in DMSO:<br>9.14 (s, 2H); 7.79 (dd, J=8.21, 1.76 Hz, 2H); | 565.9 m/z<br>(M − H) |

TABLE 1-continued

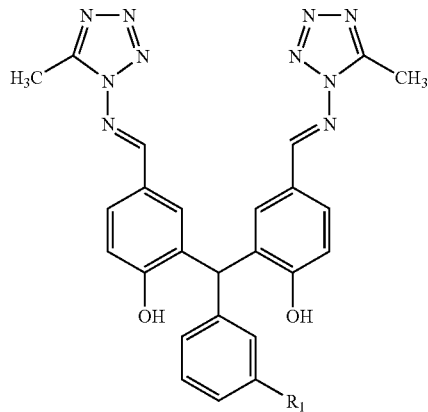

| | | |
|---|---|---|
| | 7.54 (s, 2H); 7.11 (t, J=8.21, 7.62 Hz, 1H); 6.98 (d, J=7.62 Hz, 2H): 6.57 (d, J=7.62 Hz, 1H); 6.47 (s, 1H); 6.34 (d, J=7.03 Hz, 1H): 5.99 (s, 1H); 3.50 (m, 2H); 2.84 (s, 3H) | (M-H) |
| 40. | $^1$H NMR in DMSO: 10.47 (s, 2H); 9.15 (s, 1H); 7.80 (dd, J=2.34, 7.34 Hz, 2H); 7.53 (d, J=1.76 Hz, 2H); 7.12 (t, J=7.62, 8.21 Hz, 1H); 7.00 (d, J=8.21 Hz, 2H); 6.56 (d, J=8.21 Hz, 1H); 6.40 (s, 1H); 6.36 (d, J=7.62 Hz, 1H); 6.01 (s, 1H); 4.29 (d, J=4.69 Hz, 1H); 3.21 (t, J=7.03, 7.62 Hz, 2H); 2.80 (s, 3H); 2.46 (s, 6H); 1.43 (m, 2H); 1.38 (m, 2H) | 594 m/z (M − H) |
| 41. | $^1$H NMR in DMSO: 10.48 (s, 2H); 9.16 (s, 2H); 7.80 (d, J=8.21 Hz, 2H); 7.55 (s, 2H); 7.10 (t, J=8.21, 7.03 Hz, 1H); 7.00 (d, J=8.21 Hz, 2H); 6.54 (d, J=8.21 Hz, 1H); 6.36 (m, 2H); 6.00 (s, 1H); 4.58 (bs, 1H); 3.45 (6s, 2H); 3.15 (t, J=6.45, 8.21 Hz, 2H); 2.45 (s, 6H); 1.46 (m, 2H); 0.75 (t, J=7.03, 7.62 Hz, 3H) | 594.2 m/z (M − H) |
| 42. | $^1$H NMR in DMSO: 10.49 (s, 2H); 9.16 (s, 2H); 7.80 (d, J=6.45 Hz, 2H); 7.56 (s, 2H); 7.10 (t, J=8.21, 7.62 Hz, 1H); 7.01 (d, J=8.80 Hz, 2H); 6.51 (d, J=8.21 z, 1H); 6.36 (d, 17.62 Hz, 1H); 6.28 (s, 1H); 6.02 (s, 1H); 4.29 (s, 1H); 3.18 (m, 4H); 2.46 (s, 6H), 1.47 (m, 4H); 1.35 (m, 2H),; 0.773 (t, J=7.03, 7.62 Hz, 3H) | 622.2 m/z (M − H) |
| 43. | $^1$H NMR in DMSO: 10.49 (s, 2H); 9.16 (s, 2H); 7.99 (d, J=8.21 Hz, 2H); 7.54 (s, 2H); 7.10 (t, J=7.62, 8.21 Hz, 1H); 7.00 (d, J=8.21 Hz, 2H); 6.51 (d, J=8.79 Hz, 1H); 6.34 (d, J=8.79 Hz, 2H); 6.00 (s, 1H); 4.23 (s, 1H); 3.26 (m, 2H); 3.12 (t, J=7.62, 7.03 Hz, 2H); 2.46 (s, 6H); 1.37 (m, 2H); 1.30 (m, 2H); 1.20 (m, 4H); 1.02 (t, J=7.03, 6.44 Hz, 3H) | 636.3 m/z (M − H) |
| 44. | $^1$H NMR in DMSO: 10.48 (s, 2H); 9.15 (s, 2H); 7.79 (d, J=8.21 Hz, 2H); 7.54 (s, 2H); 7.10 (t, J=8.21, 7.62 Hz, 1H); 7.00 (d, J=8.21 Hz, 2H); 6.51 (d, J=8.21 Hz, 1H); 6.34 (d, J=8.21 Hz, 2H); 6.00 (s, 1H); 4.23 (s, 1H); 3.26 (d, J=4.01 Hz, 2H); 3.12 (t, J=7.03, 7.62 Hz, 2H); 2.46 (s, 6H); 1.38 (m, 4H); 1.25 (m, 2H); 1.01 (t, J=7.03, 6.45 Hz, 3H) | 622.2 m/z (M − H) |

*All $^1$H NMR and $^{13}$C NMR spectra were acquired on a Varian Mercury VX 300 Spectrometer and referenced to tetramethylsilane (TMS) unless indicated otherwise. Chemical shifts and coupling constants are reported in parts per million (ppm) and Hertz (Hz) respectively.

TABLE 2

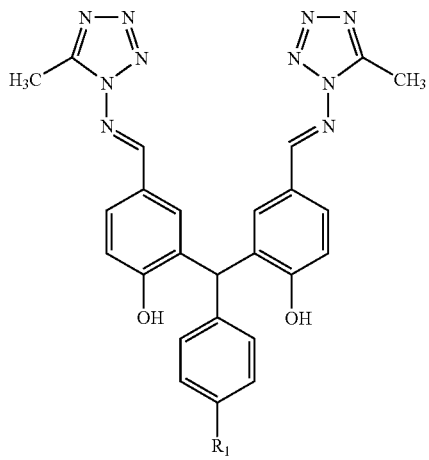

| Example # | R₁ | Name | NMR Data* | Mass Spec. |
|---|---|---|---|---|
| 45 | —SO₂N(CH₂CH₂OCH₃)₂ | 4-[[Bis[[5-(5-methyl-1H-tetrazol-1-yl)imino]methyl]-2-hydroxyphenyl]methylene]-N,N-bis(methoxyethyl)benzenesulfonamide | ¹H NMR in DMSO: 10.63 (s, 2H); 9.16 (s, 2H); 7.83 (dd, 2H, J=8.21, 1.76); 7.76 (d, 2H, J=8.79); 7.45 (d, 2H, J=2.34); 7.29 (d, 2H, J=8.79); 7.01 (d, 2H, J=8.79); 6.13 (s, 1H); 3.38 (m, 4H); 3.28 (m, 4H); 3.13 (s, 6H) 2.44 (s, 6H); ¹³C NMR (75 MHz, DMSO) 160.52, 159.46, 149.92, 148.21, 138.24, 131.82, 130.79, 130.36, 127.69, 123.03, 116.68, 71.16, 58.61, 48.47, 43.57 | (M − H)− 688 |
| 46 | —CH₂CH₂OH | 4-[[Bis[[5-(5-methyl-1H-tetrazol-1-yl)imino]methyl]-2-hydroxyphenyl]methylene]benzeneethanol | ¹H NMR in DMSO: 10.51 (s, 2H); 9.14 (s, 2H); 7.79 (dd, J=1.8, 8.2 Hz, 2H); 7.46 (d, J=1.8 Hz, 2H); 7.16 (d, J=7.6 Hz, 2H) 6.98 (m, J=4H); 6.04 (s, 1H) 4.58 (bs, 1H); 3.59 (t, J=7.0 Hz, 2H); 2.70 (t, J=6.4, 7.0 Hz); 2.46 (s, 6H) | — |
| 47 | —S(O)₂—N(morpholinyl) | 2,2'-[[4-(4-Morpholinylsulfonyl)phenyl]methylene]bis[4-[[5-yl)imino]methyl]]phenol | ¹H NMR in DMSO: 10.67 (s, 2H); 9.17 (s, 2H); 7.83 (dd, 2H, J=8.21, 2.34); 7.69 (d, 2H, J=8.21); 7.46 (d, 2H, J=1.76); 7.35 (d, 2H, J=8.21); 7.02 (d, 2H, J=8.21); 6.15 (s, 1H); 3.61 (m, 4H); ¹³C NMR (75 MHz, DMSO) 160.52, 159.49, 149.92, 149.00, 133.08, 131.60, 131.07, 130.55, 130.36, 128.53, 123.08, 116.67, 65.96, 46.64, 43.76, 8.79 | (M − H)− 642 |
| 48 | —N(morpholinyl) | 2,2'-[[4-(4-Morpholinyl)phenyl]methylene]bis[4-[[(5-methyl-yl)imino]methyl]]phenol | ¹¹H NMR in DMSO: 10.47 (s, 2H); 9.15 (s, 2H); 7.78 (dd, J=1.76, 2.34, 8.50 Hz, 2H); 7.46 (d, J=1.76 Hz, 2H); J=4.69 Hz, 4H); 3.07 (t, J=4.69 Hz, 4H); 2.47 (s, 6H) | (M + H)+ 580.1 |
| 49 | —CH₂CH₂OC(O)CH₃ | 4-[[Bis[[5-(5-methyl-1H-tetrazol-1-yl)imino]methyl]-2-hydroxyphenyl]methylene]benzeneethanol, acetate ester | ¹H NMR in DMSO: 520 (s, 2H); 9.15 (s, 2H); 7.80 (dd, J = 1.7, 8.2, 8.8 Hz, 2H); 7.45 (d, J = 1.7 Hz, 2H); 1 (d, J = 8.2 Hz, 2H); 7.03 (d, J = 8.2 Hz, 2H); 9 (d, J = 8.2 Hz, 2H); 6.05 (s, 1H); 4.20 (t, J = Hz, 2H); 2.87 (t, J = 6.4, 7.0 Hz, 2H); 2.46; 1.98 (s, 3H) | 580, 552, 525, 456 |
| 50 | —N(piperidinyl) | 2,2'-[[4-(1-Piperidinyl)phenyl]methylene]bis[4-[[(5-methyl-1H-tetrazol-1-yl)imino]methyl]]phenol | ¹H NMR in DMSO:) 10.48 (s, 2H); 9.15 (s, 2H); 7.80 (d, J=8.21 Hz, 2H); 7.47 (s, 2H); 7.00 (d, J=8.79 Hz, 2H); 6.93 (s, 2H); 5.98 (s, 1H); 3.11 (m, 4H); 2.47 (s, 6H); 1.62 (m, 4H); 1.54 m, 2H) | 576 (M − H) |

*All ¹H NMR and ¹³C NMR spectra were acquired on a Varian Mercury VX 300 Spectrometer and referenced to tetramethylsilane (TMS) unless indicated otherwise. Chemical shifts and coupling constants are reported in parts per million (ppm) and Hertz (Hz) respectively.

Scheme 1 illustrates an aspect of the invention regarding methods of preparing the compound of Formula III:

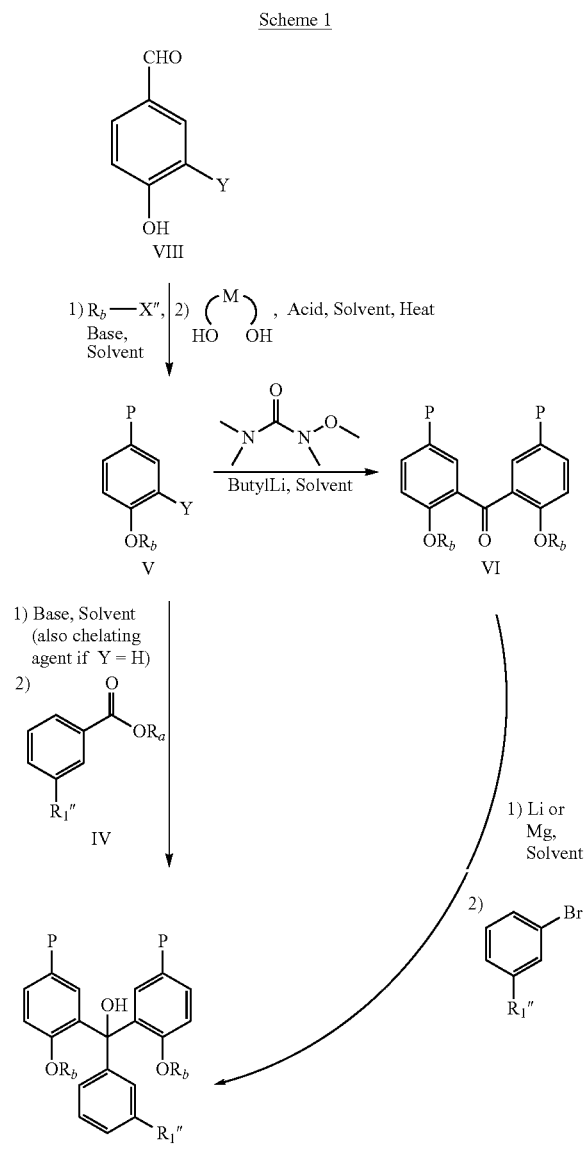

Y, $R_a$, $R_b$, M, X″, $R_1''$, and P are defined and selected in accordance with the description of the invention above.

Example 51 illustrates the effectiveness of the compounds used in the method of the invention in inhibiting the viral replication of RSV in cell culture.

Example 51

Cell Culture Assay for Inhibition of Pneumovirus Replication

The replication of many viruses may be quantitatively assessed in the laboratory in various cell or tissue culture systems. Such in vitro culture methodologies are available and useable by those skilled in the art for the propagation and quantitative measurement of the replication of pneumoviruses. The following procedure was used for the in vitro quantitative measure of RSV replication.

Using the procedure described in this example, compounds of the present invention were evaluated for their ability to inhibit the replication of the virus in cell culture. By adding compounds at various concentrations to the culture medium, a dose response effect of the compound on virus replication was determined. A useful quantitative measure of the inhibition of RSV replication in this assay is the concentration of the compound at which virus replication in cell culture is inhibited by 50% in comparison to that observed in the absence of the compound (50% Inhibitory Concentration, $IC_{50}$). In the case of RSV, $IC_{50}$ values are defined as the concentration of compound that protected 50% of the cell monolayer from virus-induced cytopathic effect (syncytia formation).

Anti-pneumovirus compounds of the invention were screened for antiviral activity against RSV (strain Long) on cultured HEp2 cells. Standard 96-well culture plates were seeded with $4 \times 10^4$ HEp2 cells in 200 μL of Minimal Essential Medium with Earlessalts (EMEM) supplemented with 10% fetal bovine serum (FBS). Twenty-four to 30 hours later, the cells were infected with a dilution of RSV in Medium 199 (GIBCO/BRL) with 5% FBS that had been titrated to yield >85% destruction of the cell monolayer in 60 hours. After 1 hour at 37° C., compounds were added to wells of the plate in a final DMSO concentration of 0.5% as a series of 10 two-fold dilutions of the compound.

Virus control wells (VC, no test compound) and cell culture control wells (CC, no virus, no test compound) were also included on each plate. Plates were incubated in a humidified atmosphere at 37° C. and 5% carbon dioxide. After 60 hours, 100 μL of a 5% solution of glutaraldehyde in water was added to each well, and the wells were incubated at room temperature for 1 hour. The fixative was removed, and the cells were stained with a 0.1% solution of crystal violet in water for 15-30 minutes. After rinsing and drying the plates, the optical density of the wells was measured at 570 nm ($OD_{570}$).

To determine $IC_{50}$ values for the test compounds, the mean value of the $OD_{570}$ readings of the virus control wells (VC) on a plate was subtracted from the $OD_{570}$ readings of all wells on that plate. The $IC_{50}$ values were then calculated according to the following formula:

$$IC_{50} = [(Y-B)/(A-B)] \times (H \times L) + L$$

where Y represents the mean $OD_{570}$ reading of the cell control wells (CC) divided by 2; B represents the mean $OD_{570}$ reading of wells of the compound dilution nearest to and below Y; A represents the mean $OD_{570}$ reading of wells of the compound dilution nearest to and above Y; L represents the compound concentration at B; and H represents the compound concentration at A.

A similar assay is useful for various strains of human RSV, including subtype A and subtype B viruses, as well as other pneumoviruses.

The results of the cell culture assay for inhibition of the replication of several pneumoviruses for representative compounds used in the method of the invention range from 0.1 nM to 1 μM. The low concentrations of test compounds required to achieve 50% inhibition of RSV replication in cell culture indicate that the compounds used in the method of the invention are effective at inhibiting the pneumovirus replication process. It is also demonstrated here that the compounds of the invention are dramatically more potent than Ribavirin at inhibiting viral replication.

Example 52 demonstrates that the compounds of the invention are not toxic or detrimental to the health of normal cells at concentrations well above those needed to inhibit pneumovirus replication.

Example 52

Assay for Cytotoxicity of Inhibitors of Pneumovirus Replication

To demonstrate that the compounds of the invention are not toxic or detrimental to the health of normal cells, compounds of the invention were evaluated in an in vitro cytotoxicity assay. One useful assay for determining the cytotoxic effects of compounds on the growth of cells is a tetrazolium-based calorimetric method (Mossman, T., J. Immun. Methods, 65 (1-2): 55-63 (1983)). This assay measures cell viability, and therefore cytotoxicity, by quantitatively detecting the in situ reduction of 3-(4,5-dimethylthiazol-2-yl)-2,5-diphenyltetrazolium bromide (MTT) by viable cells. Cells are seeded in 96-well plates in DMEM containing 5% FBS at a density of $4 \times 10^3$ cells per well. After incubation for 4 hours at 37° C. and 5% $CO_2$, 2-fold serial dilutions of compound in 1% DMSO (or solvent alone) are added to quadruplicate wells, and the plates are incubated for an additional 68 hours at 37° C. and 5% $CO_2$, which is equivalent to 3 to 4 cell doublings. The culture medium is removed, and the cells are treated with 1 mg/ml of MTT in phosphate-buffered saline, pH 7.2 for 4 hours at 37° C. and 5% $CO_2$. After removal of the unreduced MTT, the reduced blue formazan crystals produced by the viable cells are solubilized by the addition of 0.04N HCl in isopropanol. The optical density at 570 nm ($OD_{570}$) of each well is read using a suitable microplate reader. Cell viability is expressed as the percentage of optical density for compound-treated cells relative to the optical density of solvent alone-treated control wells. The highest compound concentration resulting in an optical density of $\geq 75\%$ of the control is represented as the cellular cytotoxicity value ($CC_{75}$).

The results of the MTT cytotoxicity assay using compounds prepared, range from 3 to >50 (µM).

The cellular cytotoxicity ($CC_{75}$) values for the representative compounds are considerably higher than the antiviral ($IC_{50}$) values for these compounds. These results indicate that the compounds of the invention are highly selective and, at therapeutically effective doses, they do not detrimentally affect the health of normal cells. A measure of this selectivity is provided by the high selective index value (SI), which is defined as $CC_{75}/IC_{50}$. The high SI values exhibited by compounds of the invention indicate very desirable attributes of the compounds.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:
1. A compound having the formula:

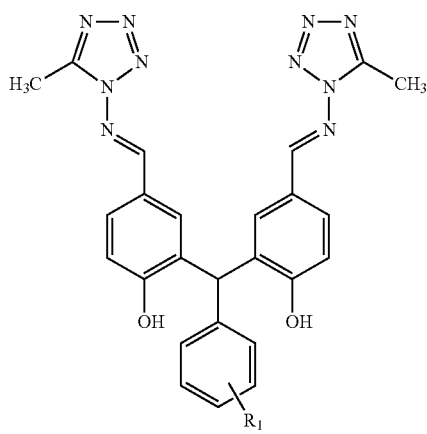

wherein:
$R_1$ represents a radical selected from the group consisting of

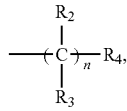

—$NR_5R_6$, —$SO_2NR_7R_8$, hydroxyalkyl, hydroxyalkoxy, polyhydroxyalkyl, alkoxyalkoxy, polyfluoroalkyl, dialkylaminoalkyl, $R_9$, —$OR_9$,

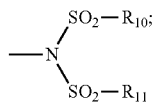

n being an integer from 1 to 4;
$R_2$ and $R_3$ are each independently selected from the group consisting of straight or branched chain alkyl and hydrogen;
$R_4$ is a radical selected from the group consisting of a substituted or unsubstituted phenyl radical, an unsubstituted or substituted heterocyclic radical, and —$NR_{12}R_{13}$;
$R_5$ and $R_7$ are independently selected from the group consisting of alkoxyalkyl, hydroxyalkyl, polyhydroxyalkyl, aralkyl, $R_9$, —(C=O)$R_{14}$ and —(C=O)$R_9$;
$R_6$, $R_8$, $R_{12}$, and $R_{13}$ are independently selected from the group consisting of hydrogen, alkyl, alkoxyalkyl, polyfluoroalkyl, hydroxyalkyl, polyhydroxyalkyl, aralkyl, $R_9$, —(C=O)$R_{15}$ and —(C=O)$R_9$;
or $R_5$ and $R_6$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;
or $R_7$ and $R_8$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

said phenyl and heterocyclic radical substituents being at least one selected from the group consisting of alkyl, amino, hydroxy, carbonyl, monoalkylamino, dialkylamino, halogen, and alkoxy;

$R_9$ is a radical of the formula —W—O(C═O)—CH$_3$, W being a straight- or branched-chain alkylene group of 1 to 6 carbon atoms;

$R_{10}$ and $R_{11}$ are radicals independently selected from the group consisting of alkyl, halo, haloalkyl, and polyfluoroalkyl;

$R_{14}$ is a hydroxyalkyl, alkoxyalkyl or cycloalkyl group;

$R_{15}$ is an alkyl, hydroxyalkyl, alkoxyalkyl or cycloalkyl group, and pharmaceutically acceptable salts of said compound.

2. A compound according to claim 1, selected from the group consisting of:
- 2,2'-[[3-(2,2,2-Trifluoroethyl)phenyl]methylene]bis[4-[[(5-methyl-1H-tetrazol-1-yl)imino]methyl]]phenol;
- 2,2'-[[3-(4-Morpholinyl)phenyl]methylene]]bis[4-[[(5-methyl-1H-tetrazol-1-yl)imino]methyl]]phenol;
- 2,2'-[[3-(1-Piperidinyl)phenyl]methylene]bis[4-[[(5-methyl-1H-tetrazol-1-yl)imino]methyl]]phenol;
- 2,2'-[[3-(4-Morpholinylsulfonyl)phenyl]methylene]bis[4-[[(5-methyl-1H-tetrazol-1-yl)imino]methyl]]phenol;
- 2,2'-[[3-(Methoxyethoxy)phenyl]methylene]bis[4-[[(5-methyl-1H-tetrazol-1-yl)imino]methyl]]phenol;
- 2,2'-[[[3-Bis(phenylmethyl)amino]phenyl]methylene]]bis[4-[[(5-methyl-1H-tetrazol-1-yl)imino]methyl]]phenol;
- 2,2'-[[3-[1-(4-Methylpiperazinyl)methyl]phenyl}methylene]bis[4-[[(5-methyl-1H-tetrazol-1-yl)imino]methyl]]phenol;
- 2,2'-[[3-(Diethylaminomethyl)phenyl]methylene]bis[4-[[(5-methyl-1H-tetrazol-1-yl)imino]methyl]]phenol;
- 2,2'-[[3-(Dimethylaminomethyl)phenyl]methylene]bis[4-[[(5-methyl-1H-tetrazol-1-yl)imino]methyl]]phenol;
- 2,2'-[[3-[4-(Morpholinyl)methyl]phenyl}methylene]bis[4-[[(5-methyl-1H-tetrazol-1-yl)imino]methyl]]phenol;
- 2,2'-[[3-[N-(4-Hydroxybutyl)-N-ethylamino]phenyl]methylene]bis[4-[[(5-methyl-1H-tetrazol-1-yl)imino]methyl]]phenol;
- 2,2'-[[3-[2-(1,1-Dioxide-2,3,4,5-tetrahydro)isothiazolyl]phenyl}methylene]bis[4-[[(5-methyl-1H-tetrazol-1-yl)imino]methyl]]phenol;
- 2,2'-[[3-[N-(3-Hydroxypropyl)-N-ethylamino]phenyl]methylene]bis[4-[[(5-methyl-1H-tetrazol-1-yl)imino]methyl]phenol;
- 2,2'-[[3-[N-(2-Hydroxyethyl)-N-ethylamino]phenyl]methylene]bis[4-[[(5-methyl-1H-tetrazol-1-yl)imino]methyl]]phenol;
- 2,2'-[[3-[1-(4-Hydroxypiperidinyl)]phenyl]methylene]bis[4-[[(5-methyl-1H-tetrazol-1-yl)imino]methyl]]phenol;
- 2,2'-[[3-[N-(3-Hydroxypropyl)-N-methylamino]phenyl]methylene]bis[4-[[(5-methyl-1H-tetrazol-1-yl)imino]methyl]]phenol;
- 2,2'-[[3-[N-(4-Acetoxybutyl)-N-ethylamino]phenyl]methylene]bis[4-[[(5-methyl-1H-tetrazol-1-yl)imino]methyl]]phenol;
- 2,2'-[[3-[N-(2-Hydroxyethyl)-N-methylamino]phenyl]methylene]bis[4-[[(5-methyl-1H-tetrazol-1-yl)imino]methyl]]phenol;
- 2,2'-[[3-[N-(4-Hydroxybutyl)-N-methylamino]phenyl]methylene]bis[4-[[(5-methyl-1H-tetrazol-1-yl)imino]methyl]]phenol;
- 2,2'-[[3-[N-(2-Hydroxyethyl)-N-propyl]amino]phenyl]methylene]bis[4-[[(5-methyl-1H-tetrazol-1-yl)imino]methyl]]phenol;
- 2,2'-[[3-[N-(4-Hydroxybutyl)-N-propylamino]phenyl]methylene]bis[4-[[(5-methyl-1H-tetrazol-1-yl)imino]methyl]]phenol;
- 2,2'-[[3-[N-(6-Hydroxyhexyl)-N-ethylamino]phenyl]methylene]bis[4-[[(5-methyl-1H-tetrazol-1-yl)imino]methyl]]phenol; and
- 2,2'-[[3-[N-(5-Hydroxypentyl)-N-ethylamino]phenyl]methylene]bis[4-[[(5-methyl-1H-tetrazol-1-yl)imino]methyl]]phenol.

3. The compound according to claim 1 having the formula:

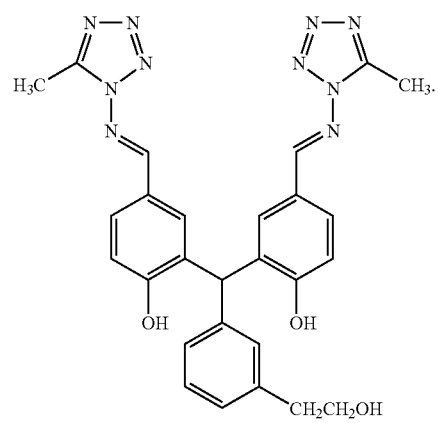

4. The compound according to claim 1 having the formula:

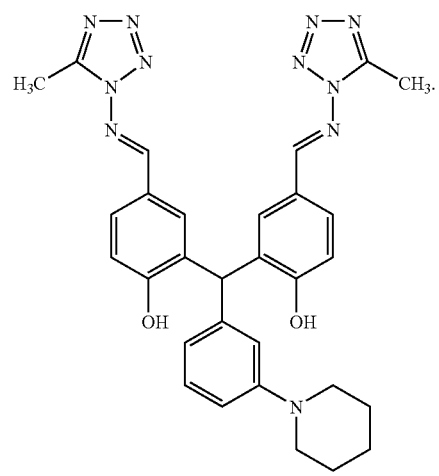

5. The compound according to claim 1 having the name 2,2'-[[3-[N-(4-Hydroxybutyl)-N-ethylamino]phenyl]methylene]bis[4-[[(5-methyl-1H-tetrazol-1-yl)imino]methyl]]phenol.

6. The compound according to claim 1 having the name 2,2'-[[3-[N-(2-Hydroxyethyl)-N-methylamino]phenyl]methylene]bis[4-[[(5-methyl-1H-tetrazol-1-yl)imino]methyl]]phenol.

7. The compound according to claim 1 having the name 2,2'-[[3-[N-(2-Hydroxyethyl)-N-ethylamino]phenyl]methylene]bis[4-[[(5-methyl-1H-tetrazol-1-yl)imino]methyl]]phenol.

8. A pharmaceutical composition for treating pneumovirus infection, said composition comprising a compound according to claim 1 in a dose amount effective to attenuate infectivity of said virus, and a pharmaceutically acceptable carrier medium.

9. A pharmaceutical composition according to claim 8, further comprising at least one supplemental active agent selected from the group consisting of interferon, ribavirin and an immunomodulator, an immunoglobulin, an anti-flammatory agent, an antibiotic, an anti-viral and an anti-infective.

10. A pharmaceutical composition according to claim 8, wherein said pharmaceutically acceptable carrier medium comprises ethanol.

11. A pharmaceutical composition according to claim 8, wherein said pharmaceutically acceptable carrier medium comprises propylene glycol.

12. A pharmaceutical composition according to claim 8, wherein said pharmaceutically acceptable carrier medium comprises water.

13. A pharmaceutical composition according to claim 10, wherein said pharmaceutically composition comprises at least 50% ethanol.

14. A pharmaceutical composition according to claim 10, wherein said pharmaceutically composition comprises at least 60% ethanol.

15. A pharmaceutical composition according to claim 10, wherein said pharmaceutically composition comprises at least 70% ethanol.

16. A pharmaceutical composition according to claim 10, wherein said pharmaceutically composition comprises at least 80% ethanol.

17. A pharmaceutical composition according to claim 10, wherein said pharmaceutically composition comprises at least 90% ethanol.

18. A pharmaceutical composition according to claim 17, wherein said pharmaceutically composition comprises less than 5% water.

19. A pharmaceutical composition according to claim 10, wherein said pharmaceutically acceptable carrier medium comprises ethanol, water, and propylene glycol.

20. A pharmaceutical composition according to claim 19, wherein said pharmaceutically composition comprises about 85% ethanol, about 10% propylene glycol, and about 5% water.

21. A method of treatment of pneumovirus infection in a patient in need of said treatment, said method comprising administering to said patient a therapeutically effective amount of a compound according to claim 1.

22. A method as claimed in claim 21, wherein said compound is administered through inhalation or intribation.

23. A method as claimed in claim 21, wherein said compound is administered by an electrohydrodynamic delivery device.

24. A method as claimed in claim 21, wherein said electrohydrodynamic delivery device is hand-held.

25. A method as claimed in claim 23, wherein said electrohydrodynamic delivery device is disposable.

26. A method as claimed in claim 23, wherein said electrohydrodynamic delivery device is for a single user.

27. A method as claimed in claim 23, wherein said electrohydrodynamic delivery device comprises a removable mouthpiece.

28. A method as claimed in claim 23, wherein said electrohydrodynamic delivery device comprises a mask.

29. A method of treating cells in culture that are susceptible to infection by, or infected or contaminated with a pneumovirus, said method comprising administering to said cultures an effective amount of a compound according to claim 1.

30. A method of treating biological materials that are susceptible to infection by, or infected or contaminated with a pneumovirus, said method comprising administering to said materials an effective amount of a compound according to claim 1.

31. A compound having the formula:

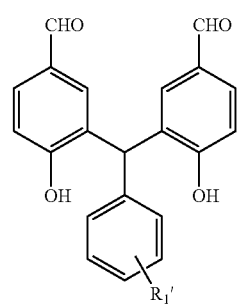

II wherein:
$R_1'$ represents a radical selected from the group consisting of

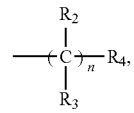

—$NR_5R_6$, —$SO_2NR_7R_8$, hydroxyalkyl, hydroxyalkoxy, polyhydroxyalkyl, alkoxyalkoxy, polyfluoroalkyl, dialkylaminoalkyl, $R_9$, —$OR_9$,

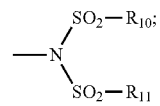

n being an integer from 1 to 4;
$R_2$ and $R_3$ are each independently selected from the group consisting of straight or branched chain alkyl and hydrogen;
$R_4$ is a radical selected from the group consisting of a substituted or unsubstituted phenyl radical, an unsubstituted or substituted heterocyclic radical, and —$NR_{12}R_{13}$;
$R_5$ and $R_7$ are independently selected from the group consisting of alkoxyalkyl, hydroxyalkyl, polyhydroxyalkyl, aralkyl, $R_9$, —(C=O)$R_{14}$ and —(C=O)$R_9$;
$R_6$, $R_8$, $R_{12}$, and $R_{13}$ are independently selected from the group consisting of hydrogen, alkyl, alkoxyalkyl, polyfluoroalkyl, hydroxyalkyl, polyhydroxyalkyl, aralkyl, $R_9$, —(C=O)$R_{15}$ and —(C=O)$R_9$;
or $R_5$ and $R_6$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

or $R_7$ and $R_8$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

said phenyl and heterocyclic radical substituents being at least one selected from the group consisting of alkyl, amino, hydroxy, carbonyl, monoalkylamino, dialkylamino, halogen, and alkoxy;

$R_9$ is a radical of the formula —W—O(C=O)—CH$_3$, W being a straight- or branched-chain alkylene group of 1 to 6 carbon atoms;

$R_{10}$ and $R_{11}$ are radicals independently selected from the group consisting of alkyl, halo, haloalkyl, and polyfluoroalkyl;

$R_{14}$ is a hydroxyalkyl, alkoxyalkyl or cycloalkyl group;

$R_{15}$ is an alkyl, hydroxyalkyl, alkoxyalkyl or cycloalkyl group, and pharmaceutically acceptable salts of said compound.

32. A compound having the formula:

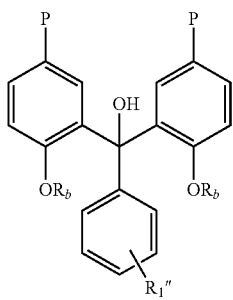

III wherein $R_b$ is selected from the group consisting of —CH$_2$OCH$_3$, —CH$_2$OCH$_2$CH$_3$, —CH(CH$_3$)OCH$_2$CH$_3$, —CH$_2$—OCH$_2$CH$_2$—OCH$_3$,

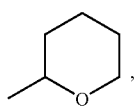,

—CH$_2$—OCH$_2$CH$_2$—Si(CH$_3$)$_3$, —CH$_3$, —CH$_2$C$_6$H$_5$, —(CH$_2$)$_2$Si(CH$_3$)$_3$, —CON(R$_c$R$_d$)$_2$, —CSN(R$_c$R$_d$)$_2$, and —PO(NR$_c$R$_d$)$_2$;

$R_c$ and $R_d$ are independently selected from an alkyl group;

$R_1''$ represents a radical selected from the group consisting of

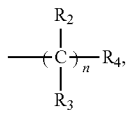

—NR$_5$R$_6$, —SO$_2$NR$_7$R$_8$, hydroxyalkyl, hydroxyalkoxy, polyhydroxyalkyl, alkoxyalkoxy, polyfluoroalkyl, dialkylaminoalkyl, R$_9$, —OR$_9$,

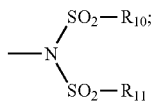

n being an integer from 1 to 4;

$R_2$ and $R_3$ are each independently selected from the group consisting of straight or branched chain alkyl and hydrogen;

$R_4$ is a radical selected from the group consisting of a substituted or unsubstituted phenyl radical, an unsubstituted or substituted heterocyclic radical, and —NR$_{12}$R$_{13}$;

$R_5$ and $R_7$ are independently selected from the group consisting of alkoxyalkyl, hydroxyalkyl, polyhydroxyalkyl, aralkyl, R$_9$, —(C=O)R$_{14}$ and —(C=O)R$_9$;

$R_6$, $R_8$, $R_{12}$, and $R_{13}$ are independently selected from the group consisting of hydrogen, alkyl, alkoxyalkyl, polyfluoroalkyl, hydroxyalkyl, polyhydroxyalkyl, aralkyl, R$_9$, —(C=O)R$_{15}$ and —(C=O)R$_9$;

or $R_5$ and $R_6$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

or $R_7$ and $R_8$ taken together with the nitrogen to which they are attached form a substituted or unsubstituted heterocyclic radical, said heterocyclic radical optionally containing one to two additional heteroatoms independently selected from the group consisting nitrogen, oxygen, and sulfur;

said phenyl and heterocyclic radical substituents being at least one selected from the group consisting of alkyl, amino, hydroxy, carbonyl, monoalkylamino, dialkylamino, halogen, and alkoxy;

$R_9$ is a radical of the formula —W—O(C=O)—CH$_3$, W being a straight- or branched-chain alkylene group of 1 to 6 carbon atoms;

$R_{10}$ and $R_{11}$ are radicals independently selected from the group consisting of alkyl, halo, haloalkyl, and polyfluoroalkyl;

$R_{14}$ is a hydroxyalkyl, alkoxyalkyl or cycloalkyl group; and $R_{15}$ is an alkyl, hydroxyalkyl, alkoxyalkyl or cycloalkyl group.

* * * * *

UNITED STATES PATENT AND TRADEMARK OFFICE
CERTIFICATE OF CORRECTION

PATENT NO.         : 8,202,896 B2                                          Page 1 of 1
APPLICATION NO.    : 10/524162
DATED              : June 19, 2012
INVENTOR(S)        : Nitz et al.

It is certified that error appears in the above-identified patent and that said Letters Patent is hereby corrected as shown below:

On the Title Page, item (75), Fourth Inventor: "Sylvie Laguerre" should be
--Sylvie Laquerre--.

In the Claims:

Claim 8, Col. 111, line 5 "treating pneumovirus" should be --treating or preventing pneumovirus--.

Claim 32, Col. 113, line 28 "P" in the formula should be --CHO--.

Signed and Sealed this
Twenty-eighth Day of October, 2014

Michelle K. Lee
*Deputy Director of the United States Patent and Trademark Office*